United States Patent
Cohen et al.

(10) Patent No.: US 11,530,235 B2
(45) Date of Patent: Dec. 20, 2022

(54) COMPOUNDS AND METHODS USED IN ASSESSING MONO-PARP ACTIVITY

(71) Applicant: Oregon Health & Science University, Portland, OR (US)

(72) Inventors: Michael Cohen, Portland, OR (US); Ian Carter-O'Connell, Portland, OR (US); Rory Morgan, Portland, OR (US); Haihong Jin, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 16/715,907

(22) Filed: Dec. 16, 2019

(65) Prior Publication Data

US 2020/0123192 A1    Apr. 23, 2020

Related U.S. Application Data

(62) Division of application No. 15/356,040, filed on Nov. 18, 2016, now abandoned.

(60) Provisional application No. 62/258,397, filed on Nov. 20, 2015.

(51) Int. Cl.
*C07H 19/207* (2006.01)
*C12N 9/10* (2006.01)
*C12Q 1/48* (2006.01)
*A61K 38/00* (2006.01)

(52) U.S. Cl.
CPC ......... *C07H 19/207* (2013.01); *C12N 9/1077* (2013.01); *C12Q 1/48* (2013.01); *C12Y 204/0203* (2013.01); *G01N 2333/91142* (2013.01); *G01N 2500/02* (2013.01); *G01N 2500/10* (2013.01)

(58) Field of Classification Search
CPC ............ C12N 9/1077; C12Y 204/0203; C07H 19/2077
See application file for complete search history.

(56) References Cited

U.S. PATENT DOCUMENTS

2003/0165488 A1    9/2003   Kletzien et al.
2018/0320219 A1   11/2018   Kim

FOREIGN PATENT DOCUMENTS

WO     WO-0222792 A2 *  3/2002   ........... C12N 9/1077

OTHER PUBLICATIONS

Hottiger et al. (2010) Toward a unified nomenclature for mammalian ADP-ribosyltransferases, Trends Biochem. Sci. , vol. 35, pp. 208-219.*

NCBI-EHA99817 (Mar. 2015) www.ncbi.nlm.nih.gov/protein/EHA99817.1, pp. 1-3.*

Jang et al. (2008) Serine/Arginine Protein-Specific Kinase 2 Promotes Leukemia Cell Proliferation by Phosphorylating Acinus and Regulating Cyclin A1; Cancer Res., vol. 68, No. 12, pp. 4559-4570.*

Affar, et al., "Immunological determination and size characterization of poly(ADP-ribose) synthesized in vitro and in vivo," Anal. Biochem., vol. 1428, No. 2-3, 1998, pp. 280-283.

Ame, et al., "The PARP superfamily," BioEsssays, vol. 26, No. 10, 2004, pp. 882-893.

Ashburner, et al., "Gene ontology: tool for the unification of biology The Gene Ontology Consortium," Nat. Genetics, vol. 25, No. 1, 2000, pp. 25-29.

Carter-O'Connell and Cohen, "Identifying Direct Protein Targets of Poly-ADP-Ribose Polymerases (PARPs) Using Engineered PARP Variants-Orthogonal Nicotinamide Adenine Dinucleotide (NAD+) Analog Pairs," Curr. Prot. Chem. Biol., vol. 7, No. 2, 2015, pp. 121-139.

Carter-O'Connell, et al., "Engineering the substrate specificity of ADP-ribosyltransferases for identifying direct protein targets," J. Am. Chem. Soc., vol. 136, No. 14, 2014, pp. 5201-5204.

Chen, et al., "Proteomic identification of proteins associated with the osmoregulatory transcription factor TonEBP/OREBP: functional effects of Hsp90 and PARP-1," Am. J. Phys. Ren. Phys., vol. 292, No. 3, 2007, pp. F981-992.

Chiarugi, et al., "The NAD metabolome—a key determinant of cancer cell biology," Nat. Rev. Cancer, vol. 12, No. 11, 2012, pp. 741-752.

Citarelli, et al., "Evolutionary history of the poly(ADP-ribose) polymerase gene family in eukaryotes," BMC Evolut. BioL, vol. 10, No. 308, 2010, 26 pages.

Cosi and Marien, "Implication of poly (ADP-ribose) polymerase (PARP) in neurodegeneration and brain energy metabolism. Decreases in mouse brain NAD+ and ATP caused by MPTP are prevented by the PARP inhibitor benzamide," Ann. NY Acad. Sci., vol. 890, 1999, pp. 227-239.

Daniels, et al., "Phosphoproteomic approach to characterize protein mono- and poly(ADP-ribosyl)ation sites from cells," J. Proteome Res., vol. 13, No. 8, 2014, pp. 3510-3522.

Daugherty, et al., "Rapid evolution of PARP genes suggests a broad role for ADP-ribosylation in host-virus conflicts," PLoS Genetics, vol. 10, No. 5, 2014, 13 pages.

Feijs, et al., "ARTD10 substrate identification on protein microarrays: regulation of GSK3Beta by mono-ADP-ibosylation," Cell Comm. Sig., vol. 11, No. 1, 2013, 11 pages.

Haikarainen, et al., "Structural basis and selectivity of tankyrase inhibition by a Wnt signaling inhibitor WIKI4," PLoS One, vol. 8, No. 6, 2013, 8 pages.

(Continued)

*Primary Examiner* — Manjunath N Rao
*Assistant Examiner* — Samuel W Liu
(74) *Attorney, Agent, or Firm* — Tanya M. Harding; C. Rachal Winger; Lee & Hayes, P.C.

(57)    ABSTRACT

Mutant mono ADP-ribose-polymerases (mono-PARP) proteins and small molecule compound substrates specific for the mutant mono-PARP proteins as well as methods of using these compositions to identify protein targets of the mono-PARPs and to screen for antagonists of the mono-PARPs are described.

10 Claims, 13 Drawing Sheets

Specification includes a Sequence Listing.

(56) References Cited

OTHER PUBLICATIONS

Hottiger et al., "Toward a unified nomenclature for mammalian ADP-ribosyltransferases," Trends Biochem. Sci., vol. 35, No. 4, 2010, pp. 208-219.

Hu, et al., "Regulation of myofibroblast differentiation by poly(ADP-ribose) polymerase 1," Am. J. Pathol., vol. 182, No. 1, 2013, pp. 71-83.

Ji and Tulin, "The roles of PARP1 in gene control and cell differentiation," Curr. Opin. Genetics Dev., vol. 20, No. 5, 2010, pp. 512-518.

Jiang, et al., "Clickable NAD Analogues for Labeling Substrate Proteins of Poly(ADP-ribose) Polymerases," J. Am. Chem. Soc., vol. 132, No. 27, 2010, pp. 9363-9372.

Jungmichel, et al., "Proteome-wide identification of poly(ADP-Ribosyl)ation targets in different genotoxic stress responses," Mol. Cell, vol. 52, No. 2, 2013, pp. 272-285.

Kleine, et al., "Dynamic subcellular localization of the mono-ADP-ribosyltransferase ARTD10 and interaction with the ubiquitin receptor p62," Cell. Commun Signal, vol. 10, No. 1, 2012, 17 pages.

Leung, et al., "Poly(ADP-ribose) regulates stress responses and microRNA activity in the cytoplasm," Mol. Cell, vol. 42, No. 4, 2011, pp. 489-499.

Masutani and Fujimori, "Poly(ADP-ribosyl)ation in carcinogenesis," Mol. Asp. Med., vol. 34, No. 6, 2013, pp. 1202-1216.

Meyer-Ficca, et al., "Spermatid head elongation with normal nuclear shaping requires ADP-ribosyltransferase PARP11 (ARTD11) in mice," Biol. Reprod., vol. 92, No. 3, 2015, 13 pages.

Mi, et al., "PANTHER version 7: improved phylogenetic trees, orthologs and collaboration with the Gene Ontology Consortium," Nucl. Acids Res., vol. 38, No. Suppl 1, 2010, pp. D204-D210.

Morales, et al., "IGF-1 regulates apoptosis of cardiac myocyte induced by osmotic-stress," Biochem. Biophys. Res. Comm., vol. 270, No. 3, 2000, pp. 1029-1035.

Morgan and Cohen, "A Clickable Aminooxy Probe for Monitoring Cellular ADP-Ribosylation," ACS Chem. Biol., vol. 10, No. 8, 2015, pp. 1778-1784.

Natalizio and Wente, "Postage for the messenger: designating routes for nuclear mRNA export," Trends Cell. Biol., MoL 23, No. 8, 2013, pp. 365-373.

Office Action for U.S. Appl. No. 15/356,040, dated Sep. 17, 2019, Cohen, "Compounds and Methods Used in Assessing Mono-PARP Activity," 7 pages.

Ruf, et al., "Inhibitor and NAD+ binding to poly(ADP-ribose) polymerase as derived from crystal structures and nomology modeling," Biochemistry, vol. 37, No. 11, 1998, pp. 3893-3900.

Schreiber, et al., "Poly(ADP-ribose): novel functions for an old molecule," Nat. Rev. Mol. Cell Biol., vol. 7, No. 7, 2006, pp. 517-528.

Strosznajder, et al., "Poly(ADP-ribose) polymerase: the nuclear target in signal transduction and its role in brain schemia-reperfusion injury," Mol. Neurobiol., vol. 31, No. 1-3, 2005, pp. 149-167.

Supek, et al., "REVIGO summarizes and visualizes long lists of gene ontology terms," PLoS One, vol. 6, No. 7, 2011, 9 pages.

Thomas, et al., "PANTHER: a library of protein families and subfamilies indexed by function," Genome Res., vol. 13, No. 9, 2003, pp. 2129-2141.

Verheugd, et al., "Regulation of NF-?B signalling by the mono-ADP-ribosyltransferase ARTD10," Nature Comm., vol. 1, No. 1683, 2013, 11 pages.

Vyas et al., "Family-wide analysis of poly(ADP-ribose) polymerase activity," Nat. Comm., vol. 5, No. 4426, 2014, 29 pages.

Wacker, et al., "Regulation of chromatin structure and chromatin-dependent transcription by poly(ADP-ribose) polymerase-1: possible targets for drug-based therapies," Subcell. Biochem., vol. 41, 2007, pp. 45-69.

Yan, et al., "Role of Hsp90 in biogenesis of the beta-cell ATP-sensitive potassium channel complex," Mol. Biol. Cell., vol. 21, No. 12, 2010, pp. 1945-1954.

Zhang, et al., "Regulation of poly(ADP-ribose) polymerase-1-dependent gene expression through promoter-directed recruitment of a nuclear NAD+ synthase," J. Biol. Chem., vol. 287, No. 15, 2012, pp. 12405-12416.

Zhang, et al., "Site-specific characterization of the Asp- and Glu-ADP-ribosylated proteome," Nat. Methods, vol. 10, No. 10, 2013, pp. 981-984.

* cited by examiner

FIG. 1A

|  | ceiling | | floor | |
|---|---|---|---|---|
|  | 898  903  907 | | 984  988  992 | |
| PARP1 | DMVSKSANY | --- | LLYNEYIVY | |
| PARP2 | DMSSKSANY | --- | LNYNEFIVY | |
| PARP3 | SENSKSAGY | --- | FSQSEYLIY | |
| PARP4 | DSLSTSIKY | --- | FEDDEFVVY | |
| PARP5-a | ENSSKSNQY | --- | LAYAEYVIY | |
| PARP5-b | ENSSKSNQY | --- | LALAEYVIY | Poly |
| PARP6 | PISSISFGY | --- | KHGNIWVCP | Mono |
| PARP7 | KKASYSHNF | --- | FEPQIFVIF | |
| PARP8 | PMSSISFGY | --- | KHGEIWVVP | |
| PARP10 | RRASLSVQD | --- | CQPSIFVIF | |
| PARP11 | RDAAYSSRF | --- | WNPKIFVVF | |
| PARP12 | RDAAYSHHY | --- | SDPSIFVIF | |
| PARP14 | VNANYSAND | --- | HHPSLFVAF | |
| PARP15 | VDASYSAKD | --- | RSPKLFVVF | |
| PARP16 | SDLSLALIY | --- | IPPKYFVVT | |

FIG. 1B

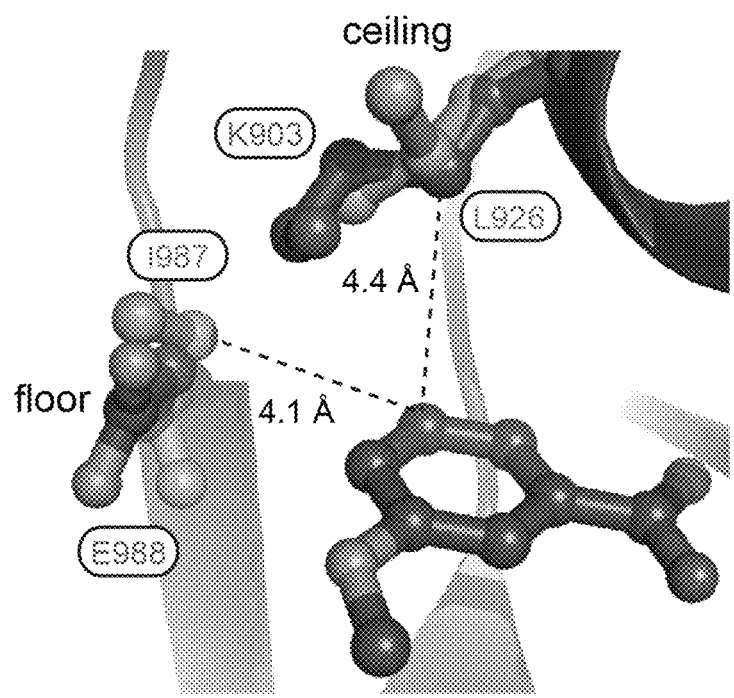

1. "Click" Conjugation
2. In-gel Fluorescence Detection
3. Coomassie Total Protein Stain

FIG. 5

```
PARP6   -EMTQGSYLEIKKQMEKLDPLAHP---LLQWIISSNRSHIVKL------------PL--S
PARP7   -------YPE--------TWVYM-HPSQDFIQVFVSAEDKSYRII-----YNLFRKTVPEFKY
PARP8   -EMTQAPYLEIKKQMDKQDPLAHP---LLQWVISSNRSHIVKL------------PV--N
PARP10  PTLAGQTLKG-------PWNNLE--RLA--------ENTGEFQEVVRAFYDTLDAARSS--I
PARP11  ------IPMPT------HWENV-NFDVPYQLVSLQNQTHEYNEV----ASLFGKTMDR--N
PARP12  ---------IPD-----YWDSSALFDFGFQKITLSSSSEEYQKV----WNLFNRTLPF--Y
PARP14  ---------IPA-----HWSDMK--QQNFCVVELLPSDPEYNTV----ASKFNQTCSB--F
PARP15  --------LPE------HWTDMN--HQLFCMVQLEPGQSEYNTI----KDKFTRTCSS--Y
PARP16  ----------------------VLTIHSAGKAEFEK-------------------------

PARP6   R-LKFMSTSH------QF-LLLSSPFAKEARFRTAKK----LYGSTPAFHGSHIENWHSI
PARP7   RILQILRV-------QNQFLWEKYKRKKEYMNRKMFGRDRIINERALFHGTSQDVVDKI
PARP8   RQLKFMSTPH------QF-LLLSSFFAKESNFRAAKK----LFGSTPAFHGSHIENWHSI
PARP10  RVVRVEKV-------SRPLLQQQYELYPERLLQRCE-----RRFVEQVLYHGTTAPAVFGI
PARP11  RIEKIQRI-------QNLDLWEFFCRKKAQLKKKRG----VPQINEQMLFHGTSSEFVEAI
PARP12  FVQKIERV-------QNLALWEVYQWQKGQMQKQNG--GKAVDERQLFHGTSAIFVDAI
PARP14  RIEKIERI-------QNPDLWNSYQARKKTMDAKNG----QTMNERQLFHGTDAGSVPHV
PARP15  AIEKIERI-------QNAFLWQSYQVKRRQMDIKND----HHNNERLLFHGTDADSVPYV
PARP16  -IQKLTGAPHTPVPAPDFLFEIEYFDPARAKFYETKG----ERDLIYAFHGSRLENFWSI

PARP6   LRNGLVNASYTKLQLHGAAYSKGIYLSPISS SF--GYSQMGKGQHRMPSKDELVQRYNR
PARP7   CRHNFDFKV----CGKHATMFSQGSYFAKKAS SH--NFSKKSSK---------------
PARP8   LRHGLVVASNTRLQLHGAMYGSGIYLSPMSS SF--GYSQMNKKQKVSSKDEPASSSKSS
PARP10  CAHGFNRSF----CGRNATVYGKGVYFARRAS SVQDRYSPPNAD--------------
PARP11  CIHNFDWRI----NGVSGAVFGKGTYFARDAA SS--RFCKDDIKHGNTFQIHG-------
PARP12  CQQNFDWRV----CGVSGTSYGKGSYFARDAA SH--HYSKSDTQ---------------
PARP14  NRNGFNRSY----AGKNAVAYGKGTYFAVRAN SANDTYSRPDAN---------------
PARP15  NQRGFNRSC----AGKNAVSYGKGTYFAVDAS SAKDTYSKPDSN---------------
PARP16  IBNSLNCHLNK------TSLFGESTYLTSDLS AL--IYSPRGRGWQH------------
                                      L926

PARP6   MNTIPQTRSIQSRFLQSRMLNCIALCEVITSKDLQ-----------------------
PARP7   -------------------GVHFMFLAKVLTGRYTMGSHGMRRPPPVNFGSVTSDLYDSCV
PARP8   NASQSQKKGQDSQFLQSRNLKCIALCEVITSPDLH-----------------------
PARP10  -----------GHKAVFVARVLTGDYGQGRRGLRAPPLRGPGH-VLLRYDSAV
PARP11  -------VSLQQRH-LFRTYKSMFLARVLIGDYINGDSKYMBPPSKDG--SYVNLYDSCV
PARP12  ---------------TSTMFLABVLVGEFVRGNASFVRPFAKEG--MSNAFYDSCV
PARP14  -------------GRRSVYYVRVLTGIYTHGNHSLIVPPSKNPQN-PTDLYDTVT
PARP15  -------------GRRHMYVVRVLTGVFTKGRAGLVTPPPKNPHN-PTDLFDSVT
PARP16  --------------SLLGPILSCVAVCEVIDHPDVRCQTKKKDSKEIDR----RRARIKHSE

PARP6   ---KHGL WVCPVSERVCTRFFFVYEDGQVGDAN--INTQDFKIQKEIN
PARP7   DNFFEPQ FVIFNDDQSYPYFVIQYEEVSNTVSI---------------
PARP8   ---KHGE WVVPNTDRVCTRFFFVYEDGQVGDAN--INTQEGGINKEIL
PARP10  DCICQPS FVIFHDTQALPTSLITCEHVPRASPDDPSGLPGKSPDT---
PARP11  DDTWNPR FVVFDANQIYPEYLIDFR-----------------------
PARP12  NSVSDPS FVIFEKHQYPEYVIQYTTSSKFSVTPSILLALGSLFS---
PARP14  DRVBHPS FVAFYDYQAYPEYLITFRK---------------------
PARP15  NNTRSPK FVVFFDNQAYPEYLITFTA---------------------
PARP16  GGDIPPK FVVTNNQLLRVKYLLVYSQKPFRRA--------------
          *
        1987
```

COMPOUNDS AND METHODS USED IN ASSESSING MONO-PARP ACTIVITY

RELATED APPLICATIONS

This application claims priority to U.S. patent application Ser. No. 15/356,040, filed on Nov. 18, 2016; which in turn claims the benefit of the earlier filing date of U.S. Provisional Patent Application 62/258,397, filed Nov. 20, 2015. Both of these prior are incorporated by reference herein in their entirety.

ACKNOWLEDGEMENT OF GOVERNMENT SUPPORT

The disclosed invention was made with the support of the United States government under grant number NS088629 awarded by the National Institute of Neurological Disorders and Stroke (NINDS). The United States government has certain rights to this invention.

FIELD

Generally, the field involves methods of testing the activity of human proteins, more specifically, the field involves identifying targets of and testing inhibitors of mono-PARP enzymes.

BACKGROUND

ADP-ribosylation—the transfer of the ADP-ribose (ADPr) moiety from nicotinamide adenine dinucleotide (NAD+) to amino acids in proteins—is a reversible post-translational modification essential for cellular function in mammals (Hottiger et al, Trends Biochem Sci 35, 208-219 (2010); incorporated by reference herein). The enzymes that catalyze ADP ribosylation, known as poly-ADP-ribose-polymerases (PARPs, of which there are 15 active family members in humans) have been implicated in a number of physiological roles, including gene regulation (Zhang et al, J Biol Chem 287, 12405-12416 (2012); incorporated by reference herein), differentiation (Hu et al, Am J Pathol 182, 71-83 (2013); incorporated by reference herein), and signal transduction (Strosznajder et al, Mol Neurobiol 31, 149-167 (2005); incorporated by reference herein); as well as a number of diseases—notably neurodegeneration (Cosi and Marien, Ann NY Acad Sci 890, 227-239 (1999); incorporated by reference herein) and cancer (Masutani and Fujimori, Mol Asp Med 34, 1202-1216 (2013); incorporated by reference herein). As such, the cellular functions of each PARP family member and their downstream targets have generated significant biological interest. That said, the targets of most PARPs are unknown, which has hampered efforts to delineate their specific roles in cellular processes.

While PARPs were termed polymerases based on their homology to the catalytic domain of the founding member PARP1 (a verified polymerase), most PARP family members (PARPs 6-8, 10-12, and 14-16) catalyze mono-ADP-ribosylation (MARylation) and not poly-ADP-ribosylation (PARylation) as previously thought (Vyas et al, Nat Comm 5, 4426 (2014); incorporated by reference herein). The PARPs that catalyze MARylation, referred to herein as mono-PARPs, are not understood in nearly as much detail as the PARPs that catalyze PARylation, referred to herein as poly-PARPs. This is due, in part, to the lack of chemical tools to study MARylation in the cell. PARylated proteins can be detected using specific antibodies (e.g. 10H) (Affar et al, Anal Biochem 259, 280-283 (1998); incorporated by reference herein). No such antibodies exist for detecting MARylated proteins. Similarly, PARylated and MARylated proteins can be enriched using different protein domains (e.g. macro) (Jungmichel et al, Mol Cell 52, 272-285 (2013); incorporated by reference herein;) or the modification of the ADPr adduct with chemical tags (e.g. biotin, boronate resin) (Jiang et al, J Am Chem Soc 132, 9363-9372 (2010) and Zhang et al, Nat Methods 10, 981-984 (2013); both of which are incorporated by reference herein) followed by protein identification by liquid-chromatography and tandem mass spectrometry (LC-MS/MS). But, none of these methods are able to distinguish between MARylation and PARylation and, most importantly, they cannot determine which mono-PARP is responsible for a given modification. As a result, advances in mono-PARP biology have been painstaking, requiring the identification of targets through traditional molecular biology approaches (i.e. deletion and overexpression assays with an individual mono-PARP, in vitro MARylation assays with radioactive or biotinylated NAD+, etc.). Complicating matters further, the mono-PARP family members are known to form complexes with each other in the cell and could be playing semiredundant roles in signal transduction (Leung et al, Mol Cell 42, 489-499 (2011); incorporated by reference herein). To push this field forward, new strategies are needed to link a given mono-PARP to its direct protein targets as well as screens for inhibitors of mono-PARPs.

SUMMARY

Poly-ADP-ribose-polymerases (PARP1-16) have emerged as major downstream effectors of NAD+ signaling in the cell. Most PARPs (PARP6-8, 10-12, and 14-16) catalyze the transfer of a single unit of ADP-ribose from NAD+ to amino acids in target proteins, a process known as mono-ADP-ribosylation (MARylation). Progress in understanding the cellular functions of MARylation has been limited by the inability to identify the direct targets for individual mono-PARPs. Herein are disclosed engineered mono-PARPs to use an NAD+ analogue that is orthogonal to wild-type PARPs. The MARylomes of PARP10 and PARP11 were analyzed, identifying isoform-specific targets and revealing a potential role for PARP11 in nuclear pore complex biology. It is further disclosed that PARP11 targeting is dependent on both its regulatory and catalytic domains, which has important implications for how PARPs recognize their targets. The chemical genetic strategy disclosed herein will be generalizable to all mono-PARP family members based on the similarity of the mono-PARP catalytic domains.

Disclosed herein are small molecule compounds (SMCs) of formula:

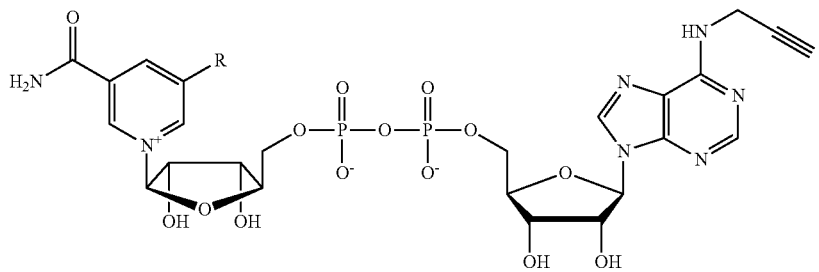

wherein R is aryl or alkyl provided that R is not ethyl. Such SMCs can act as PARP substrates.

Further disclosed are recombinant proteins including a mutant catalytic domain of PARP6, PARP7, PARP8, PARP10, PARP11, PARP12, PARP14, PARP15, and PARP16, with a mutation from leucine, isoleucine or tyrosine in the position as indicated by Xaa in SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 to a glycine, alanine, serine, cysteine, valine, threonine, or proline, wherein the remainder of the polypeptide is at least 90% identical to SEQ ID NO: 1 SEQ ID NO: 2, SEQ ID NO: 3, SEQ ID NO: 4, SEQ ID NO: 5, SEQ ID NO: 6, SEQ ID NO: 7, or SEQ ID NO: 8 and wherein the polypeptide catalyzes the addition of SMCs (e.g., 5-Bn-6-a-NAD+) to a PARP protein target. Further examples of these polypeptides include SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24.

Also disclosed is a method of identifying a protein target of a mono-PARP. This method involves contacting a SMC of formula:

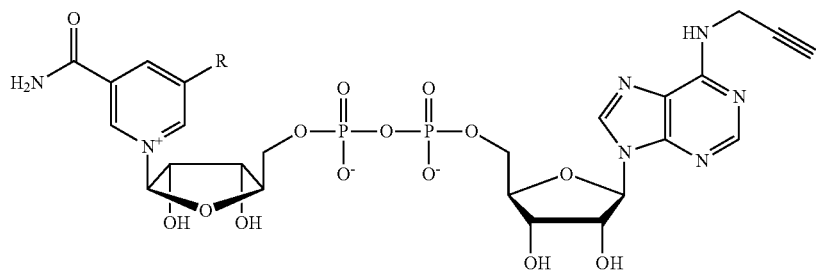

wherein R is alkyl or aryl; with one or more of the disclosed recombinant proteins including a mutant catalytic domain of a mono-PARP. The contacting for this method occurs within a cell. The cell is subjected to conditions that result in the recombinant protein catalyzing a covalent attachment of the SMC with one or more cellular protein targets. The cellular protein to which the SMC is covalently attached is identified as a protein target of the mono-PARP.

Still further disclosed are screening methods that can be used to identify and select test compounds as inhibitors of a mono-PARP. Such methods involve contacting a SMC of formula:

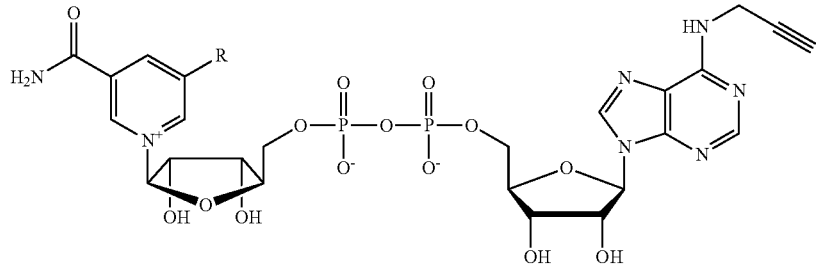

wherein R is alkyl or aryl; with (i) one or more of the disclosed recombinant proteins including a mutant catalytic domain of a mono-PARP, (ii) one or more test compounds, and (iii) one or more known protein targets of the mono-PARP(s) from which the catalytic domain was derived. The contacting occurs within a mixture, the mixture is subjected to conditions that are known to result in the covalent attachment of the SMC to the known protein targets via mono-PARP activity, at least in the absence of the one or more test compounds. A test compound that inhibits the ability of the recombinant mono-PARP protein to catalyze the reaction that binds the SMC to the known protein target is identified as an inhibitor of the mono-PARP.

The disclosed methods can be used to identify direct targets of any member of the mono-PARP subclass.

The disclosed methods can be used to identify PARP complexes where multiple PARP family members are responsible for a given target modification (Leung et al, 2011 supra).

The disclosed methods can be used to decouple the role for a given PARP family member in signaling pathways, even when specific function is unknown.

The disclosed methods can be used to assign PARylated and MARylated protein targets to each individual PARP family-member with a specific ADP-ribose transfer.

The disclosed methods can be used to generate a database of mono-PARP MARylation targets that can be used immediately to examine the biological role of these mono-PARPs in the cell.

BRIEF DESCRIPTION OF THE DRAWINGS

FIGS. 1A-1E. FIG. 1A is a sequence alignment of the nicotinamide binding site of the poly-PARPs (above dashed line) and the mono-PARPs (below). The sequences are reflected in the Sequence Listing as follows: PARP1 (SEQ ID NOS: 36 and 37), PARP2 (SEQ ID NOS: 38 and 39), PARP3 (SEQ ID NOS: 40 and 41), PARP4 (SEQ ID NOS: 42 and 43), PARP5-a (SEQ ID NOS: 44 and 45), PARP5-b (SEQ ID NOS: 44 and 46), PARP6 (SEQ ID NOS: 47 and 48), PARP7 (SEQ ID NOS: 49 and 50), PARP8 (SEQ ID NOS: 51 and 52), PARP10 (SEQ ID NOS: 53 and 54), PARP11 (SEQ ID NOS: 55 and 56), PARP12 (SEQ ID NOS: 57 and 58), PARP14 (SEQ ID NOS: 59 and 60), PARP15 (SEQ ID NOS: 61 and 62), and PARP16 (SEQ ID NOS: 63 and 64 FIG. 1B is an overlay of the crystal structures of PARP1cat (dark grey) (PDB ID: 3PAX, Ruf et al, Biochemistry 37, 3893-3900 (1998); incorporated by reference herein) and PARP10cat (light grey) (PDB ID: 3HKV) showing the nicotinamide binding sites. The distance between the key amino acids identified in PARP10, L926 and I987, and the C-5 position of 3-methoxybenzamide are indicated. FIG. 1C is a schematic of one aspect of the disclosed methods: PARP10 variants were incubated with the PARP10 target, SRPK2, in the presence of each individual NAD+ analogue. Modified SRPK2 was subjected to "click" conjugation with a fluorogenic probe and total MARylation was observed using in-gel detection. FIG. 1D is an image of an immunoblot plus Coomassie gel (load control) summarizing the results from an orthogonal SRPK2 MARylation screen. Engineered PARP10 variants are listed above the gels. C-5 substitutions on the nicotinamide ring are indicated. For each modified NAD+ analogue tested the same gel was first fluorescently imaged to detect SRPK2 MARylation (top gel, gray) and then stained to detect total SRPK2 (bottom gel, light grey). FIG. 1E is a heat map depicting the normalized global MARylation efficiency for the engineered pairs tested in FIG. 1D.

FIG. 2A is an immunoblot of lysates labeled by I987G-PARP10 or I313G-PARP11 in the presence of 5-Bn-6-a-NAD+. HEK 293T cells were transfected with either WT— or IG-PARP10 or -PARP11 and the resulting lysate was incubated for 2 hours in the presence of 5-Bn-6-a-NAD+. MARylation of direct protein targets was observed using streptavidin-HRP (Biotin). The faint bands in the WT-PARP lanes correspond to endogenous biotinylated proteins. Expression of each PARP was confirmed via immunoblot detection of GFP. FIG. 2B is a Venn diagram comparing the I987G-PARP10 targets identified via LC-MS/MS in either HEK 293T or HeLa cells. FIG. 2C is a set of two plots showing the observed distribution functions for the I987G-PARP10 targets identified via LC-MS/MS in either HEK 293T (top) or HeLa (bottom) cells. The distributions for the total protein pool (total) as well as the subset of proteins that were identified in both HEK 293T and HeLa (shared) are indicated. The shared targets identified in HEK 293T cells display significantly elevated peptide counts per identified protein as compared to the total target pool (p<0.05, non-parametric Mann-Whitney U test). The shared targets identified in HeLa cells also display elevated peptide counts per protein, but the difference compared to the total target pool is not significant. FIG. 2D is an image of an immunoblot of the LC-MS/MS identified PARP10 targets (GFP-PARP10, XPO5, WRIP1) following NeutrAvidin enrichment. MARylation levels were determined using streptavidin-HRP (Biotin). Differences in labeling efficiency between HEK 293T and HeLa lysate required separate immunoblot exposures.

FIG. 3A is an image of an immunoblot of Lysate labeling by I987G-PARP10 or I313G-PARP11 in the presence of 5-Bn-6-a-NAD+. HEK 293T cells were transfected with either WT— or I987G-PARP10 or I313G-PARP11 and the resulting lysate was incubated for 2 hours in the presence of 5-Bn-6-a-NAD+. MARylation of direct protein targets was observed using streptavidin-HRP (Biotin). The faint bands in the WT-PARP lanes correspond to endogenous biotinylated proteins. Expression of each PARP was confirmed via immunoblot detection of GFP. FIG. 3B is a Venn diagram comparing the total I987G-PARP10 target pool with both the current I313G-PARP11 and the previously identified KA-PARP1 and KA-PARP2 (Carter-O'Connell et al., 2014) target pools. The protein counts in bold represent the protein targets identified in both LC-MS/MS I987G-PARP10 replicates while the counts in parentheses represent targets identified in at least one replicate. I987G-PARP10 specific targets are shown in the gray circle. FIG. 3C is a Venn diagram comparing the total I313G-PARP11 target pool with both the current I987G-PARP10 and the previously identified KA-PARP1 and KA-PARP2 (Carter-O'Connell et al., 2014) target pools. The protein counts in bold represent the protein targets identified in both LC-MS/MS I313G-PARP11 replicates while the counts in parentheses represent targets identified in at least one replicate. I313G-PARP11 specific targets are shown in the gray circle. FIG. 3D is a set of two circle plots depicting enriched GO terms attached to the I987G-PARP10 (left,) or I313G-PARP11 (right, yellow) specific LC-MS/MS identified targets. GO term enrichment was performed using the PANTHER toolkit. Significantly enriched GO terms (p<0.05) were condensed using Revigo and similar terms were plotted based on semantic similarity. Select groups of terms are indicated. Circle radii are scaled proportionally to the − log 10(p-value). The I313G-PARP11 specific proteins associated with RNA transport are listed.

FIG. 4A is a schematic showing the domain architecture of PARP11, PARP10, and the chimeric protein (Chimera) created by fusing the PARP11 n-terminus to the PARP10cat domain. FIG. 4B is a pie chart representing the total MARylated protein targets identified via LC-MS/MS for the chimeric protein. Shared protein targets are indicated by the protein schematics depicted in FIG. 4A. Shared protein targets were identified based on their presence in at least one of the I987G-PARP10 or I313G-PARP11 LC-MS/MS replicates. FIG. 4C is an image of an immunoblot of selected LC-MS/MS identified PARP targets (GFP-PARP, UBE3C, XPO5, NXF1, NUP98, NAGK, WRIP1) following NeutrAvidin enrichment. Overall MARylation levels were determined using streptavidin-HRP (Biotin). PARP10-specific, PARP11-specific, PARP11-WWE dependent and shared chimera targets are indicated to the left. Reference molecular weight ladder shown in kDa.

FIG. 5 is a structure-based sequence alignment of the mono-PARPcat Domains: The aligned primary sequence of the catalytic domains for PARPs 6-8, 10-12, and 14-16 are presented. Secondary structural elements are designated above the alignments (spiral: α-helix, arrow: β-sheet) and the variable d-loop element is indicated. Red asterisks mark the H-Y-I/L/Y triad. The residues targeted for mutagenesis in the present study are highlighted and their position (PARP10 numbering) is noted. The sequences in FIG. 5 are shown in the Sequence Listing as SEQ ID NOs: 27-35.

FIG. 6A is an image of results from orthogonal MARylation of SRPK2 by LG-PARP15 and 5-Bn-6-a-NAD+. WT—and SEQ ID NO: 23 (L659G-PARP15) are indicated above the gel and the non-substituted 6-a-NAD+ and 5-Bn-6-a-NAD+ probes are listed to the right of the gel. For each modified NAD+ analogue tested the same gel was first fluorescently imaged to detect SRPK2 MARylation (top gel, gray) and then stained to detect total SRPK2 (bottom gel, blue). FIG. 6B is a bar graph quantifying the results shown in FIG. 6A.

FIG. 9A is an image of an Immunoblot detection of the input fractions prior to the enrichment shown in FIG. 2D. Overall MARylation levels were determined using streptavidin-HRP (Biotin). Differences in labeling efficiency between HEK 293T and HeLa lysate required separate immunoblot exposures. FIG. 9B is an image of an Immunoblot detection of the input fractions prior to the enrichment shown in FIG. 4C. Overall MARylation levels were determined using streptavidin-HRP (Biotin). Differences in labeling efficiency between HEK 293T and HeLa lysate required separate immunoblot exposures. Reference molecular weight ladder shown in kDa.

SEQUENCE LISTING

Figure 1C:
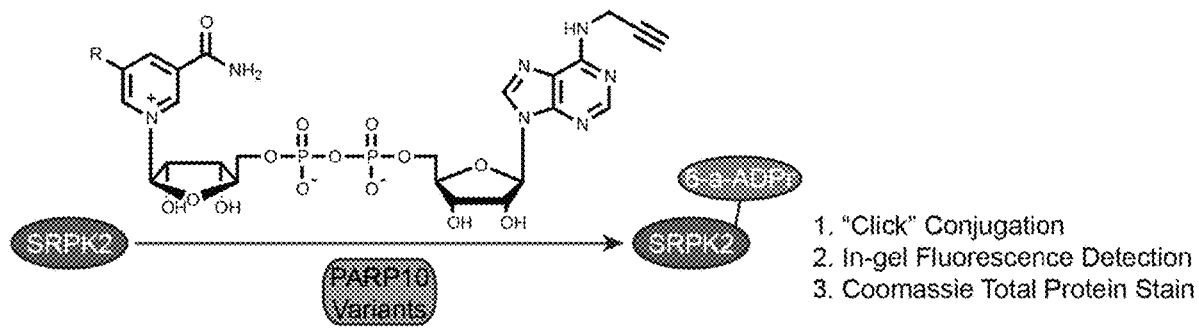

The nucleic acid and/or amino acid sequences described herein are shown using standard letter abbreviations, as defined in 37 C.F.R. § 1.822. Only one strand of each nucleic acid sequence is shown, but the complementary strand is understood as included in embodiments where it would be appropriate. A computer readable text file, entitled "2PT5221" created on or about Jun. 17, 2022, with a file size of 60 KB, contains the sequence listing for this application and is hereby incorporated by reference in its entirety.

SEQ ID NO: 1 is an example of a *Homo sapiens* PARP6 catalytic domain with a mutation indicated by Xaa at position 113 of the sequence.

SEQ ID NO: 2 is an example of a *Homo sapiens* PARP7 catalytic domain with a mutation indicated by Xaa at position 166 of the sequence.

SEQ ID NO: 3 is an example of a *Homo sapiens* PARP10 catalytic domain with a mutation indicated by Xaa at position 168 of the sequence.

SEQ ID NO: 4 is an example of a *Homo sapiens* PARP11 catalytic domain with a mutation indicated by Xaa at position 120 of the sequence.

SEQ ID NO: 5 is an example of a *Homo sapiens* PARP12 catalytic domain with a mutation indicated by Xaa at position 164 of the sequence.

SEQ ID NO: 6 is an example of a *Homo sapiens* PARP14 catalytic domain with a mutation indicated by Xaa at position 165 of the sequence.

SEQ ID NO: 7 is an example of a *Homo sapiens* PARP15 catalytic domain with a mutation indicated by Xaa at position 161 of the sequence.

SEQ ID NO: 8 is an example of a *Homo sapiens* PARP16 catalytic domain with a mutation indicated by Xaa at position 160 of the sequence.

SEQ ID NO: 9 is an example of a *Homo sapiens* PARP6 catalytic domain with a G residue at position 113 of the sequence.

SEQ ID NO: 10 is an example of a *Homo sapiens* PARP6 catalytic domain with an A residue at position 113 of the sequence.

SEQ ID NO: 11 is an example of a *Homo sapiens* PARP7 catalytic domain with a G residue at position 166 of the sequence.

SEQ ID NO: 12 is an example of a *Homo sapiens* PARP7 catalytic domain with an A residue at position 166 of the sequence.

SEQ ID NO: 13 is an example of a *Homo sapiens* PARP8 catalytic domain with a G at position 112 of the sequence.

SEQ ID NO: 14 is an example of a *Homo sapiens* PARP8 catalytic domain with an A at position 112 of the sequence.

SEQ ID NO: 15 is an example of a *Homo sapiens* PARP10 catalytic domain with a G residue at position 168 of the sequence.

SEQ ID NO: 16 is an example of a *Homo sapiens* PARP10 catalytic domain with an A residue at position 168 of the sequence.

SEQ ID NO: 17 is an example of a *Homo sapiens* PARP11 catalytic domain with a G residue at position 120 of the sequence.

SEQ ID NO: 18 is an example of a *Homo sapiens* PARP11 catalytic domain with an A residue at position 120 of the sequence.

SEQ ID NO: 19 is an example of a *Homo sapiens* PARP12 catalytic domain with a G residue at position 164 of the sequence.

SEQ ID NO: 20 is an example of a *Homo sapiens* PARP12 catalytic domain with an A residue at position 164 of the sequence.

SEQ ID NO: 21 is an example of a *Homo sapiens* PARP14 catalytic domain with a G residue at position 165 of the sequence.

SEQ ID NO: 22 is an example of a *Homo sapiens* PARP14 catalytic domain with an A residue at position 165 of the sequence.

SEQ ID NO: 23 is an example of a *Homo sapiens* PARP15 catalytic domain with a G residue at position 161 of the sequence.

SEQ ID NO: 24 is an example of a *Homo sapiens* PARP15 catalytic domain with an A residue at position 161 of the sequence.

SEQ ID NO: 25 is an example of a *Homo sapiens* PARP16 catalytic domain with a G residue at position 160 of the sequence.

SEQ ID NO: 26 is an example of a *Homo sapiens* PARP16 catalytic domain with an A residue at position 160 of the sequence.

SEQ ID NOs: 27-35 are the PARP sub-sequences aligned in FIG. 5, in the following order: PARP6, PARP7, PARP8, PARP10, PARP11, PARP12, PARP14, PARP15, and PARP16.

SEQ ID NOs: 36-64 are the PARP sub-sequences aligned in FIG. 1A, as follows: PARP1 (SEQ ID NOs: 36 and 37), PARP2 (SEQ ID NOs: 38 and 39), PARP3 (SEQ ID NOs: 40 and 41), PARP4 (SEQ ID NOs: 42 and 43), PARP5-a (SEQ ID NOs: 44 and 45), PARP5-b (SEQ ID NOs: 44 and 46), PARP6 (SEQ ID NOs: 47 and 48), PARP7 (SEQ ID NOs: 49 and 50), PARP8 (SEQ ID NOs: 51 and 52), PARP10 (SEQ ID NOs: 53 and 54), PARP11 (SEQ ID NOs: 55 and 56), PARP12 (SEQ ID NOs: 57 and 58), PARP14 (SEQ ID NOs: 59 and 60), PARP15 (SEQ ID NOs: 61 and 62), and PARP16 (SEQ ID NOs: 63 and 64).

DETAILED DESCRIPTION

Disclosed herein is method of labeling specific targets of a single engineered mono-PARP with a clickable NAD+ analogue including a benzyl substituent at the C-5 position of the nicotinamide ring and an alkyne at the N-6 position of the adenosine ring (5-Bn-6-a-NAD+). When combined with LC-MS/MS analysis, a set of 140 preferred PARP10-specific targets involved in a wide-array of biological processes was identified. Also identified was a set of 21 preferred PARP11-specific targets that are primarily involved in nuclear pore complex biology (Natalizio B J and Wente S R, Trends Cell Biol 23, 365-373 (2013); incorporated by reference herein). This represents the first identification of cellular PARP11 targets and implicates PARP11 in a previously uncharacterized biological role. The disclosed methods were also used to explore the requirements for target recognition at both the NAD+ active site and the modular n-terminal regulatory domains of PARPs 10 and 11. Provided herein is the first evidence of the structurally conserved PARPcat domains and that the non-conserved modular n-terminal regulator domains in the mono-PARP family play specific, and necessary, roles in precise target recognition.

Terms:

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist essentially of, or consist of." The transition term "comprise" or "comprises" means includes, but is not limited to, and allows for the inclusion of unspecified elements, steps, ingredients, or components, even in major amounts. The transitional phrase "consisting essentially of" limits the scope of the embodiment to the specified elements, steps, ingredients or components and to those that do not materially affect the embodiment. As used herein, a material effect would cause a statistically-significant reduction in an embodiment's ability to identify (i) a mono-PARP protein target; or (ii) a test compound that is a mono-PARP inhibitor. The transitional phrase "consisting of" excludes any element, step, ingredient or component not specified.

In addition, the materials, methods, and examples are illustrative only and not intended to be limiting. In order to facilitate review of the various embodiments of the disclosure, the following explanations of specific terms are provided:

Alkyl: a branched or unbranched saturated hydrocarbon group, such as methyl, ethyl, n-propyl, isopropyl, n-butyl, isobutyl, t-butyl, pentyl, hexyl, heptyl, octyl, nonyl, decyl, tetradecyl, hexadecyl, eicosyl, tetracosyl and the like. A lower alkyl group is a saturated branched or unbranched hydrocarbon having from 1 to 6 carbon atoms (C1-6 alkyl). The term alkyl also includes cycloalkyls. Alkyl also includes substituted alkyls which are alkyl groups wherein one or more hydrogen atoms are replaced with a substituent such as alkyl, alkynyl, alkenyl, aryl, halide, nitro, amino, ester, ether, ketone, aldehyde, hydroxyl, carboxyl, cyano, amido, haloalkyl, haloalkoxy, or alkoxy. The term alkyl also includes heteroalkyls. A heteroalkyl contains at least one heteroatom such as nitrogen, oxygen, sulfur, or phosphorus replacing one or more of the carbons. Substituted heteroalkyls are also encompassed by the term alkyl.

Antagonist: An antagonist is an agent, such as a small molecule or protein that binds to a protein and prevents, stops, or reduces (to a statistically significant degree) the protein from producing a particular biological effect. An antagonist can be a naturally occurring or artificially synthesized compound. For example, a mono-PARP antagonist is a compound that inhibits natural activity of a mono-PARP. An antagonist can also be called an inhibitor and the terms can be used interchangeably.

Aryl: any carbon-based aromatic group including benzene, naphthalene, and phenyl. The term aryl also includes substituted aryls in which one or more of the hydrogens is substituted with one or more groups including alkyl, alkynyl, alkenyl, aryl, halide, nitro, amino, ester, ether, ketone, aldehyde, hydroxy, carboxylic acid, cyano, amido, haloalkyl, haloalkoxy, or alkoxy. The term aryl also includes heteroaryls in which one or more of the carbons is replaced by a heteroatom. Examples of heteroatoms include nitrogen, oxygen, sulfur, and phosphorous. Substituted heteroaryls are also encompassed by the term aryl.

Contacting: Placement under conditions in which direct physical association occurs, including contacting of a solid with a solid, a liquid with a liquid, a liquid with a solid, or either a liquid or a solid with a cell or tissue, whether in vitro or in vivo. Contacting can occur in vitro with isolated cells or tissue or in vivo by administering to a subject.

Conservative amino acid substitution: A substitution of an amino acid residue for another amino acid residue having similar biochemical properties. "Conservative" amino acid substitutions are those substitutions that do not substantially affect or decrease an activity of a polypeptide such as a mono-PARP catalytic domain, WWE domain, or zinc finger domain. A polypeptide can include one or more conservative substitutions up to and including 1-10 total conservative substitutions, 1% conservative substitutions, 5% conservative substitutions, 10% conservative substitutions, 15% conservative substitutions, 20% conservative substitutions, 25% conservative substitutions, 30% or more conservative substitutions, or any intervening value. Specific examples of conservative substitutions include the following:

| Original Amino Acid | Conservative Substitution |
|---|---|
| Ala | Ser |
| Arg | Lys |
| Asn | Gln, His |
| Asp | Glu |
| Gln | Asn |
| Cys | Ser |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

While examples of polypeptide sequences are provided in the amino acid sequences filed with this application, not all variants of polypeptide sequences with all possible combinations of conservative amino acid substitutions encompassed by the disclosure are provided in the sequence listing. This table can be used in combination with the sequence listing to provide explicit examples of polypeptide sequences encompassed by the disclosure.

Control: A reference standard. A control can be a test compound that is known to be an antagonist of a mono-PARP (positive control). A control can also be a test compound known not to act as an antagonist of a mono-PARP, such as the vehicle in which the test compound is provided, otherwise lacking the test compound (negative control).

Cycloalkyl: a non-aromatic carbon-based ring composed of at least three carbon atoms. Examples of cycloalkyl groups include cyclopropyl, cyclobutyl, cyclopentyl, and cyclohexyl. Cycloalkyls also encompass substituted cycloalkyls and heterocycloalkyls where at least one of the carbon atoms is replaced with a heteroatom such as nitrogen, sulfur or phosphorus. A heterocycloalkyl wherein one or more of the carbons is replaced with nitrogen is also termed a cycloalkylamino herein. The term also includes substituted heterocycloalkyls.

Derivative: a compound or portion of a compound that is derived from or is theoretically derivable from a parent compound. Within the current disclosure, a derivative exhibits a substantially similar biological effect in the methods disclosed and claimed herein.

Domain: A domain of a polypeptide or protein may be any part of a protein that exhibits a particular defined structure and/or mediates a particular protein function. An example of a domain is the catalytic domain of a mono-PARP.

Heterocycle: A chemical group that includes both heteroaryls and heterocycloalkyls. Heterocycles may be monocyclic or polycyclic rings. Exemplary heterocycles include azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups. The term also includes substituted heterocycles, including substituted forms of all the species above.

Label: A label may be any substance capable of aiding a machine, detector, sensor, device, column, or enhanced or unenhanced human eye in differentiating a labeled composition from an unlabeled composition. Labels may be used for any of a number of purposes and one skilled in the art will understand how to match the proper label with the proper purpose. Examples of uses of labels include purification of biomolecules, identification of biomolecules, detection of the presence of biomolecules, detection of protein folding, and localization of biomolecules within a cell, tissue, or organism. Examples of labels include: radioactive isotopes or chelates thereof; dyes (fluorescent or nonfluorescent), stains, enzymes, nonradioactive metals, magnets, protein tags, any antibody epitope, any specific example of any of these; any combination between any of these, or any label now known or yet to be disclosed. A label may be covalently attached to a biomolecule or bound through hydrogen bonding, Van Der Waals or other forces. A label may be covalently or otherwise bound to the N-terminus, the C-terminus or any amino acid of a polypeptide or the 5' end, the 3' end or any nucleic acid residue in the case of a polynucleotide.

One particular example of a label is a protein tag. A protein tag includes a sequence of one or more amino acids that may be used as a label as discussed above, particularly for use in protein purification. In some examples, the protein tag is covalently bound to the polypeptide. It may be covalently bound to the N-terminal amino acid of a polypeptide, the C-terminal amino acid of a polypeptide or any other amino acid of the polypeptide. Often, the protein tag is encoded by a polynucleotide sequence that is immediately 5' of a nucleic acid sequence coding for the polypeptide such that the protein tag is in the same reading frame as the nucleic acid sequence encoding the polypeptide. Protein tags may be used for all of the same purposes as labels listed above and are well known in the art. Examples of protein tags include chitin binding protein (CBP), maltose binding protein (MBP), glutathione-S-transferase (GST), poly-histidine (His), thioredoxin (TRX), FLAG®, V5, c-Myc, HA-tag, and so forth.

A His-tag facilitates purification and binding to on metal matrices, including nickel matrices, including nickel matrices bound to solid substrates such as agarose plates or beads, glass plates or beads, or polystyrene or other plastic plates or beads. Other protein tags include BCCP, calmodulin, Nus, Thioredoxin, Streptavidin, SBP, and Ty, or any other combination of one or more amino acids that can work as a label described above.

Another particular example of a label is biotin. Biotin is a natural compound that tightly binds proteins such as avidin or streptavidin. A compound labeled with biotin is said to be 'biotinylated'. Biotinylated compounds can be detected with avidin or streptavidin when that avidin or streptavidin is conjugated another label such as a fluorescent, enzymatic, radioactive or other label.

Mass spectrometry: A method wherein, a sample is analyzed by generating gas phase ions from the sample, which are then separated according to their mass-to-charge ratio (m/z) and detected. Methods of generating gas phase ions from a sample include electrospray ionization (ESI), laser-spray ionization (LSI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), Fourier-transform ion cyclotron resonance (FT-ICR) analyzers, and combinations thereof (for example, a quadrupole-time-of-flight analyzer, or Q-TOF analyzer). Prior to separation, the sample may be subjected to one or more dimensions of chromatographic separation, for example, one or more dimensions of liquid or size exclusion chromatography or gel-electrophoretic separation.

Mutation: A mutation can be any difference in the sequence of a biomolecule relative to a reference or consensus sequence of that biomolecule. A mutation can be observed in a nucleic acid sequence or a protein sequence. Such a reference or consensus sequence may be referred to as "wild type". For example, a mutation such as a mutation from isoleucine at position 987 to a glycine in the catalytic domain of PARP10 is a mutation relative to the PARP10 consensus sequence. Other mutations can result in conservative amino acid substitutions.

NAD: An abbreviation of nicotinamide adenine dinucleotide. The oxidized form is referred to as NAD+. The reduced form is referred to as NADH. NAD has a number of physiological roles including as an enzyme cofactor, as an oxidizing (NAD+) or reducing (NADH) agent, and as a signaling molecule. NAD (without a plus-sign) is a common term that includes both the oxidized and reduced forms of the NAD molecule. NAD has important roles in transcription, DNA repair, cellular metabolism, and apoptosis and both NAD levels and oxidation state are considered to be important mechanisms in cancer growth and development (Chiarugi et al, Nat Rev Cancer 12, 741-752 (2012); incorporated by reference herein).

Nucleic acid or nucleic acid sequence: a polymer of ribonucleic acid (RNA) or deoxyribonucleic acid (DNA). The term can be used interchangeably with the term 'polynucleotide.' A nucleic acid is made up of four bases; adenine, cytosine, guanine, and thymine/uracil (uracil is used in RNA). A coding sequence from a nucleic acid is indicative of the sequence of the protein encoded by the nucleic acid.

Operably Linked: A first nucleic acid sequence is operably linked with a second nucleic acid sequence when the first nucleic acid sequence is placed in such a way that it has an effect upon the second nucleic acid sequence. For instance, a promoter is operably linked to a coding sequence if the promoter affects the transcription or expression of the coding sequence. Operably linked DNA sequences may be contiguous, or they may operate at a distance.

Polypeptide: Any chain of amino acids, regardless of length or posttranslational modification (such as glycosylation, methylation, ubiquitination, phosphorylation, or the like). Herein as well as in the art, the term 'polypeptide' is used interchangeably with peptide or protein, and is used to refer to a polymer of amino acid residues. The term 'residue' can be used to refer to an amino acid or amino acid mimetic incorporated in a polypeptide by an amide bond or amide bond mimetic. Polypeptide sequences are generally written with the N-terminal amino acid on the left and the C-terminal amino acid to the right of the sequence.

Promoter: A promoter may be any of a number of nucleic acid control sequences that directs transcription of a nucleic acid. Typically, a eukaryotic promoter includes necessary nucleic acid sequences near the start site of transcription, such as, in the case of a polymerase II type promoter, a TATA element or any other specific DNA sequence that is recognized by one or more transcription factors. Expression by a promoter may be further modulated by enhancer or repressor elements. Numerous examples of promoters are available and well known to those of skill in the art. A nucleic acid including a promoter operably linked to a nucleic acid sequence that codes for a particular polypeptide can be termed an expression vector.

Purification: Purification of a polypeptide or molecular complex may be achieved by any method now known or yet to be disclosed. In some examples, purification is achieved by contacting the complex with a reagent that binds to a component of the complex to the exclusion of other components.

Recombinant: A recombinant nucleic acid or polypeptide has a sequence that is not naturally occurring or has a sequence that is made by an artificial combination of two or more naturally occurring sequences. This artificial combination is often accomplished by chemical synthesis or, more commonly, by the artificial manipulation of isolated segments of nucleic acids, e.g., by genetic engineering techniques. A recombinant polypeptide can refer to a polypeptide that has been made using recombinant nucleic acids, including recombinant nucleic acids transferred to a host organism that is not the natural source of the polypeptide.

Sequence homology: Sequence homology between two or more nucleic acid sequences or two or more amino acid sequences, may be expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75). For comparisons of amino acid sequences of greater than 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). In addition, a manual alignment can be performed. Proteins with even greater similarity will show increasing percentage identities when assessed by this method, such as at least 50%, 60%, 70%, 75%, 80%, 85%, 90%, 95%, 98%, 99%, or 100% sequence identity.

When aligning short peptides (fewer than around 30 amino acids), the alignment is to be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 50%, 60%, 70%, 75%, 80%, 85%, 90%, 95%, 98%, or 99% sequence identity to a protein. When less than the entire sequence is being compared for sequence identity, including a comparison of, for example, a mono-PARP catalytic domain, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

A pair of proteins or nucleic acids with 50%, 60%, 70%, 75%, 80%, 85%, 90%, 95%, 98%, or 99% identity to one another can be termed 'homologs,' particularly if they perform the same function as one another, even more particularly if they perform the same function to substantially the same degree, and still more particularly if they perform the same function substantially equivalently. One of skill in the art in light of this disclosure, particularly in light of the Examples below, would be able to determine without undue experimentation whether or not a given protein or nucleic acid sequence with 50%, 60%, 70%, 75%, 80%, 85%, 90%, 95%, 98%, or 99% identity to the sequences listed herein is a homolog to the sequences listed herein. Homologs need not be the same length as the biological molecules listed herein and may include truncations (fewer amino acids or nucleotides) or extensions (more amino acids or nucleotides) than the biological molecules listed herein.

Test Compound: A test compound can be any compound that is suspected of or might effect mono-PARP activity. Examples of test compounds include small molecules, proteins, peptides, or other potential therapeutic compounds. A test compound can also be a compound known to inhibit mono-PARP activity that is used as a positive control. A test compound can also be a compound known not to affect mono-PARP activity that is used as a negative control.

Small Molecule Compounds (SMCs): Disclosed Herein are SMCs of Formula:

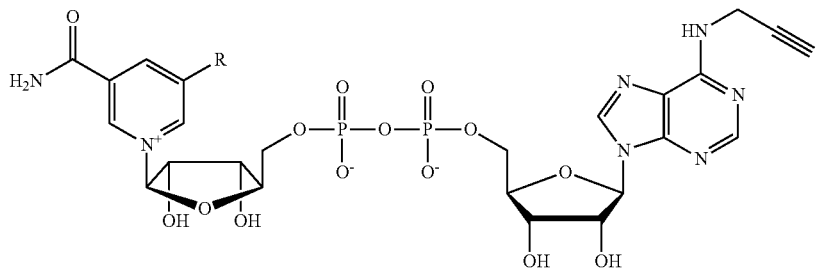

wherein R is selected from alkyl and aryl. In some examples, this is provided that R is not ethyl. Aside from that provision, R can be any alkyl including any straight chain alkyl (such as methyl and propyl) any branched alkyl (such is isobutyl), or cycloalkyl. R can also be any aryl including benzyl, any substituted aryl, or any heteroaryl. Such SMCs can be provided in a vehicle such as a buffer or other appropriate solution.

The disclosed SMCs can be used as substrates of mutant mono-PARP catalytic domains as described below. The SMCs will not work as substrates of wild-type mono-PARP catalytic domains. In addition, a label such as a fluorescent compound, biotin, protein tag, or other label can be conjugated to the SMCs.

Polypeptide Compositions: Further disclosed are recombinant polypeptides that include a mono-PARP catalytic domain. The mono-PARP catalytic domain can be selected from that of PARP6, PARP7, PARP8, PARP10, PARP11, PARP12, PARP14, PARP15, and PARP16. In particular embodiments, the mono-PARP catalytic domain is further characterized as having a mutation in a particular position in the catalytic domain. The particular positions are described in the sequence listing section of the specification above and as Xaa in SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 in the disclosed sequences. The wild type version of the PARP catalytic domain has an isoleucine residue (for PARP6, PARP7, PARP8, PARP10, PARP11, and PARP 12), a leucine residue (PARP14, PARP15), or a tyrosine residue (PARP16) in the indicated position. In the disclosed polypeptides, an amino acid substitution mutation is introduced that results in a residue smaller than an isoleucine or leucine residue (for example, a glycine, alanine, serine, cysteine, valine, threonine, or proline residue). In further examples of the disclosed polypeptide, the amino acid is mutated to an alanine or guanine as exemplified by SEQ ID NO: 9-SEQ ID NO: 24.

The disclosed polypeptides can further include mono-PARP domains other than the catalytic domain. Such domains include a WWE domain, one or more Zn finger domains, one or more macro domains, or one or more N-terminal domains. Such domains can be derived from the same mono-PARP as the mono-PARP from which the catalytic domain was derived or from a different mono-PARP as contemplated by the Examples below.

The amino acid substitutions described herein allow the mono-PARP catalytic domain to use one of the disclosed SMCs (such as 5-Bn-6-a-NAD+), as a substrate. The substrate can thereby be covalently attached to a target protein as described in the example below. The disclosed polypeptide compositions have the further characteristic that they do not catalyze the reaction with natural NAD+.

The disclosed polypeptides can include additional mutations (outside of the mutations indicated in the sequence listing) that result in amino acid substitutions—including conservative amino acid substitutions—that can result in a mono-PARP catalytic domain that has substantially the same catalytic specificity and substantially the same catalytic activity as the polypeptides described as SEQ ID NO: 1 to SEQ ID NO: 24. Substantially the same means not statistically significantly different when measured according to a method disclosed herein. Such mutations can have other improved characteristics such as more efficient expression in a recombinant expression system, particular antibody specificity, or improved stability or other characteristics.

The disclosed polypeptides can further include a label or protein tag as described above to facilitate purification, identification, or other activities.

Methods of identifying targets of a mono-PARP. Disclosed are methods of identifying a protein target of a mono-PARP. These methods involve contacting one of the disclosed SMCs (for example 5-Bn-6-a-NAD+), with one of the disclosed polypeptides (said polypeptide including, for example, SEQ ID NO: 15). Any one or more of the disclosed SMCs and any one or more of the disclosed polypeptides can be used in any combination. For the purposes of this method, in particular embodiments, the contacting occurs within a cell, such as a living cell. The cell can be any cell such as a human cell line, a cell collected from a biopsy (including a blood cell), a tumor cell, or any other living human cell for which the user of the method wishes to identify a mono-PARP target. The contacting can occur by any method known in the art. For example, the polypeptide can be expressed within the cell via an expression vector that is transfected into the cell by any method known in the art and the SMC can be added to the media.

In the specific example described above, the cell is subjected to conditions that result in the polypeptide including SEQ ID NO: 15 catalyzing a reaction that results in the covalent attachment of 5-Bn-6-a-NAD+ to its protein targets within the cell. The 5-Bn-6-a-NAD+ conjugated protein targets can then be identified by any method known in the art, including those methods described below. For example, a label such as biotin can be conjugated to the 5-Bn-6-a-NAD+, the protein targets purified using avidin or streptavidin, and the protein targets identified by mass spectrometry. Alternatively, the 5-Bn-6-a-NAD+ on the protein targets can be labeled with a fluorescent protein, a tag, or other label.

Methods of selecting mono-PARP antagonists. Also disclosed are methods of selecting a test compound as an antagonist of a mono-PARP. The methods involve contacting one of the disclosed SMCs (for example, 5-Bn-6-a-

NAD+) with one of the disclosed polypeptides (for example, a polypeptide including SEQ ID NO: 15). Any one or more of the disclosed SMCs and any one or more of the disclosed polypeptides can be used in any combination. These are further contacted with a known protein target of the mono-PARP (in this particular example, the target can be SRPK2 or any fragment thereof that is MARylated by PARP10 or another PARP, but any protein target of the selected PARP can be used including a protein target determined by the method above) under conditions that are known to result in the covalent attachment of the SMC to the known protein target via mono-PARP activity, at least in the absence of the one or more test compounds. These are further contacted with a test compound. The contacting occurs within a mixture. If a reliable reduction in covalent attachment of the SMC to the known protein target is observed, the test compound is a mono-PARP antagonist. As is understood by one of ordinary skill in the art, a reliable reduction is one that is statistically significant and reproducible. The various components can be added to the mixture in any order. The mixture can be any mixture including a cell-free mixture. Alternatively, the mixture can include a cell, including a living cell, including a living cell that expresses the disclosed polypeptide as described above.

In the specific example described above, the mixture is subjected to conditions that result in the polypeptide including SEQ ID NO: 15 catalyzing a reaction that results in the covalent attachment of 5-Bn-6-a-NAD+ to the protein target. If a test compound causes less covalent attachment of the 5-Bn-6-a-NAD+ to the protein target relative to a negative control (such as a vehicle only control including the buffer in which the test compound was originally provided), then that test compound is selected as an antagonist of (in the specific example here) PARP10.

The methods herein can be used to screen a plurality of test compounds, also described as a library of test compounds. The methods herein can be further adapted to high throughput screening of a set of test compounds in batches of 96, 384, 1048, or more on assay plates adapted for such screening.

EXAMPLES

The following examples are illustrative of disclosed compositions and methods.

Example 1

Identification of Engineered Mono-PARP

Modified NAD+ Analogue Pairs. A sensitized enzyme-modified substrate ("bump-hole") method was used in identifying the direct protein targets of poly-PARPs (Carter-O'Connell and Cohen, Curr Prot Chem Biol 7, 121-139 (2015) and Carter-O'Connell et al, J Am Chem Soc 136, 5201-5204 (2014); both of which are incorporated by reference herein. This method involved mutating an active site lysine residue (Lys903 in human PARP1, referred to here as the "ceiling" position) to an alanine to create a unique pocket for accommodating a C-5 ethyl group on the nicotinamide ring of the NAD+ analogue, 5-Et-6-a-NAD+. This NAD+ analogue contains an alkyne at the N-6 position of the adenine ring to aid in target identification using click conjugation to a rhodamine-azide or biotin-azide. It was shown that 5-Et-6-a-NAD+ can be used as a selective substrate for K903A (KA), but not wild-type (WT) PARP1, and mutation of the ceiling lysine to an alanine in the other poly-PARPs yielded similar results (Carter-O'Connell and Cohen, 2015 supra, Carter-O'Connell et al, 2014 supra).

Unlike the poly-PARPs, the mono-PARPs do not have a lysine at the ceiling position; rather, they contain a leucine (PARP10, 15), an isoleucine (PARP16, 17), or a tyrosine (PARP7, 8, 11, 12, and 14) as demonstrated by a structure-based sequence alignment (FIGS. 1A and 5). Overlay of the crystal structures of 3-aminobenzamide-bound PARP10 and PARP1 (Ruf et al, 1998 supra) reveals that Leu926 in PARP10 occupies a similar space as Lys903 in PARP1 (FIG. 1B), suggesting that mutation of the ceiling position in mono-PARPs to a smaller amino acid (e.g. alanine, glycine, serine, cysteine, valine, threonine, or proline) would accommodate 6-a-NAD+ analogues containing a substitution at the C-5 position of the nicotinamide ring.

Figure 1D:
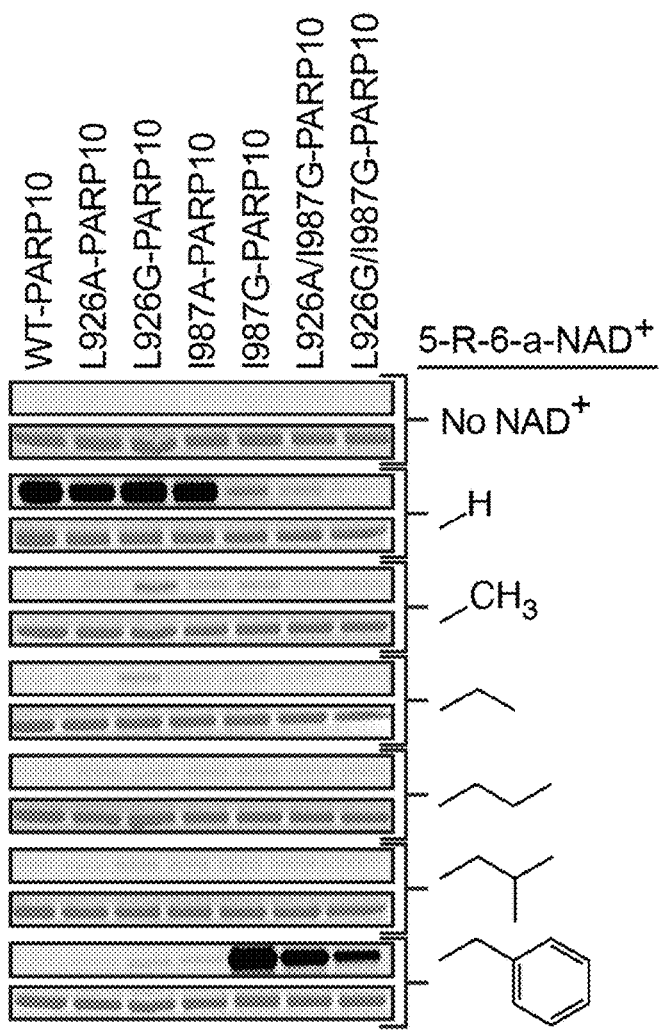
Figure 1E:
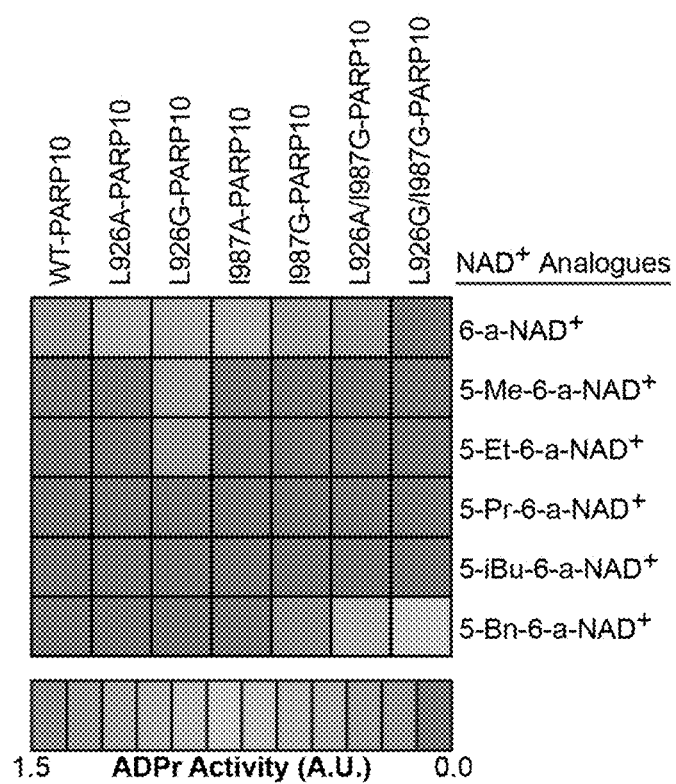

It was first tested whether or not mutation of the leucine at position 120 of the wild type PARP10 catalytic domain (corresponding to SEQ ID NO: 4 herein with an L residue at position 120, also called WT-PARP10cat herein) to an alanine or glycine (corresponding to SEQ ID NO: 18 and SEQ ID NO: 17, respectively) would confer sensitivity to C-5 substituted 6-a-NAD+ analogues. In addition to the 6-a-NAD+ analogue—5-Et-6-a-NAD+—a panel of analogues containing either a methyl, propyl, isobutyl, or benzyl group at the C-5 position (5-Me-6-a-NAD+, 5-Pr-6-a-NAD+, 5-iBu-6-a-NAD+, and 5-Bn-6-a-NAD+, respectively) was synthesized to further probe the unique binding pockets in engineered mono-PARPs (See Example 8 below). To test the reaction of these mutants C-5 substituted 6-a-NAD+ analogue pairs, wild type PARP10 catalytic domain (PARP10cat)-mediated MARylation of the known substrate SRSF protein kinase 2 (SRPK2) (Haikarainen et al, PLoS One 8, e65404 (2013) and Morgan and Cohen, ACS Chem Biol (2015); both of which are incorporated by reference herein) was monitored by click conjugation to a rhodamine-azide probe and a subsequent in-gel fluorescence detection (FIG. 10). 6-a-NAD+ was used as a substrate to mediate SRPK2 MARylation by WT-PARP10cat, and to a lesser extent by L926A— and L296G-PARP10cat (FIGS. 1D, 1E). Importantly, none of the C-5 substituted 6-a-NAD+ analogues were used by WT-PARP10cat (FIGS. 1D, 1E). 5-Me-6-a-NAD+ and 5-Et-6-a-NAD+ were used by L296G-PARP10cat, but were very poor substrates (5% MARylation activity compared to WTPARP10cat with 6-a-NAD+, FIGS. 1D, 1E).

Based on these results, an alternative amino acid within the nicotinamide binding site of mono-PARPs was sought such that when mutated to a smaller amino acid, the site might confer sensitivity to the orthogonal NAD+ analogues. Amino acid 120 of SEQ ID NO: 4 herein (which is isoleucine in wild type PARP10 and also called 11e987 herein) is located in the "floor" position of PARP10. This amino acid was selected for two reasons: (1) it makes van der Waals contacts with the C-5 position of the benzamidine ring of 3-aminobenzamide (FIG. 1B); and (2) it is well-conserved across the mono-ARTD subfamily (FIG. 1A). This amino acid was then mutated in PARP10cat to either an alanine or glycine (corresponding to SEQ ID NO: 16 and SEQ ID NO: 15 respectively) and it was then determined if these engineered mutants could use C-5 substituted 6-a-NAD+ analogues as substrates. It was found that 5-Bn-6-a-NAD+ was used efficiently by a polypeptide including SEQ ID NO: 15 (also called I987G-PARP10 herein). The polypeptide including SEQ ID NO: 15 showed 140% MARylation activity compared to WT-PARP10cat with 6-a-NAD+, FIGS. 1D, 1E); by contrast, 6-a-NAD+ was a poor substrate the construct including SEQ ID NO: 15 (5% MARylation activity compared to WT-PARP10cat with 6-a-NAD+, FIGS. 1D, 1E). Taken together, these results demonstrate that mutation of the isoleucine at position 120 of SEQ ID NO: 4 herein in the floor position of PARP10 results in an orthogonal switch in substrate specificity from 6-a-NAD+ to 5-Bn-6-a-NAD+.

Figure 6A:
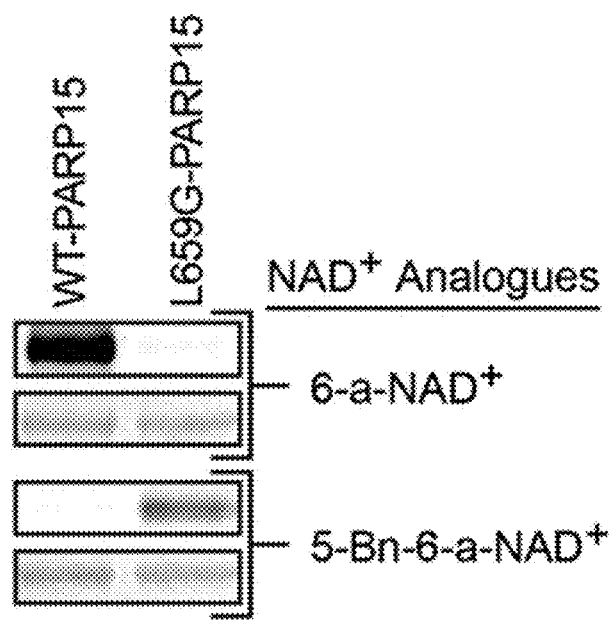
FIGS. 6A and 6B.
Figure 6B:
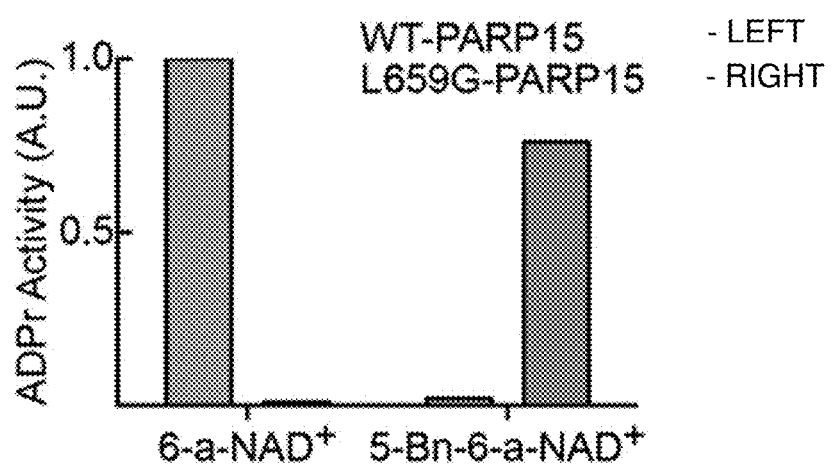

It was next tested whether mutating the floor position in another mono-PARP would confer sensitivity to 5-Bn-6-a-NAD+. A construct including a wild type PARP15 catalytic domain, which corresponds to a leucine at position 160 of SEQ ID NO: 8 (also called WT-PARP15cat) and a construct including SEQ ID NO: 23 (also called L659G-PARP15cat herein) were expressed and their in vitro MARylation activity tested with both 6-a-NAD+ and 5-Bn-6-a-NAD+. Similar to SEQ ID NO: 15, SEQ ID NO: 23 used 5-Bn-6-a-NAD+ selectively to MARylate SRPK2 (FIGS. 6A and 6B). Importantly, WT-PARP15cat did not use 5-Bn-6-a-NAD+ (FIGS. 6A and 6B). All of the mono-PARPs contain a leucine or isoleucine at corresponding positions in the catalytic domain (with the exception of PARP16 which has a tyrosine, see sequence listing and FIG. 1A). This result suggests that this residue may be mutated to a smaller amino acid to generate a 5-Bn-6-a-NAD+ sensitive catalytic domain throughout the mono-PARP subclass. Examples of such mutants are listed in detail as SEQ ID NO: 9-SEQ ID NO: 24 herein.

Example 2

Figure 2A:
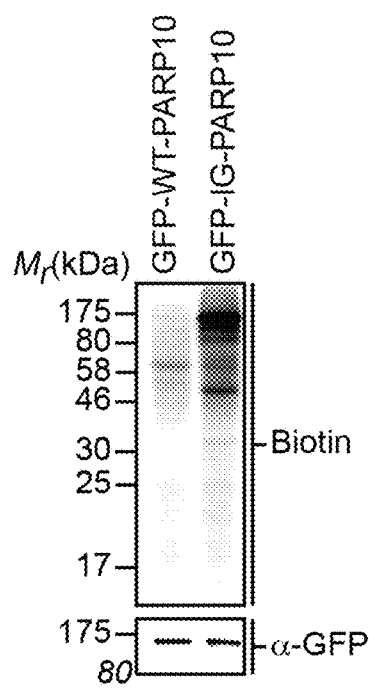
FIGS. 2A-2D.

SEQ ID NO: 15-5-Bn-6-a-NAD+ Pair Specifically Labels Direct Protein Targets in Multiple Cell Lines It was next determined if a polypeptide including SEQ ID NO: 15 could be used to label direct protein targets in a cellular context. GFP-SEQ ID NO: 15 (IG-PARP10) or GFP-WT-PARP10—(GFP linked to SEQ ID NO: 4 with an isoleucine at position 120—(WT-PARP10) were expressed in human embryonic kidney (HEK) 293T cells. Lysates were prepared and incubated with 5-Bn-6-a-NAD+(100 μM), followed by click conjugation with biotin-azide. Treatment of lysates from SEQ ID NO: 15 transfected cells with 5-Bn-6-a-NAD+ resulted in labeling of several bands, the predominant band corresponding to the size of auto-MARylated SEQ ID NO: 15 (FIG. 2A). By contrast, treatment of lysates from WT-PARP10 transfected cells with 5-Bn-6-a-NAD+ resulted in a low-level of background labeling—most likely due to endogenously biotinylated proteins (FIG. 2A). These result demonstrate that the SEQ ID NO: 15-5-Bn-6-a-NAD+ pair can be used to label direct MARylation targets of PARP10.

Figure 7:
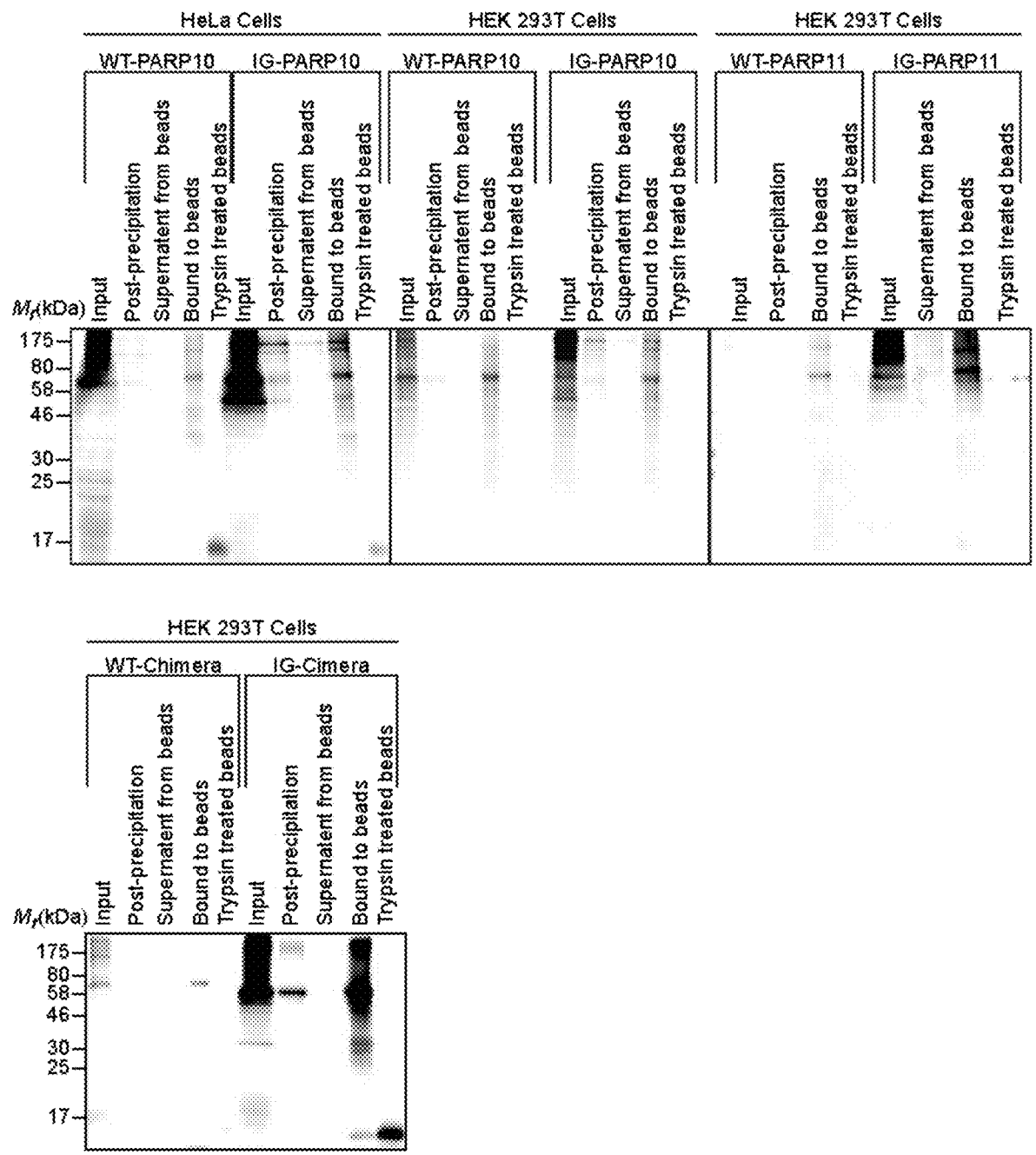
FIG. 7 is a set of four images of immunoblots of the indicated fractions from the NeutrAvidin enrichment protocol (Carter-O'Connell et al, 2015 infra) were imaged using streptavidin-HRP. 5-Bn-6-a-NAD+ was spiked into the appropriate lysate (expressing either WT— or IG-PARP), samples were labeled, conjugated to biotin-PEG3-azide, enriched, and submitted for LC-MS/MS analysis.

Next, the disclosed labeling method was used to identify direct MARylation targets of PARP10 using LC-MS/MS. HEK 293T lysates generated from cells expressing WT-PARP10 or SEQ ID NO: 15 were treated with 5-Bn-6-a-NAD+ (100 μM). MARylated proteins were conjugated to biotin-azide, enriched using NeutrAvidin agarose, digested with trypsin, and subjected to LC-MS/MS (FIG. 7). A total of 803 PARP10-specific protein targets were found. This represents a much broader target set than that found for either PARP1 or PARP2 (42 and 339 proteins, respectively), (Carter-O'Connell et al, 2014 supra). There was no overlap between the targets determined using the disclosed method and previously published PARP10 targets identified using protein microarrays (Feijs et al, Cell Comm Sig 11, 5 (2013); incorporated by reference herein). This could be due to differences in the context in which the labeling reactions are performed in that the disclosed methods identify PARP10 targets in a complex cellular context in that other PAR and MAR detection methods rely on non-family member specific labeling methods.

Figure 2B:
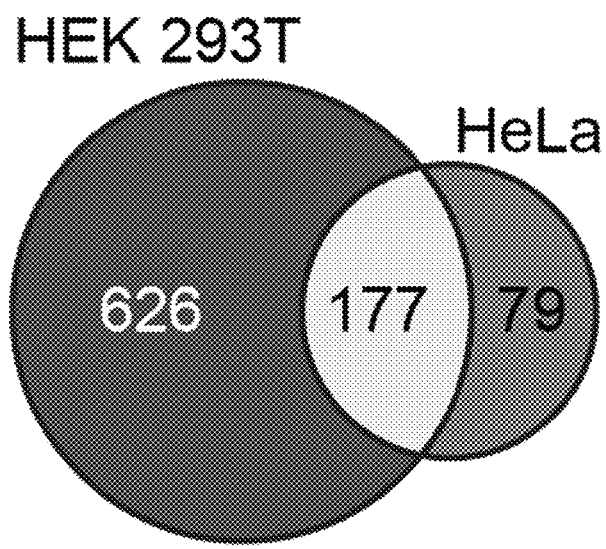

Given the scarcity of data regarding the physiological role of PARP10, including its basal activity in different cell types, it was possible that the choice of cell type could be inflating the actual target list of PARP10 targets. To address this possibility, the labeling experiment was repeated in HeLa cells (FIG. 7). In HeLa cells 256 direct PARP10 targets were identified. A comparison with the list of PARP10 targets identified in HEK 293T cells revealed that a majority of the targets found in HeLa cells (69%) were also identified in the HEK 293T samples (FIG. 2B). The smaller number of targets identified in HeLa cells compared to HEK 293T cells is likely due to the decreased expression levels or activity of PARP10 in HeLa cells compared to HEK 293T cells.

Figure 2C:
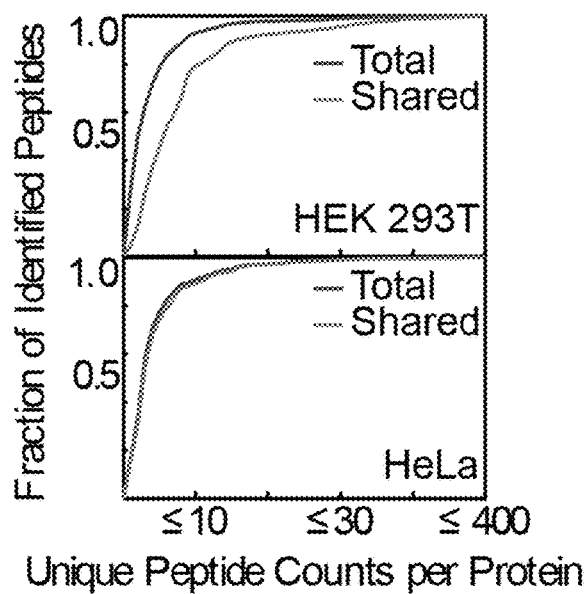

To identify the most relevant cellular targets of PARP10, each of the PARP10 direct protein targets found using the disclosed methods were ranked based on the number of peptide counts per protein identified in the LC-MS/MS analysis. Preferred PARP10 targets would be labeled more efficiently and would thus be enriched relative to less relevant targets. Preferred PARP10 target peptide fragments would also appear more frequently in the LC-MS/MS run. Importantly, the control sample generated from lysates expressing WT-PARP10 allowed the removal of any proteins that would be enriched for non-enzymatic reasons (e.g. higher abundance proteins that bind non-specifically to NeutrAvidin agarose or proteins that are labeled non-enzymatically by 5-Bn-6-a-NAD+) from this analysis. The bulk of I987G-PARP10 targets identified in HEK 293T cells were identified based on a median of 2 peptides. Selecting for proteins that were also identified in HeLa cells causes a shift in median peptide counts from 2 to 6 peptides per protein. The cumulative distribution frequency of peptide counts per identified protein target for the shared protein pool (HEK 293T and HeLa targets) is elevated significantly above the cumulative distribution generated from the total pool of HEK 293T protein targets ($p<0.0001$, Mann-Whitney test, FIG. 2C). As the majority of HeLa targets are shared with HEK 293T there was not a significant difference in the cumulative distribution frequencies between the shared and total HeLa target pools (FIG. 2C). While it is acknowledged that some of the targets identified with lower peptide counts in the LC-MS/MS analysis might still represent relevant cellular targets of PARP10, the ranking of proteins based on peptide frequency counts—as well as their likelihood to be found in multiple cell lines—provides a starting point for linking PARP10-specific MARylation to cellular processes.

Figure 2D:
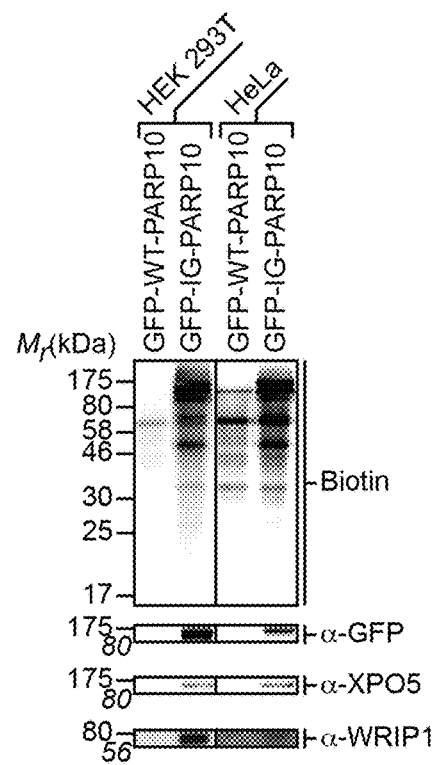

To confirm the LC-MS/MS results, two protein targets shared by HeLa and HEK 293T—XPO5 and WRIP1 were identified by Western blot with target-specific antibodies after NeutrAvidin enrichment. Both XPO5 and WRIP1, as well as auto-MARylated IG-PARP10, were selectively enriched from lysates generated from either HEK 293T or HeLa cells expressing SEQ ID NO: 15 and treated with the 5-Bn-6-a-NAD+ (FIG. 2D). Taken together, the results demonstrate that the disclosed methods can be used for the identification of direct MARylation targets of PARP10 in a complex mixture.

Example 3

PARP11 and PARP10 MARylate Separate Target Pools Involved in Distinct Cellular Processes The generalizability of the disclosed methods was determined by identifying the direct MARylation targets of another mono-PARP. The target profile of PARP11 is interesting for a number of reasons: first, PARP11 includes a fairly simple modular structure as compared to the other mono-PARPs. Second, wild type PARP11 has an isoleucine at position 164 of SEQ ID NO: 5, corresponding to the isoleucine at position 120 of SEQ ID NO: 4 of wild type PARP10, but a tyrosine at the PARP10-L926 'ceiling' position (See FIG. 1A), allowing confirmation that the disclosed methods will work with mono-PARPs with different amino acids at the L926-I987 interface. Furthermore, the comparison of two separate mono-PARP target profiles would allow an examination of the level of redundant target selection in the mono-PARP family. Finally, recent work has implicated PARP11 in nuclear membrane maintenance (Meyer-Ficca et al, Biot Reprod 92, 80 (2015); incorporated by reference herein) providing a potential biological pathway to probe the target list resulting from the disclosed methods against.

Figure 3A:
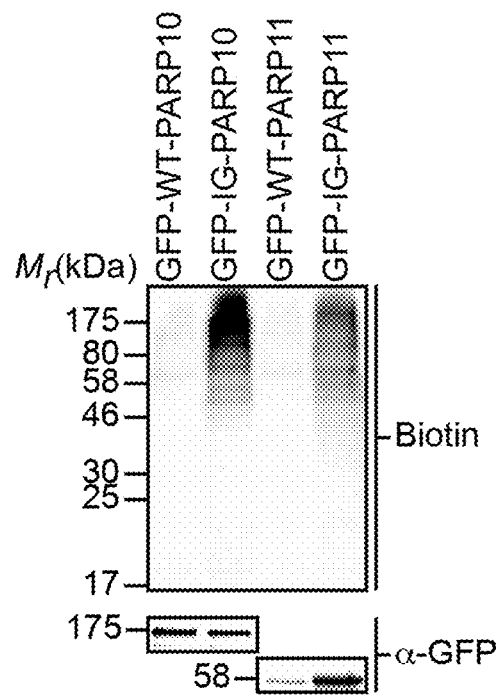
FIGS. 3A-3D.

The MARylation activity of polypeptides including GFP-SEQ ID NO: 17 (also called I313G-PARP11 herein) was compared to that of SEQ ID NO: 15 in HEK 293T lysates. Treatment of lysates from SEQ ID NO: 17 transfected cells with 5-Bn-6-a-NAD+ resulted in labeling of several bands (FIG. 3A). Minimal background labeling was detected in lysates expressing WT-PARP11, further demonstrating the inability of non-engineered mono-PARPs to use 5-Bn-6-a-NAD+ as a substrate for MARylation. The banding pattern for SEQ ID NO: 17 is different from that produced by PARP10, indicating that PARP11 and PARP10 are indeed targeting distinct and family-member specific proteins (FIG. 3A).

Next, direct targets of PARP11 were identified using LC-MS/MS. HEK 293T lysates generated from cells expressing WT-PARP11 or SEQ ID NO: 17 were treated with 5-Bn-6-a-NAD+ (100 µM). MARylated proteins were conjugated to biotin-azide, enriched using NeutrAvidin agarose, digested with trypsin, and subjected to LC-MS/MS (FIG. 7). A total of 260 direct SEQ ID NO: 17 targets were identified (thresholds discussed in methods). Of the 803 and 260 protein targets identified for PARP10 and PARP11, respectively, a total of 140 and 21 proteins (respectively) were identified in duplicate biological replicates (Table 1). For the subsequent analysis comparing PARP10 and PARP11 MARylation, targets that were present in both replicates were selected because the selection of protein targets identified in two separate LC-MS/MS experiments would limit the amount of non-specific target enrichment. It is possible that proteins identified in a single replicate could still represent true cellular PARP10/PARP11 targets, so full data sets for the combined protein pools were generated. Based on previous observations with KA-PARP1 and KA-PARP2, as well as the current study, it is apparent that the PARP family displays a spectrum of target specificity. In the case of both PARP2 and PARP10, a broad range of cellular targets was observed, while PARP1 and PARP11 have a much narrower target profile (Table 1). The disclosed methods have yielded the first data set capable of distinguishing the PAR and MAR targeting preferences for multiple PARP family members. Further the disclosed methods are generalizable through the mono-PARP subclass and should aid in future investigations with the other family-members.

TABLE 1

Direct Protein Targets Identified by LC-MS/MS

|  | KA-PARP1[a] | KA-PARP2[a] | IG-PARP10 | IG-PARP11 |
|---|---|---|---|---|
| Total Proteins Identified | 123 | 488 | 961 | 479 |
| Proteins with ≥2 Unique Peptides | 91 | 428 | 848 | 294 |
| Proteins Enriched Above Background[b] | 38 | 279 | 803 | 260 |
| Proteins Identified in Duplicate | 15 | N.D.[d] | 140 | 21 |
| PARP Family-Member Specific Proteins[c] | 13/14 | 117/N.D.[d] | 534/90 | 43/13 |

Figure 3B:
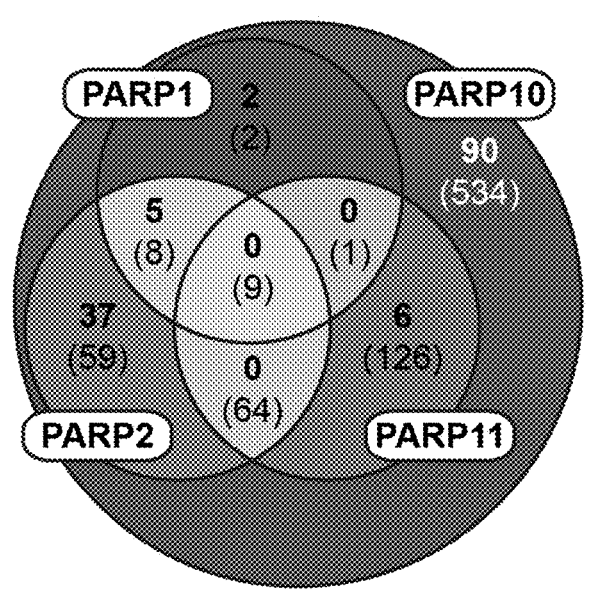
Figure 3C:
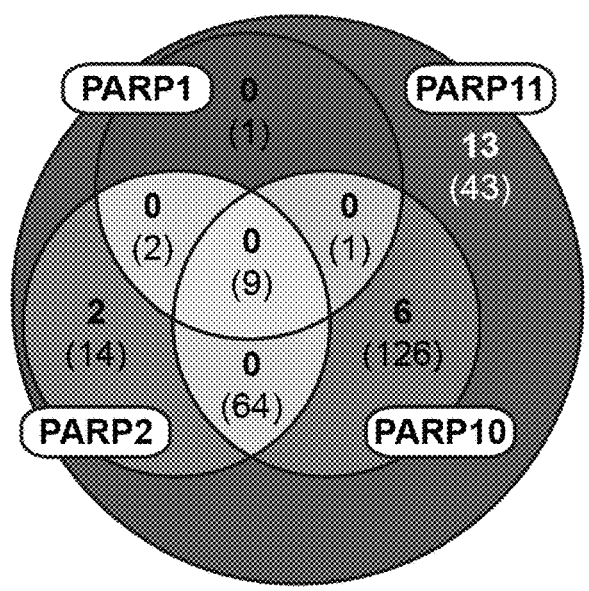

[a]KA-PARP1 and KA-PARP2 targets were identified as previously described (Carter-O'Connell et al., 2014)
[b]Defined as ≥2-fold enrichment in the IG-PARP sample versus the WT-PARP sample
[c]Targets that were identified for a single PARP family-member from the collected datasets from either at least a single replicate (left) or in duplicate (right)
[d]KA-PARP2 identification was completed for a single replicate and is not included in the duplicate analysis Comparing the protein target lists for KA-P ARP1, KA-PARP2, SEQ ID NO: 15, and SEQ ID NO: 17 allowed the identification of the extent of overlap between these PARP family-members. Interestingly, the PARP10 target list overlaps to a greater degree with each of the other tested PARP family members than it does with PARP11 (FIGS. 3B, 3C). PARP10 and PARP2 in particular share 37 (26% of the total PARP10 target pool) protein targets (FIG. 3B) while PARP11 shares only 2 targets with PARP2 and no targets with PARP1 (FIG. 3C). Comparing the combined target pools also allows isolation of the protein targets that are specific for a given PARP family-member. The bulk of the identified protein targets are actually unique to either PARP10 (64%) or PARP11 (62%).

Figure 3D:
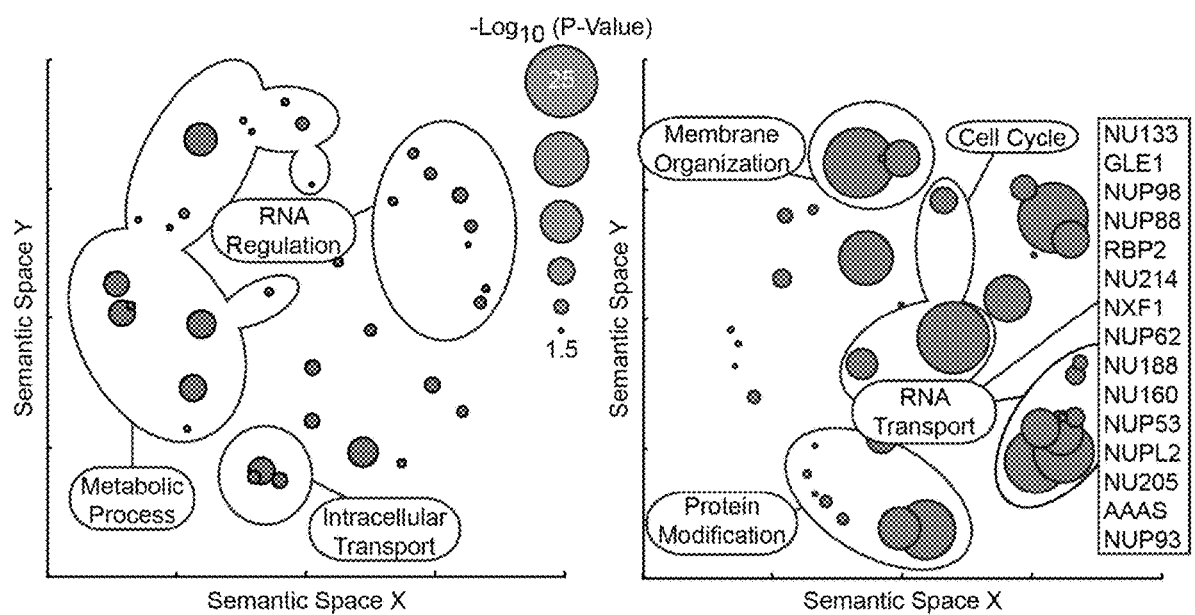

Using the target datasets for each of the PARPs detailed above, potential cellular roles for PARP10- and PARP11-mediated MARylation were determined. Using the set of PARP10- and PARP11-specific target proteins, gene ontology (GO) terms were searched that were significantly enriched (p<0.05, Bonferoni correction) within either the PARP10 or PARP11 target list. Enriched GO terms were compressed using Revigo (Supek et al., PLoS One 6, e21800 (2011); incorporated by reference herein) and semantic similarities between unique terms were plotted against the significance of the GO term enrichment (FIG. 3D). The GO term enrichment profile for PARP10 displayed a wide spectrum of biological processes, with enriched terms such as cellular metabolism (p=1.73e-12), intracellular protein transport (p=2.26e-10), protein targeting to the ER (p=1.75e-07), and mRNA metabolism (p=6.68e-05) (FIG. 3D). In contrast, the PARP11 GO term profile was highly enriched for a closely clustered set of biological processes (FIG. 3D). For PARP11, it was noted that the proteins identified in duplicate were primarily nuclear pore proteins or proteins involved in nuclear membrane organization (13 of 21 proteins). The enrichment of nuclear pore proteins led to enrichment of processes related to nuclear envelope organization (p=7.27e-24) and RNA transport (p=2.62e-24).

Figure 8:
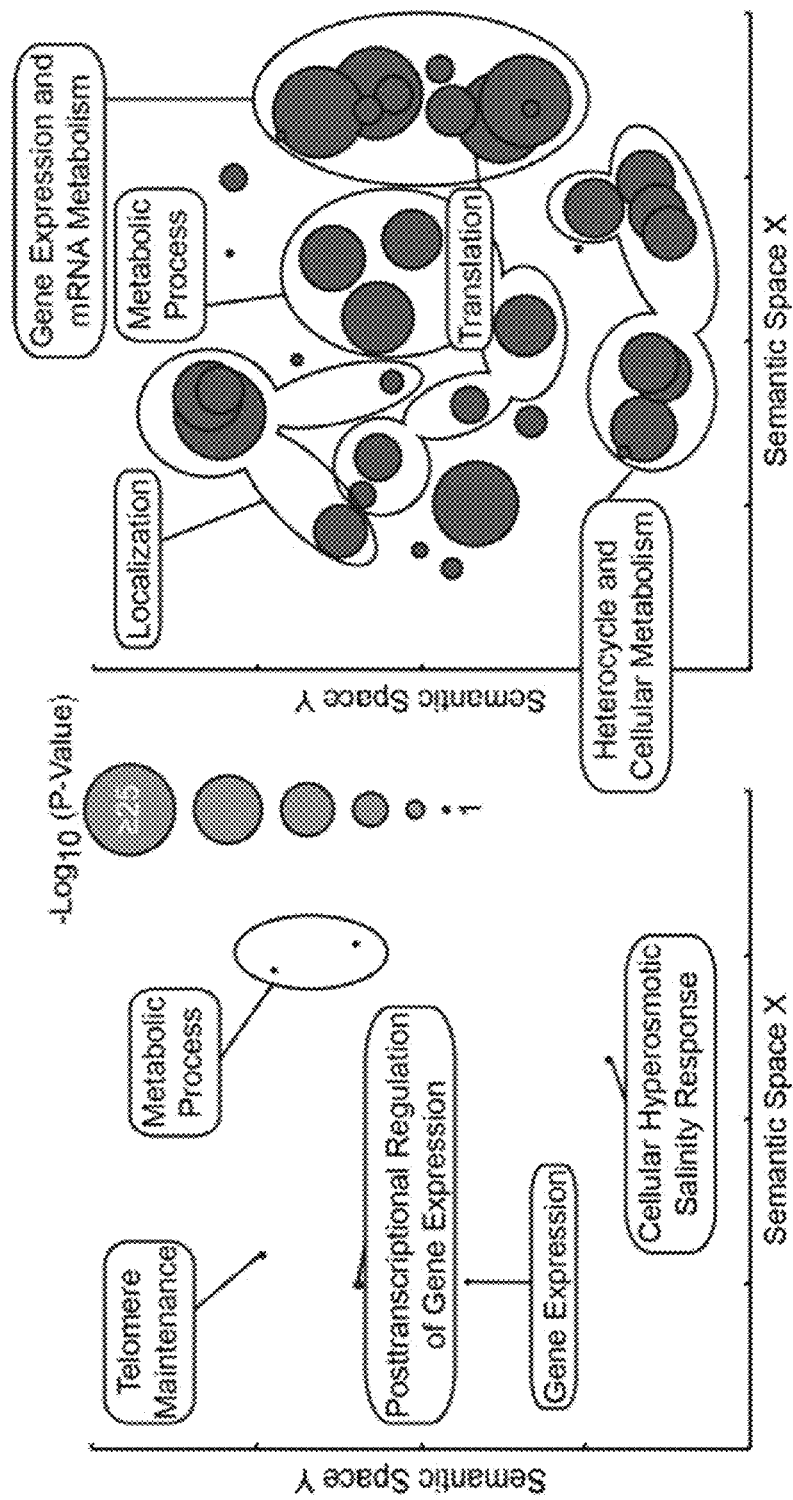
FIG. 8 is a set of two circle plots depicting enriched GO terms attached to the KA-PARP1 (left) or KA-PARP2 (right) specific LC-MS/MS identified targets. GO term enrichment was performed using the PANTHER toolkit. Significantly enriched GO terms (p<0.10, PARP1 or p<0.05, PARP2) were condensed using Revigo and similar terms were plotted based on semantic similarity. Select groups of terms are indicated. Circle radii are scaled proportionally to the − log 10 (p-value).

To compare the mono-PARP GO term profiles to the poly-PARP target lists, this analysis was performed using previously obtained PARP1 and PARP2 target datasets (FIG. 8). Interestingly, the PARP1 GO term profile was fairly limited in scope with only 8 GO terms identified (p<0.10, Bonferroni correction). The PARP1 GO terms were related to demonstrated PARP1 functions—including gene regulation (p=2.47e-02) (Ji and Tulin, Curr Opin Genetics Dev 20, 512-518 (2010) and Wacker et al, Sub Cell Biochem 41, 45-69 (2007); both of which are incorporated by reference herein) and response to osmotic stress (p=7.95e-02) (Chen et al, Am J Phys Ren Phys 292, F981-992 (2007) and Morales et al, Biochem Biophys Res Comm 270, 1029-1035 (2000); both of which are incorporated by reference herein)—though no enrichment was found for terms associated specifically with DNA double-stranded break repair. Given that the number of unique PARP1 targets identified did contain a number of DNA repair targets (notably XRCC5/6) the lack of enrichment could be due to the fact that target identification was performed under basal and not DNA damage conditions. The PARP2 GO term profile was broader than PARP1 (FIG. 8) with a clear enrichment of terms related to translation (p=1.55e-43), protein localization (p=1.70e-25), and mRNA metabolic processes (p=1.89e-33). Comparing the GO term profiles between the multiple PARP family members results in the observation that PARP2 and PARP10 label a broad target pool, but clearly are involved in distinct roles in the cell. PARP10 MARylates a set of targets lacking a clear connection between highly distinct biological functions, while the PARP2 targets are clustered tightly around mRNA regulation. In contrast, PARP1 and PARP11 have very narrow GO term profiles and are involved in very specific biological roles. Taken together, the GO term profiles for each of the PARP enzymes are distinct, with the PARP11 profile implicating a specific and novel biological role for PARP11 MARylation in nuclear pore complex regulation.

Example 4

Both the Mono-PARPcat and the Modular N-Terminal Domains are Necessary for Accurate PARP11-mediated MARylation The PARP family is defined by the presence of a conserved PARPcat domain (Ame et al, BioEsssays 26, 882-893 (2004); incorporated by reference herein). Each of the mono-PARPs is then differentiated by the presence of at least one separate modular domain (e.g., WWE, Zn fingers, macro, etc.) found on the n-terminus of the mono-PARP protein (Schreiber et al, Nat Rev Mol Cell Biol 7, 517-528 (2006); incorporated by reference herein). A major unanswered question in the PARP field is whether the n-terminal regulatory domain alone, the $PARP_{cat}$ domain alone, or both together mediate substrate targeting. One of the unique advantages of the disclosed mono-PARP—modified NAD+ analogue pairs is the ability to decouple proximal (i.e. $PARP_{cat}$) and distal (i.e. N-terminal domain) elements of mono-PARP protein targeting and address this question on a proteome-wide scale.

Figure 4A:
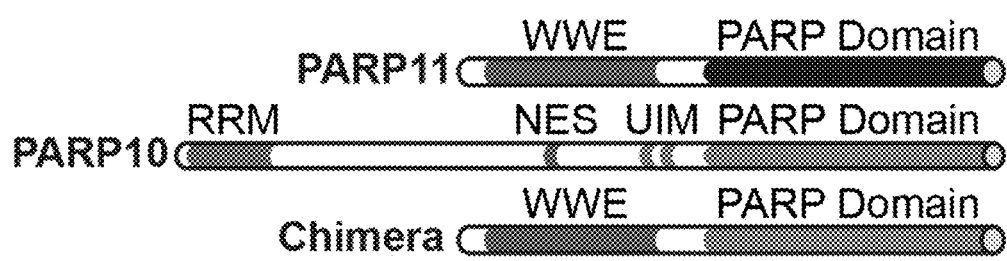
FIGS. 4A-4C.

The PARPcat domain from PARP10 is attached to a number of Zn fingers, a nuclear export sequence, and a set of ubiquitin-interaction motifs (UIMs) whereas the $PARP11_{cat}$ domain is attached only to a VWVE domain (FIG. 4A). To address the differential protein target selection requirements for each of these domains, the SEQ ID NO: 15 domain was fused to the VWVE domain from PARP11 (FIG. 4A). The resulting chimeric protein (SEQ ID NO: 15-PARP11 chimera) now possesses the distal targeting features of PARP11 and the proximal targeting features of PARP10. By comparing the direct protein targets of the SEQ ID NO: 15-PARP11 chimera with the targets of SEQ ID NO: 15 and SEQ ID NO: 17 it can be determined whether or not the targets can be selected based on proximal and/or distal interactions.

Figure 4B:
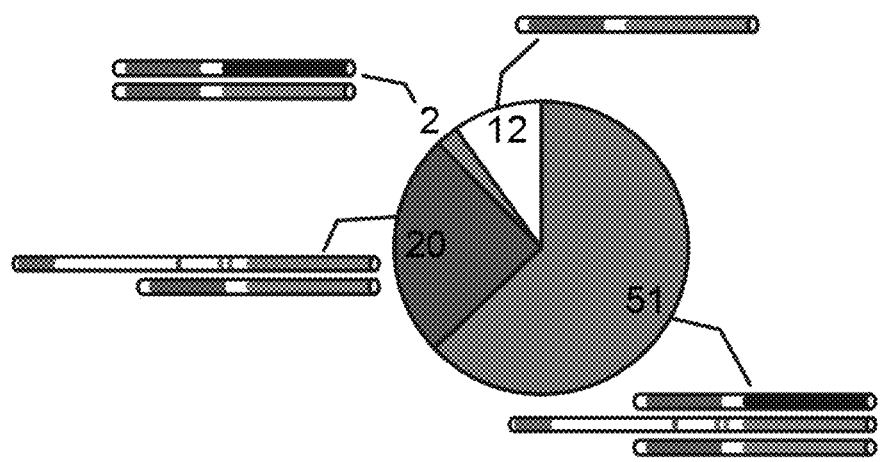

LC-MS/MS analysis was performed on an HEK 293T lysate from cells expressing I987G-chimera that were treated with the 5-Bn-6-a-NAD+(FIG. 7). A total of 85 SEQ ID NO: 15-PARP11 chimera-specific protein targets were identified. A total of 60% of the SEQ ID NO: 15-PARP11-chimera targets are shared with both SEQ ID NO: 15 and SEQ ID NO: 17 (FIG. 4B). When the shared targets of PARP10, PARP11, and the chimera are compared to the SEQ ID NO: 15-PARP11 chimera targets that are only shared with PARP10 (85% of the SEQ ID NO: 15-PARP11 chimera targets), it is clear that the $PARP10_{cat}$ domain plays an important role in target selection (FIG. 4B). However, it is also apparent that the loss of the PARP10 n-terminus has drastically reduced the number of proteins that can be targeted by the PARP10cat domain. Interestingly, there are two targets where the n-terminus of PARP11 appears to be required for target selection by the SEQ ID NO: 15-PARP11 chimera (FIG. 4B). It was also noted that of the proteins identified in duplicate PARP11 LC-MS/MS runs, only 2 were shared with the SEQ ID NO: 15-PARP11 chimera protein (NAGK and WRIP1). All of the nuclear pore proteins require both the n-terminus and the PARP11cat domain for MARylation. Finally, there was a subset of 12 proteins that are unique to the SEQ ID NO: 15-PARP11 chimera. Taken together, these results suggest that both proximal and distal substrate interactions are necessary for proper target selection. This result also suggests that the structurally similar $PARP_{cat}$ domains are playing distinct roles in target selection.

Figure 4C:
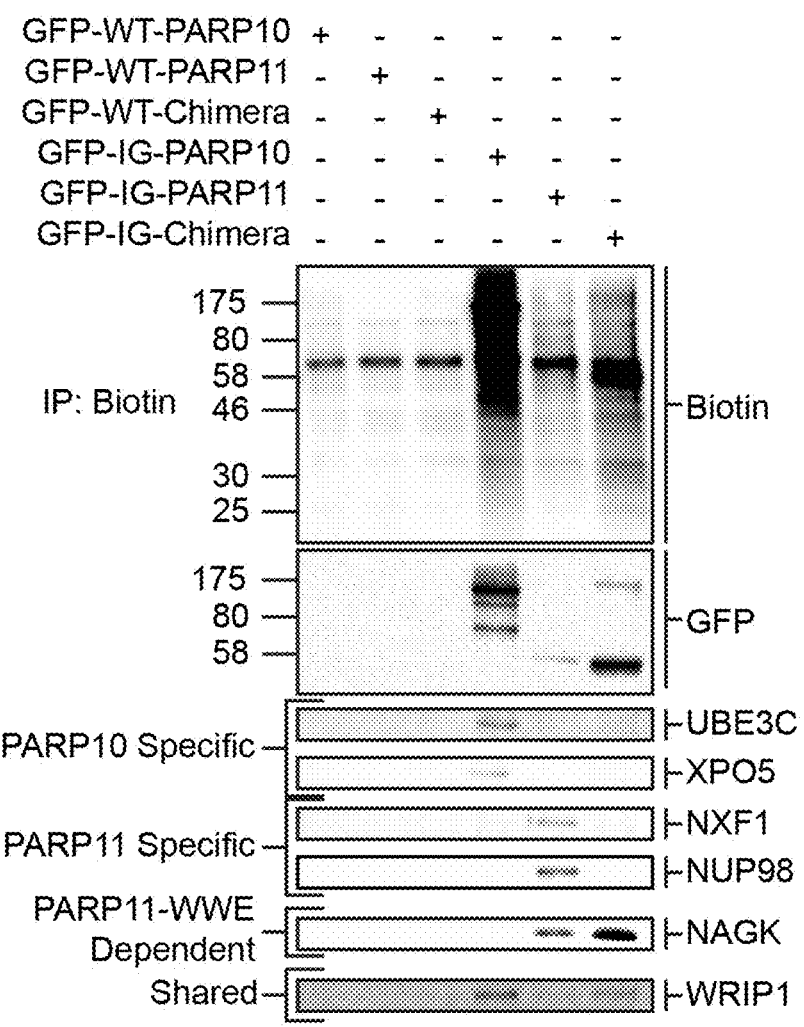

To confirm all of the LC-MS/MS results with SEQ ID NO: 15, SEQ ID NO: 17, and the SEQ ID NO: 15-PARP11 chimera, a set of PARP10-specific (UBE3C and XPO5), PARP11-specific (NXF1 and NUP98), PARP11-WWE-dependent (NAGK), and shared targets (WRIP1) were selected for identification by Western blot with target specific antibodies after NeutrAvidin enrichment. For all of the IG constructs examined, robust enrichment of the auto-MARylated proteins were observed using the GFP antibody (FIG. 4C). Enrichment of UBE3C and XPO5 was observed only in the PARP10 lane and NXF1 and NUP98 in the PARP11 lane (FIG. 4C). This result confirms that the disclosed methods are capable of distinguishing between the specific targets of multiple mono-PARP family members from a complex mixture. The PARP11-specific target, NAGK, is enriched in both the PARP11 and chimera lane and is therefore dependent primarily on PARP11 n-terminal recognition for labeling (FIG. 4C). Finally, the mono-PARP pan-selective target, WRIP1, is enriched in all three IG variant lanes (FIG. 4C). In each case, none of the selected targets are enriched from HEK 293T lysates expressing the VVT constructs, confirming the necessity of the IG mutation for mono-PARP family-member specific MARylation using 5-Bn-6-a-NAD+ (FIG. 4C). Taken together, the disclosed methods are able to identify direct family-member specific mono-PARP targets in complex lysates.

Example 5

PARP10 Targets

The PARP10 targets identified using the disclosed methods share notable overlap with previously reported cellular functions of PARP10. In particular, the presence of a number of ubiquitin ligases (e.g. UBE3C) was noted. PARP10 contains two UIMs that were shown to interact with ubiquitinylated tumor-necrosis factor-receptor associated factor (TRAF) to aid PARP10 in targeting the NF-κB essential modulator (NEMO) for MARylation (Verheugd et al, Nature Comm 4, 1683 (2013); incorporated by reference herein). One possibility is that PARP10 regulates the ubiquitin signal cascade through MARylation of ubiquitin ligases. Additionally, PARP10 has been implicated in the coordination of cellular trafficking (Kleine et al, CCS 10, 28 (2012); incorporated by reference herein) and a number of cellular trafficking proteins were found in the target dataset. However, while the target list for PARP10 most likely contains a number of targets that are involved in specific signaling events mediated by PARP10, there is still a broad array of cellular targets that are MARylated by PARP10 that have no clear functional relationship to each other. Potentially, the broad promiscuity evidenced by PARP10 might actually play a role in the function of PARP10 in the cell. PARP10 has been shown to interact with p62, a ubiquitin receptor associated with autophagy (Kleine et al, 2012 supra). In certain conditions, PARP10 forms cytosolic clusters that bind p62, which implicates PARP10 in trafficking targets to the autophagosome. It is therefore possible that in this role, PARP10 is modifying a broad array of targets that are being sent to the autophagosome for degradation. If PARP10 MARylation were key to autophagosomal trafficking, then its potential targets would by definition not be highly specific. Further exploration of the role for PARP10 in autophagy will be required to determine if the broad targeting of PARP10 is important for its function in this pathway.

Example 6

PARP 11 Targets

Compared to PARP10, relatively little is known regarding the function of PARP11 in the cell. Recent work has linked PARP11 to nuclear shaping in spermatids undergoing nuclear condensation and differentiation (Meyer-Ficca et al, 2015 supra), yet the PARP11-specific targets responsible for this process are unknown. The PARP11 targets identified using the disclosed methods appear to be directly related to the coordination of the nuclear envelope and the organization of nuclear pores. One of the PARP11-specific targets identified using the disclosed methods—the nuclear pore complex protein Nup98-Nup96 (NUP98)—was previously disclosed elsewhere as interacting with PARP11. The target list for PARP11 derived from the disclosed methods provides a clear point of entry for exploring in molecular detail how PARP11 MARylation regulates nuclear pore complex biology.

Example 7

Other Examples of the Mono-PARP Subclass

A PARP1 homolog can be found in all five of the eukaryotic supergroups for which sequencing data is available (Citarelli et al, BMC Evolut Biol 10, 308 (2010). In contrast, homologs to the mono-PARPs are not conserved throughout eukaryotes; yet, there was a last common eukaryotic ancestor that expressed a PARP-like protein with mono-transferase activity that evolved separately from the poly-PARPs (Citarelli et al, 2010 supra); incorporated by reference herein). Two related mono-PARP PARP clades apparently underwent parallel evolution to develop similar catalytic domains, suggesting that the mono-PARP$_{cat}$ domains are tightly constrained to maintain key structural features. The constrained mono-PARP$_{cat}$ domain was attached to a diverse array of modular regulatory domains during evolution. Some of these domains—notably the macro domains found on PARP9, PARP14, and PARP15— are under positive selection and changing rapidly (Daugherty et al, PLoS Genetics 10, e1004403 (2014); incorporated by reference herein). Therefore it seemed possible that the constrained mono-PARP$_{cat}$ domains played a minor role in target selection while the rapidly evolving modular regulatory domains directed the target selection for the mono-PARPs. For PARP10 and PARP11 at least this is not the case as the SEQ ID NO: 15-PARP11 chimera construct demonstrated that both the catalytic domain and the modular n-termini are necessary but insufficient to drive precise MARylation. It will be important determine which motifs in the catalytic domain are driving proximal target selection and how changes in both the regulatory and catalytic domains have cooperated to drive the diversity of mono-PARP target selection.

One of the remaining challenges in understanding the relationship between PARP family member specific targeting and cellular function is the identification of the specific amino acids targeted by a given mono-PARP. It appears that while PARylation primarily targets acidic amino acids (i.e. glutamate and aspartate), MARylation may be more promiscuous in its site selection. Indeed, a recent study demonstrated that mono-PARPs could be auto-MARylated not only on glutamate and aspartate acids, but also on lysine and cysteine (Vyas et al, 2014 supra). The identity of the MARylated amino acids will be essential for more complete understating of mono-PARPs functions in cells. The disclosed methods can be combined with a recently described method to globally identify PARylated and MARylated sites in protein targets (Daniels et al, J Proteome Res 13, 3510-3522 (2014); incorporated by reference herein). In this fashion the disclosed methods can be used to map PARP targeting to a specific site on a protein substrate and delve deeper into the functional role of MARylation in the cell.

Example 8

Procedures

Cell Culture: HEK 293T and HeLa cells were grown in DMEM (Gibco) supplemented with 10% fetal bovine serum (FBS, HyClone), penicillin/streptomycin (Invitrogen), and 1× glutamax (Gibco) at 37° C. and 5% $CO_2$. Transient transfections of HEK 293T cells with 20 μg of GFP-tagged expression vectors per 10 cm dish (70% confluency) were performed using the CalPhos system (Clontech) according to manufacturer's instructions. Transient transfections of HeLa cells were performed with 15 μg GFP tagged expression vectors and 30 μg lipofection reagent per 10 cm dish using Lipofectamine 2000 (Invitrogen). Cells were lysed in HEPES buffer supplemented with cOmplete EDTA-free protease inhibitor (Roche) and cell debris was cleared by centrifugation at 14,000 g for 5 min at 4° C.

SRPK2 MARylation Assay: 1 μM of each PARP10cat variant was incubated with 3 μM SRPK2 and 100 μM of each modified NAD+ analogue for 2 hours at 30° C. in a 20 μL reaction volume including 50 mM HEPES, pH 7.5, 100 mM NaCl, 10 mM MgCl2, and 0.5 mM TCEP. Click conjugation was performed with 1.5 mM THPTA, 750 μM $CuSO_4$, 300 μM sulforhodamine B-PEG3-azide, and 7.5 mM sodium ascorbate in 1× PBS for 1 hour at room temperature (rt). SRPK2 labeling was quantified using Image Lab v5.2 (Bio-Rad).

Figure 9A:
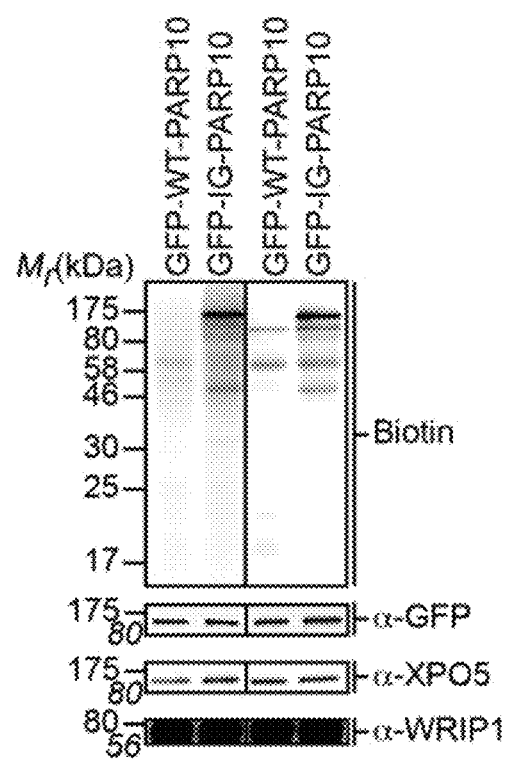
FIGS. 9A and 9B.
Figure 9B:
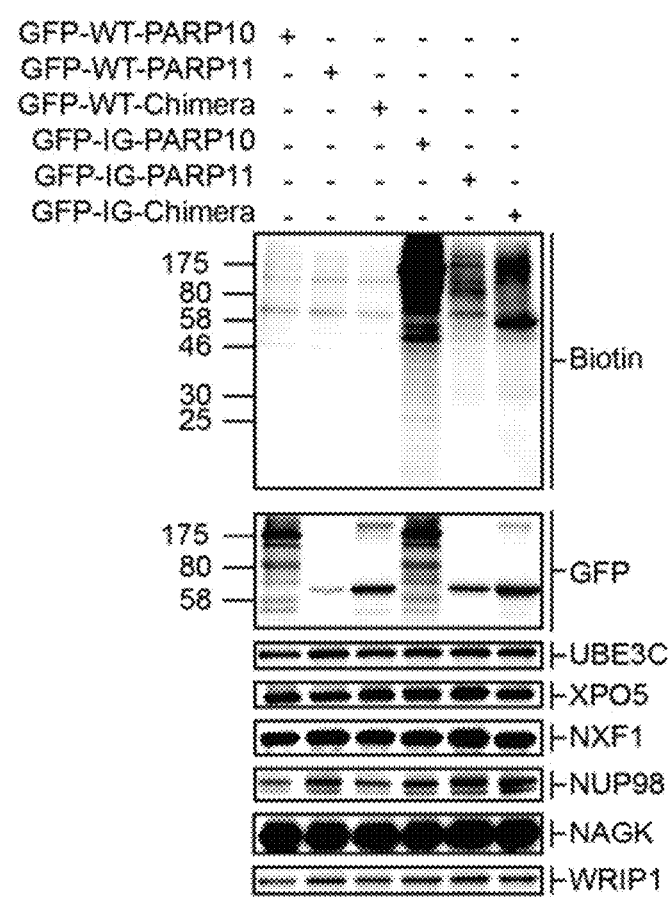

NeutrAvidin Enrichment and LC-MS/MS Analysis: 1 mg of total protein from either HEK 293T or HeLa lysate from cells expressing WT- or IG-tagged PARP variants was incubated with 100 μM 5-Bn-6-a-NAD+ for 2 hours at 30° C., click conjugated to biotin-PEG3-azide, subjected to enrichment using NeutrAvidin agarose (Pierce), and proteolysis as previously described (Carter-O'Connell and Cohen, 2015 supra; Carter-O'Connell et al, 2014 supra). MS experiments were performed using an Orbitrap Fusion (Thermo) equipped with a capillary HPLC system. Raw MS/MS scans were interpreted by SEQUEST using a UniProtKB/Swiss-Prot human database amended with sequences for the GFP-tagged PARP variants and common contaminants as previously described (Yan et al, Mol Biol Cell 21, 1945-1954 (2010); incorporated by reference herein). MARylated PARP10, PARP11, and chimeric targets were identified based on the following: (1) at least two unique peptide identifications; (2) total peptide counts enriched 2-fold above GFP-VVT-PARP controls; (3) and appearance in ≤ half the total background datasets analyzed to date using modified 6-a-NAD+ probes. GO enrichment was performed using Amigo (Ashburner et al, Nat Genetics 25, 25-29 (2000); Mi et al, Nucl Acids Res 38, D204-D210 (2010); Thomas et al, Genome Res 13, 2129-2141 (2003); all of which are incorporated by reference herein)—selecting for GO terms enriched with a p-value ≤0.05 (unless stated otherwise)—and compression was performed using Revigo (Supek et al, 2011 supra). Confirmation of select MS targets was performed via immunoblot analysis of NeutrAvidin enriched lysate as previously described (Carter-O'Connell et al, 2014 supra). Input controls are shown in FIGS. 9A and 9B.

Example 9

Chemistry

Chemical Synthesis: Synthesis of 6-a-NAD+ and 5-Et-6-a-NAD+ was completed as previously described (Carter-O'Connell et al, 2014 supra). C-5 substituted 6-a-NAD+ analogs were synthesized according to Scheme 1 below:

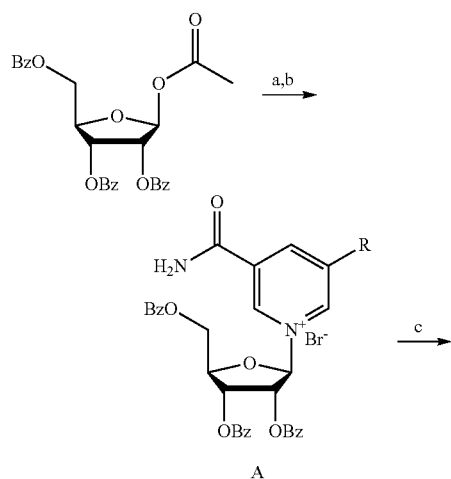

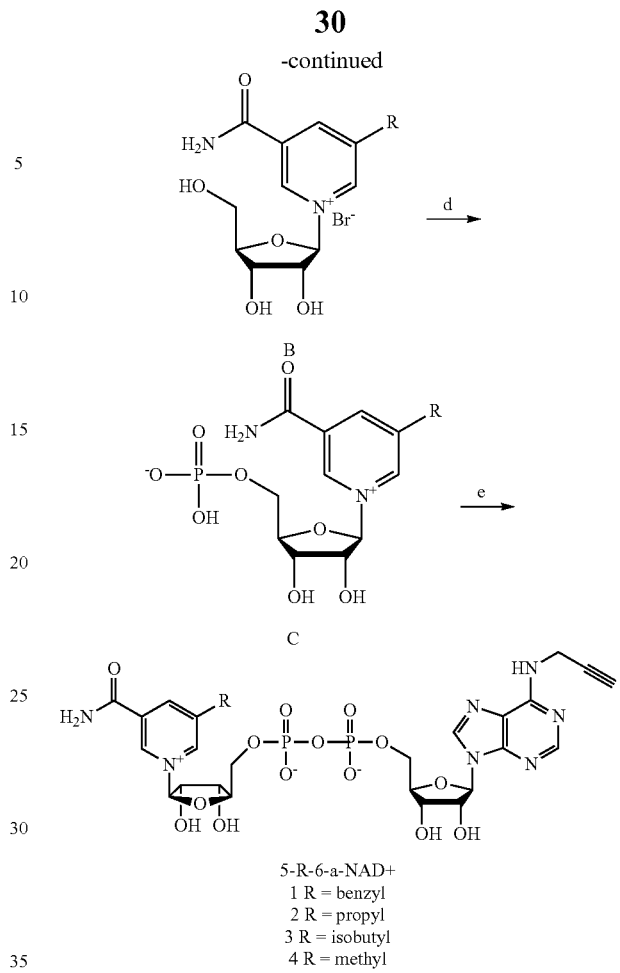

5-R-6-a-NAD+
1 R = benzyl
2 R = propyl
3 R = isobutyl
4 R = methyl

Reagents and conditions: (a) HBr (33 wt % in acetic acid), toluene, 0° C.; (b) C-5 substituted nicotinamide, MeCN; (c) 7N $NH_3$ in MeOH, −10° C.; (d) $POCl_3$, trimethyl phosphate, $H_2O$, rt; (e) 6-alkyne-AMP-morpholidate, $MnCl_2$, $MgSO_4$, formamide, rt.

General: $^1H$ and $^{13}C$ NMR were recorded on a Bruker DPX spectrometer at 400 MHz and 100 MHz, respectively. Chemical shifts are reported as parts per million (ppm) downfield from an internal tetramethylsilane standard or solvent references. For air- and water-sensitive reactions, glassware was oven-dried prior to use and reactions were performed under argon. Dichloromethane, dimethylformamide, and tetrahydrofuran were dried using the solvent purification system manufactured by Glass Contour, Inc. (Laguna Beach, Calif.). All other solvents were of ACS chemical grade (Fisher Scientific) and used without further purification unless otherwise indicated. Commercially available starting reagents were used without further purification. Nicotinamide (Sigma-Aldrich, >99.5%), and 5-methylnicotinamide (Alfa Aesar, 97%) were used without further purification. Analytical thin-layer chromatography was performed with silica gel 60 F254 glass plates (SiliCycle). Flash column chromatography was conducted with either pre-packed Redisep Rf normal/reverse phase columns (Teledyne ISCO) or self-packed columns containing 200-400 mesh silica gel (SiliCycle) on a Combiflash Companion purification system (Teledyne ISCO). High performance liquid chromatography (HPLC) was performed on a Varian Prostar 210 (Agilent) with a flow rate of 20 ml/min using Polaris 5

C18-A columns (150×4.6 mm, 3 mm-analytical, 150×21.2 mm, 5 mm preparative) (Agilent). UV-Vis detection: $\lambda 1=254$ nm, $\lambda 2=280$ nm.

General procedure for the synthesis of N'-(2,3,5-Tri-O-Benzoyl-β-D-ribofuranosyl)-3-aminocarbonyl-5-R-pyridinium bromide A. β-D-ribofuranose-acetate-2,3,5-tribenzoate (504 mg, 1 mmol) was dissolved in toluene (15 ml) and cooled to 0° C. HBr (33 wt % in acetic acid) (368 mg, 1.5 mmol) was added dropwise and the reaction was stirred at 0° C. for 2 h. 0.5 ml of the solution mixture was taken and evaporated to dryness for $^1$H NMR analysis [chemical shifts for the anomeric protons: β isomer=6.6 ppm (s, $^1$H); α isomer=6.9 ppm (d, $^1$H)]. After the starting material was consumed and $^1$H NMR confirmed the formation of the β isomer, the reaction was concentrated in vacuo. The crude β-D-ribofuranose-bromo-2,3,5-tribenzoate was azeotroped with toluene (3×20 ml) to remove remaining acetic acid and dried in vacuo for 2 h. Crude β-D-ribofuranosebromo-2,3,5-tribenzoate and appropriate C-5-substituted nicotinamide (90 mg, 0.55 mmol) (prepared as described previously: Carter-O'Connell et al., 2014 supra) was dissolved in ACN (40 ml). The reaction was stirred under Ar gas at rt for 2 days. The reaction was concentrated in vacuo (temperature kept below 35° C.). The crude product was dissolved in CHCl$_3$ (2 ml) and ppt by adding ethyl ether (10 ml). The entire procedure was repeated three times to yield the desired product, which was used in subsequent reactions without further purification. Yields: 1A: yield, 260 mg (58%), 2A: yield, 350 mg (92%), 3A: yield, 230 mg (60%), 4A: yield, 282 mg (77%).

General procedure for the synthesis of N'-(β-D-ribofuranosyl)-3-aminocarbonyl-5-R-pyridinium bromide B. A was dissolved in ammonia (25 ml, 7 N in MeOH) and the reaction was stirred at −10° C. for 36 h. The reaction was concentrated in vacuo and the crude product was dissolved in MeOH (1 ml). Addition of ethyl ether 10 ml) resulted in ppt of the desired product. The procedure was repeated three times to yield the desired product as an off white powder (90 mg, 66% yield), which was used in subsequent reactions without further purification. Some epimerization was observed (5-10% α isomer was present as determined by 1H NMR analysis).

1B: amount of 1A: 100 mg, 0.14 mmol; yield, 35 mg (60%). 1H NMR (400 MHz, D2O) δ 9.42 (s, 1H), 9.08 (s, 1H), 8.78 (d, J=1.7 Hz, 1H), 7.49-7.25 (m, 5H), 6.16 (d, J=4.1 Hz, 1H), 4.42 (dd, J=6.0, 3.4 Hz, 2H), 4.36-4.22 (m, 3H), 3.98 (dd, J=13.0, 2.9 Hz, 1H), 3.81 (dd, J=13.0, 3.5 Hz, 1H).

2B: amount of 2A: 250 mg, 0.36 mmol; yield, 90 mg (66%). 1H NMR (400 MHz, D20) δ 9.40 (s, 1H), 9.13 (s, 1H), 8.81 (s, 1H), 6.19 (d, J=4.2, 1H), 4.45 (m, 2H), 4.33 (m, 1H), 4.05 (ddd, J=13.0, 2.8, 1.7 Hz, 1H), 3.88 (ddd, J=12.9, 3.3, 1.7 Hz, 1H), 2.97 (t, J=7.5 Hz, 2H), 1.73 (q, J=7.5 Hz, 2H), 0.92 (t, J=7.5, 3H).

3B: amount of 3A: 140 mg, 0.20 mmol; yield, 62 mg (79%). 1H NMR (400 MHz, D20) δ 9.41 (s, 1H), 9.14 (s, 1H), 8.79 (s, 1H), 6.19 (d, J=4.2 Hz, 1H), 4.45 (t, J=4.3 Hz, 2H), 4.33 (d, J=5.1 Hz, 1H), 4.05 (d, J=13.2 Hz, 1H), 3.89 (d, J=12.9 Hz, 1H), 2.81 (d, J=7.2 Hz, 2H), 2.07-1.90 (m, 1H), 0.91 (d, J=6.6 Hz, 6H).

4B: amount of 4A: 140 mg, 0.20 mmol; yield, 71 mg (56%).

General procedure for the synthesis of 5-R-nicotinamide mononucleotide C. B was dissolved in trimethyl phosphate (0.18 ml) and the reaction was cooled to 0° C. POCl$_3$ (10 eq.) was added and the reaction was stirred at 0° C. for 4 h. A few drops H$_2$O was then added to quench the reaction. Trimethyl phosphate was removed by extraction with ethyl ether (20 ml). The remaining trimethyl phosphate was removed by a second extraction with THF (5 ml). The aqueous layer was concentrated in vacuo. The crude product was dissolved in H$_2$O (0.5 ml) and purified via two-step ion exchange chromatography (Dowex resin 1×2, formate resin, eluted with water; H$^+$ resin, eluted with water). Fractions containing the desired product were pooled and concentrated in vacuo to yield the desired product (54 mg, 60% yield).

1C: amount of 1B: 30 mg (0.07 mmol); yield, 24 mg (80%). $^1$H NMR (400 MHz, D$_2$O) δ 9.28 (s, 1H), 9.03 (s, 1H), 8.70 (s, 1H), 7.30 (d, J=7.6 Hz, 5H), 6.13-6.03 (m, 1H), 4.57 (s, 1H), 4.48 (d, J=4.4 Hz, 1H), 4.42-4.34 (m, 1H), 4.31 (s, 2H), 4.29-4.15 (m, 1H), 4.08 (d, J=11.6 Hz, 1H).

2C: amount of 2B: 90 mg, 0.24 mmol; yield, 54 mg (60%).1H NMR (400 MHz, D2O) δ 9.40 (s, 1H), 9.13 (s, 1H), 8.81 (s, 1H), 6.19 (d, J=4.2, 1H), 4.45 (m, 2H), 4.33 (m, 1H), 4.05 (ddd, J=13.0, 2.8, 1.7 Hz, 1H), 3.88 (ddd, J=12.9, 3.3, 1.7 Hz, 1H), 2.97 (t, J=7.5 Hz, 2H), 1.73 (q, J=7.5 Hz, 2H), 0.92 (t, J=7.5, 3H).

3C: amount of 3B: 100 mg, 0.3 mmol; yield, 74 mg (74%). 1H NMR (400 MHz, D2O) δ 9.35 (s, 1H), 9.01 (s, 1H), 8.80 (d, J=1.7 Hz, 1H), 6.13 (d, J=5.8 Hz, 1H), 4.61 (d, J=2.4 Hz, 1H), 4.52 (t, J=5.4 Hz, 1H), 4.43 (dd, J=5.0, 2.2 Hz, 1H), 4.34-4.19 (m, 1H), 4.18-4.05 (m, 1H), 2.83 (d, J=7.2 Hz, 2H), 2.00 (m, 1H), 0.91 (dd, J=6.6, 4.9 Hz 6H).

4C: amount of 4B: 60 mg, 0.17 mmol; yield, 22 mg (37%). 1H NMR (400 MHz, D$_2$O) δ 9.23 (s, 1H), 9.07 (s, 1H), 8.76 (s, 1H), 6.11 (dd, J=5.6, 2.4 Hz, 1H), 4.58 (p, J=2.5 Hz, 1H), 4.50 (td, J=5.2, 2.5 Hz, 1H), 4.40 (dt, J=5.3, 2.7 Hz, 1H), 4.27 (ddd, J=11.8, 4.5, 2.5 Hz, 1H), 4.16-3.99 (m, 1H), 2.60 (s, 3H).

General procedure for the synthesis of 5-R-6-a-NAD$^+$ analogues: the appropriate C-5-substituted nicotinamide mononucleotide C, 6-alkyne-AMP-morpholidate (1 eq.) (prepared as described previously: Carter-O'Connell et al, 2014 supra), and MgSO$_4$ (16 mg) were dissolved in a solution of MnCl$_2$ (0.5 ml, 0.2 M in formamide) and stirred at rt for 48 h. The reaction was concentrated in vacuo and the crude product was purified via preparative HPLC (MP A: 0.1% formic acid (aq), MP B: 0.1% formic acid in ACN; 0-5 min: 0-10% B, 5-8 min: 10-15% B, 8-10 min: 15-20% B, 10-12 min: 20-50% B). Fractions containing the desired product were pooled and concentrated in vacuo to yield the desired product.

5-benzyl-6-a-NAD+: amount of 1C: 11 mg (0.02 mmol); yield, 5 mg (32%). 1H NMR (400 MHz, D2O) δ 9.11 (s, 1H), 8.98 (s, 1H), 8.55 (s, 1H), 8.37 (s, 1H), 8.14 (s, 1H), 7.41-7.09 (m, 5H), 5.96 (t, J=5.0 Hz, 2H), 4.74-4.57 (m, 7H), 4.55-4.35 (m, 3H), 4.35-4.08 (m, 5H), 2.58 (s, 1H).

5-propyl-6-a-NAD+: amount of 2C: 24 mg (0.05 mmol); yield, 10 mg (27%). 1H NMR (400 MHz, D2O) δ 9.18 (s, 1H), 8.94 (s, 1H), 8.74 (s, 1H), 8.51 (s, 1H), 8.31 (s, 1H), 6.04 (dd, J=17.2, 5.6 Hz, 2H), 4.72 (m, 1H), 4.60-4.28 (m, 6H), 4.29-4.09 (m, 3H), 2.86 (t, J=7.6 Hz, 2H), 2.70(s, 1H) 1.68 (dt, J=14.5, 7.2 Hz, 2H), 0.91 (t, J=7.3 Hz, 3H).

5-isobutyl-6-a-NAD+: amount of 3C: 10 mg (0.02 mmol); yield, 8.9 mg (56%). 1H NMR (400 MHz, D2O) δ 9.24 (s, 1H), 8.94 (s, 1H), 8.80-8.69 (m, 1H), 8.61-8.49 (m, 1H), 8.34 (s, 1H), 6.07 (dd, J=16.4, 5.4 Hz, 2H), 4.72 (dd, J=6.6, 4.1 Hz, 1H), 4.65-4.30 (m, 4H), 4.24 (d, J=14.9 Hz, 3H), 2.78 (d, J=6.9 Hz, 2H), 2.71(s, 1H), 1.96 (dd, J=13.6, 6.8 Hz, 1H), 0.88 (dd, J=6.5, 4.3 Hz, 6H).

5-methyl-6-a-NAD+: amount of 4C: 26 mg (0.05 mmol); yield, 9 mg (25%). 1H NMR (400 MHz, D20) δ 9.08 (s, 1H), 8.91 (s, 1H), 8.65 (s, 1H), 8.44 (s, 1H), 8.17 (s, 1H), 5.97 (dd, J=18.7, 5.6 Hz, 2H), 4.70-4.56 (m, 1H), 4.53-4.24 (m, 5H), 4.24-4.00 (m, 4H), 2.55 (s, 3H).

The invention claimed is:

1. A method of identifying a protein target of a mono-PARP, the method comprising: contacting a small molecule compound (SMC) of formula:

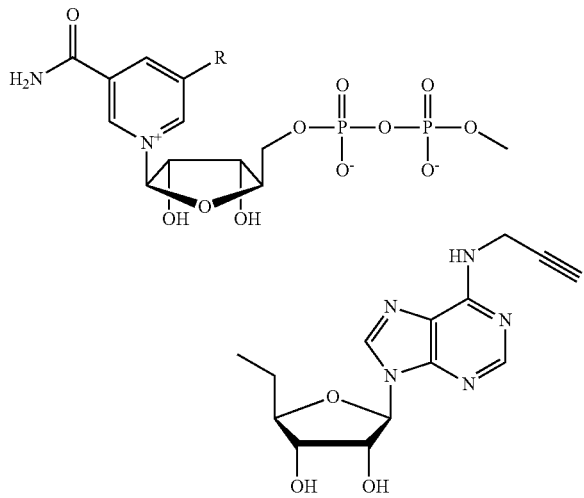

wherein R is alkyl or aryl, with a protein, said protein comprising a polypeptide comprising a mono-poly-ADP-ribose-polymerases (PARP) catalytic domain comprising SEQ ID NO: 15, and wherein the polypeptide catalyzes the addition of the SMC to a PARP protein target, wherein said contacting occurs within a living cell; subjecting the cell to conditions that result in the protein catalyzing the reaction by which the SMC is covalently attached to one or more cellular proteins; and identifying the one or more cellular proteins to which the SMC is covalently attached as the protein target(s) of the mono-PARP.

2. The method of claim 1, wherein the SMC comprises 5-Bn-6-a-NAD+.

3. The method of claim 1, further comprising conjugating a label to the SMC.

4. The method of claim 3, wherein the label comprises biotin or a fluorescent molecule.

5. The method of claim 1, further comprising detecting the one or more cellular proteins to which the SMC is covalently attached via a method that comprises mass spectrometry.

6. The method of claim 1, wherein R is aryl.

7. The method of claim 6, wherein R is benzyl.

8. The method of claim 1, wherein R is alkyl.

9. The method of claim 8, wherein R is $C_{1-6}$ alkyl.

10. The method of claim 9, wherein R is selected from the group of methyl, isobutyl, and propyl.

* * * * *

SEQUENCE LISTING

<160> NUMBER OF SEQ ID NOS: 64

<210> SEQ ID NO 1
<211> LENGTH: 125
<212> TYPE: PRT
<213> ORGANISM: Homo sapiens
<220> FEATURE:
<221> NAME/KEY: misc_feature
<222> LOCATION: (112)..(112)
<223> OTHER INFORMATION: Xaa can be any naturally occurring amino acid

<400> SEQUENCE: 1

```
Phe Ala Phe His Gly Ser His Ile Glu Asn Trp His Ser Ile Leu Arg
1               5                   10                  15

Asn Gly Leu Val Asn Ala Ser Tyr Thr Lys Leu Gln Leu His Gly Ala
            20                  25                  30

Ala Tyr Gly Lys Gly Ile Tyr Leu Ser Pro Ile Ser Ser Ile Ser Phe
        35                  40                  45

Gly Tyr Ser Gly Met Gly Lys Gly Gln His Arg Met Pro Ser Lys Asp
    50                  55                  60

Glu Leu Val Gln Arg Tyr Asn Arg Met Asn Thr Ile Pro Gln Thr Arg
65                  70                  75                  80

Ser Ile Gln Ser Arg Phe Leu Gln Ser Arg Asn Leu Asn Cys Ile Ala
                85                  90                  95

Leu Cys Glu Val Ile Thr Ser Lys Asp Leu Gln Lys His Gly Asn Xaa
            100                 105                 110

Trp Val Cys Pro Val Ser Asp His Val Cys Thr Arg Phe
        115                 120                 125
```

<210> SEQ ID NO 2
<211> LENGTH: 183
<212> TYPE: PRT
<213> ORGANISM: Homo sapiens
<220> FEATURE:
<221> NAME/KEY: misc_feature
<222> LOCATION: (166)..(166)
<223> OTHER INFORMATION: Xaa can be any naturally occurring amino acid

<400> SEQUENCE: 2

```
Pro Val Ser Ala Glu Asp Lys Ser Tyr Arg Ile Ile Tyr Asn Leu Phe
1               5                   10                  15

His Lys Thr Val Pro Glu Phe Lys Tyr Arg Ile Leu Gln Ile Leu Arg
            20                  25                  30

Val Gln Asn Gln Phe Leu Trp Glu Lys Tyr Lys Arg Lys Lys Glu Tyr
        35                  40                  45

Met Asn Arg Lys Met Phe Gly Arg Asp Arg Ile Ile Asn Glu Arg His
    50                  55                  60

Leu Phe His Gly Thr Ser Gln Asp Val Val Asp Gly Ile Cys Lys His
65                  70                  75                  80

Asn Phe Asp Pro Arg Val Cys Gly Lys His Ala Thr Met Phe Gly Gln
                85                  90                  95

Gly Ser Tyr Phe Ala Lys Lys Ala Ser Tyr Ser His Asn Phe Ser Lys
            100                 105                 110

Lys Ser Ser Lys Gly Val His Phe Met Phe Leu Ala Lys Val Leu Thr
        115                 120                 125

Gly Arg Tyr Thr Met Gly Ser His Gly Met Arg Arg Pro Pro Pro Val
    130                 135                 140
```

```
Asn Pro Gly Ser Val Thr Ser Asp Leu Tyr Asp Ser Cys Val Asp Asn
145                 150                 155                 160

Phe Phe Glu Pro Gln Xaa Phe Val Ile Phe Asn Asp Asp Gln Ser Tyr
                165                 170                 175

Pro Tyr Phe Val Ile Gln Tyr
            180
```

<210> SEQ ID NO 3
<211> LENGTH: 185
<212> TYPE: PRT
<213> ORGANISM: Homo sapiens
<220> FEATURE:
<221> NAME/KEY: misc_feature
<222> LOCATION: (168)..(168)
<223> OTHER INFORMATION: Xaa can be any naturally occurring amino acid

<400> SEQUENCE: 3

```
Leu Glu Arg Leu Ala Glu Asn Thr Gly Glu Phe Gln Glu Val Val Arg
1               5                   10                  15

Ala Phe Tyr Asp Thr Leu Asp Ala Ala Arg Ser Ser Ile Arg Val Val
                20                  25                  30

Arg Val Glu Arg Val Ser His Pro Leu Leu Gln Gln Gln Tyr Glu Leu
            35                  40                  45

Tyr Arg Glu Arg Leu Leu Gln Arg Cys Glu Arg Pro Val Glu Gln
50                  55                  60

Val Leu Tyr His Gly Thr Thr Ala Pro Ala Val Pro Asp Ile Cys Ala
65                  70                  75                  80

His Gly Phe Asn Arg Ser Phe Cys Gly Arg Asn Ala Thr Val Tyr Gly
                85                  90                  95

Lys Gly Val Tyr Phe Ala Arg Arg Ala Ser Leu Ser Val Gln Asp Arg
                100                 105                 110

Tyr Ser Pro Pro Asn Ala Asp Gly His Lys Ala Val Phe Val Ala Arg
            115                 120                 125

Val Leu Thr Gly Asp Tyr Gly Gln Gly Arg Arg Gly Leu Arg Ala Pro
130                 135                 140

Pro Leu Arg Gly Pro Gly His Val Leu Leu Arg Tyr Asp Ser Ala Val
145                 150                 155                 160

Asp Cys Ile Cys Gln Pro Ser Xaa Phe Val Ile Phe His Asp Thr Gln
                165                 170                 175

Ala Leu Pro Thr His Leu Ile Thr Cys
            180                 185
```

<210> SEQ ID NO 4
<211> LENGTH: 138
<212> TYPE: PRT
<213> ORGANISM: Homo sapiens
<220> FEATURE:
<221> NAME/KEY: misc_feature
<222> LOCATION: (120)..(120)
<223> OTHER INFORMATION: Xaa can be any naturally occurring amino acid

<400> SEQUENCE: 4

```
Met Leu Phe His Gly Thr Ser Ser Glu Phe Val Glu Ala Ile Cys Ile
1               5                   10                  15

His Asn Phe Asp Trp Arg Ile Asn Gly Ile His Gly Ala Val Phe Gly
                20                  25                  30

Lys Gly Thr Tyr Phe Ala Arg Asp Ala Ala Tyr Ser Ser Arg Phe Cys
            35                  40                  45
```

```
Lys Asp Asp Ile Lys His Gly Asn Thr Phe Gln Ile His Gly Val Ser
 50                  55                  60
Leu Gln Gln Arg His Leu Phe Arg Thr Tyr Lys Ser Met Phe Leu Ala
 65                  70                  75                  80
Arg Val Leu Ile Gly Asp Tyr Ile Asn Gly Asp Ser Lys Tyr Met Arg
                 85                  90                  95
Pro Pro Ser Lys Asp Gly Ser Tyr Val Asn Leu Tyr Asp Ser Cys Val
                100                 105                 110
Asp Asp Thr Trp Asn Pro Lys Xaa Phe Val Val Phe Ala Asn Gln
                115                 120                 125
Ile Tyr Pro Glu Tyr Leu Ile Asp Phe His
130                 135
```

<210> SEQ ID NO 5
<211> LENGTH: 181
<212> TYPE: PRT
<213> ORGANISM: Homo sapiens
<220> FEATURE:
<221> NAME/KEY: misc_feature
<222> LOCATION: (164)..(164)
<223> OTHER INFORMATION: Xaa can be any naturally occurring amino acid

<400> SEQUENCE: 5

```
Gly Phe Gln Lys Ile Thr Leu Ser Ser Ser Glu Glu Tyr Gln Lys
  1               5                  10                  15
Val Trp Asn Leu Phe Asn Arg Thr Leu Pro Phe Tyr Phe Val Gln Lys
                 20                  25                  30
Ile Glu Arg Val Gln Asn Leu Ala Leu Trp Glu Val Tyr Gln Trp Gln
                 35                  40                  45
Lys Gly Gln Met Gln Lys Gln Asn Gly Gly Lys Ala Val Asp Glu Arg
 50                  55                  60
Gln Leu Phe His Gly Thr Ser Ala Ile Phe Val Asp Ala Ile Cys Gln
 65                  70                  75                  80
Gln Asn Phe Asp Trp Arg Val Cys Gly Val His Gly Thr Ser Tyr Gly
                 85                  90                  95
Lys Gly Ser Tyr Phe Ala Arg Asp Ala Ala Tyr Ser His His Tyr Ser
                100                 105                 110
Lys Ser Asp Thr Gln Thr His Thr Met Phe Leu Ala Arg Val Leu Val
                115                 120                 125
Gly Glu Phe Val Arg Gly Asn Ala Ser Phe Val Arg Pro Pro Ala Lys
                130                 135                 140
Glu Gly Trp Ser Asn Ala Phe Tyr Asp Ser Cys Val Asn Ser Val Ser
145                 150                 155                 160
Asp Pro Ser Xaa Phe Val Ile Phe Glu Lys His Gln Val Tyr Pro Glu
                165                 170                 175
Tyr Val Ile Gln Tyr
                180
```

<210> SEQ ID NO 6
<211> LENGTH: 183
<212> TYPE: PRT
<213> ORGANISM: Homo sapiens
<220> FEATURE:
<221> NAME/KEY: misc_feature
<222> LOCATION: (165)..(165)
<223> OTHER INFORMATION: Xaa can be any naturally occurring amino acid

<400> SEQUENCE: 6

```
Cys Val Val Glu Leu Leu Pro Ser Asp Pro Glu Tyr Asn Thr Val Ala
```

```
1               5                   10                  15
Ser Lys Phe Asn Gln Thr Cys Ser His Phe Arg Ile Glu Lys Ile Glu
            20                  25                  30

Arg Ile Gln Asn Pro Asp Leu Trp Asn Ser Tyr Gln Ala Lys Lys Lys
            35                  40                  45

Thr Met Asp Ala Lys Asn Gly Gln Thr Met Asn Glu Lys Gln Leu Phe
        50                  55                  60

His Gly Thr Asp Ala Gly Ser Val Pro His Val Asn Arg Asn Gly Phe
65                  70                  75                  80

Asn Arg Ser Tyr Ala Gly Lys Asn Ala Val Ala Tyr Gly Lys Gly Thr
                85                  90                  95

Tyr Phe Ala Val Asn Ala Asn Tyr Ser Ala Asn Asp Thr Tyr Ser Arg
            100                 105                 110

Pro Asp Ala Asn Gly Arg Lys His Val Tyr Tyr Val Arg Val Leu Thr
            115                 120                 125

Gly Ile Tyr Thr His Gly Asn His Ser Leu Ile Val Pro Pro Ser Lys
        130                 135                 140

Asn Pro Gln Asn Pro Thr Asp Leu Tyr Asp Thr Val Thr Asp Asn Val
145                 150                 155                 160

His His Pro Ser Xaa Phe Val Ala Phe Tyr Asp Gln Ala Tyr Pro
                165                 170                 175

Glu Tyr Leu Ile Thr Phe Arg
            180
```

<210> SEQ ID NO 7
<211> LENGTH: 178
<212> TYPE: PRT
<213> ORGANISM: Homo sapiens
<220> FEATURE:
<221> NAME/KEY: misc_feature
<222> LOCATION: (161)..(161)
<223> OTHER INFORMATION: Xaa can be any naturally occurring amino acid

<400> SEQUENCE: 7

```
Leu Glu Pro Gly Gln Ser Glu Tyr Asn Thr Ile Lys Asp Lys Phe Thr
1               5                   10                  15

Arg Thr Cys Ser Ser Tyr Ala Ile Glu Lys Ile Glu Arg Ile Gln Asn
            20                  25                  30

Ala Phe Leu Trp Gln Ser Tyr Gln Val Lys Lys Arg Gln Met Asp Ile
            35                  40                  45

Lys Asn Asp His Lys Asn Asn Glu Arg Leu Leu Phe His Gly Thr Asp
        50                  55                  60

Ala Asp Ser Val Pro Tyr Val Asn Gln His Gly Phe Asn Arg Ser Cys
65                  70                  75                  80

Ala Gly Lys Asn Ala Val Ser Tyr Gly Lys Gly Thr Tyr Phe Ala Val
                85                  90                  95

Asp Ala Ser Tyr Ser Ala Lys Asp Thr Tyr Ser Lys Pro Asp Ser Asn
            100                 105                 110

Gly Arg Lys His Met Tyr Val Val Arg Val Leu Thr Gly Val Phe Thr
            115                 120                 125

Lys Gly Arg Ala Gly Leu Val Thr Pro Pro Lys Asn Pro His Asn
        130                 135                 140

Pro Thr Asp Leu Phe Asp Ser Val Thr Asn Asn Thr Arg Ser Pro Lys
145                 150                 155                 160

Xaa Phe Val Val Phe Phe Asp Asn Gln Ala Tyr Pro Glu Tyr Leu Ile
                165                 170                 175
```

Thr Phe

```
<210> SEQ ID NO 8
<211> LENGTH: 179
<212> TYPE: PRT
<213> ORGANISM: Homo sapiens
<220> FEATURE:
<221> NAME/KEY: misc_feature
<222> LOCATION: (160)..(160)
<223> OTHER INFORMATION: Xaa can be any naturally occurring amino acid
```

<400> SEQUENCE: 8

Leu Thr Ile His Ser Ala Gly Lys Ala Glu Phe Glu Lys Ile Gln Lys
1               5                   10                  15

Leu Thr Gly Ala Pro His Thr Pro Val Pro Ala Pro Asp Phe Leu Phe
            20                  25                  30

Glu Ile Glu Tyr Phe Asp Pro Ala Asn Ala Lys Phe Tyr Glu Thr Lys
        35                  40                  45

Gly Glu Arg Asp Leu Ile Tyr Ala Phe His Gly Ser Arg Leu Glu Asn
    50                  55                  60

Phe His Ser Ile Ile His Asn Gly Leu His Cys His Leu Asn Lys Thr
65                  70                  75                  80

Ser Leu Phe Gly Glu Gly Thr Tyr Leu Thr Ser Asp Leu Ser Leu Ala
                85                  90                  95

Leu Ile Tyr Ser Pro His Gly His Gly Trp Gln His Ser Leu Leu Gly
            100                 105                 110

Pro Ile Leu Ser Cys Val Ala Val Cys Glu Val Ile Asp His Pro Asp
        115                 120                 125

Val Lys Cys Gln Thr Lys Lys Lys Asp Ser Lys Glu Ile Asp Arg Arg
    130                 135                 140

Arg Ala Arg Ile Lys His Ser Glu Gly Gly Asp Ile Pro Pro Lys Xaa
145                 150                 155                 160

Phe Val Val Thr Asn Asn Gln Leu Leu Arg Val Lys Tyr Leu Leu Val
                165                 170                 175

Tyr Ser Gln

```
<210> SEQ ID NO 9
<211> LENGTH: 125
<212> TYPE: PRT
<213> ORGANISM: Homo sapiens
```

<400> SEQUENCE: 9

Phe Ala Phe His Gly Ser His Ile Glu Asn Trp His Ser Ile Leu Arg
1               5                   10                  15

Asn Gly Leu Val Asn Ala Ser Tyr Thr Lys Leu Gln Leu His Gly Ala
            20                  25                  30

Ala Tyr Gly Lys Gly Ile Tyr Leu Ser Pro Ile Ser Ser Ile Ser Phe
        35                  40                  45

Gly Tyr Ser Gly Met Gly Lys Gly Gln His Arg Met Pro Ser Lys Asp
    50                  55                  60

Glu Leu Val Gln Arg Tyr Asn Arg Met Asn Thr Ile Pro Gln Thr Arg
65                  70                  75                  80

Ser Ile Gln Ser Arg Phe Leu Gln Ser Arg Asn Leu Asn Cys Ile Ala
                85                  90                  95

Leu Cys Glu Val Ile Thr Ser Lys Asp Leu Gln Lys His Gly Asn Gly
            100                 105                 110

```
Trp Val Cys Pro Val Ser Asp His Val Cys Thr Arg Phe
        115                 120                 125
```

<210> SEQ ID NO 10
<211> LENGTH: 125
<212> TYPE: PRT
<213> ORGANISM: Homo sapiens

<400> SEQUENCE: 10

```
Phe Ala Phe His Gly Ser His Ile Glu Asn Trp His Ser Ile Leu Arg
1               5                   10                  15

Asn Gly Leu Val Asn Ala Ser Tyr Thr Lys Leu Gln Leu His Gly Ala
            20                  25                  30

Ala Tyr Gly Lys Gly Ile Tyr Leu Ser Pro Ile Ser Ser Ile Ser Phe
        35                  40                  45

Gly Tyr Ser Gly Met Gly Lys Gly Gln His Arg Met Pro Ser Lys Asp
    50                  55                  60

Glu Leu Val Gln Arg Tyr Asn Arg Met Asn Thr Ile Pro Gln Thr Arg
65                  70                  75                  80

Ser Ile Gln Ser Arg Phe Leu Gln Ser Arg Asn Leu Asn Cys Ile Ala
                85                  90                  95

Leu Cys Glu Val Ile Thr Ser Lys Asp Leu Gln Lys His Gly Asn Ala
            100                 105                 110

Trp Val Cys Pro Val Ser Asp His Val Cys Thr Arg Phe
        115                 120                 125
```

<210> SEQ ID NO 11
<211> LENGTH: 183
<212> TYPE: PRT
<213> ORGANISM: Homo sapiens

<400> SEQUENCE: 11

```
Pro Val Ser Ala Glu Asp Lys Ser Tyr Arg Ile Ile Tyr Asn Leu Phe
1               5                   10                  15

His Lys Thr Val Pro Glu Phe Lys Tyr Arg Ile Leu Gln Ile Leu Arg
            20                  25                  30

Val Gln Asn Gln Phe Leu Trp Glu Lys Tyr Lys Arg Lys Lys Glu Tyr
        35                  40                  45

Met Asn Arg Lys Met Phe Gly Arg Asp Arg Ile Ile Asn Glu Arg His
    50                  55                  60

Leu Phe His Gly Thr Ser Gln Asp Val Asp Gly Ile Cys Lys His Asn
65                  70                  75                  80

Asn Phe Asp Pro Arg Val Cys Gly Lys His Ala Thr Met Phe Gly Gln
                85                  90                  95

Gly Ser Tyr Phe Ala Lys Lys Ala Ser Tyr Ser His Asn Phe Ser Lys
            100                 105                 110

Lys Ser Ser Lys Gly Val His Phe Met Phe Leu Ala Lys Val Leu Thr
        115                 120                 125

Gly Arg Tyr Thr Met Gly Ser His Gly Met Arg Arg Pro Pro Pro Val
    130                 135                 140

Asn Pro Gly Ser Val Thr Ser Asp Leu Tyr Asp Ser Cys Val Asp Asn
145                 150                 155                 160

Phe Phe Glu Pro Gln Gly Phe Val Ile Phe Asn Asp Gln Ser Tyr
                165                 170                 175

Pro Tyr Phe Val Ile Gln Tyr
            180
```

<210> SEQ ID NO 12
<211> LENGTH: 183
<212> TYPE: PRT
<213> ORGANISM: Homo sapiens

<400> SEQUENCE: 12

Pro Val Ser Ala Glu Asp Lys Ser Tyr Arg Ile Ile Tyr Asn Leu Phe
1               5                   10                  15

His Lys Thr Val Pro Glu Phe Lys Tyr Arg Ile Leu Gln Ile Leu Arg
            20                  25                  30

Val Gln Asn Gln Phe Leu Trp Glu Lys Tyr Lys Arg Lys Lys Glu Tyr
        35                  40                  45

Met Asn Arg Lys Met Phe Gly Arg Asp Arg Ile Ile Asn Glu Arg His
50                  55                  60

Leu Phe His Gly Thr Ser Gln Asp Val Val Asp Gly Ile Cys Lys His
65                  70                  75                  80

Asn Phe Asp Pro Arg Val Cys Gly Lys His Ala Thr Met Phe Gly Gln
                85                  90                  95

Gly Ser Tyr Phe Ala Lys Lys Ala Ser Tyr Ser His Asn Phe Ser Lys
            100                 105                 110

Lys Ser Lys Gly Val His Phe Met Phe Leu Ala Lys Val Leu Thr
        115                 120                 125

Gly Arg Tyr Thr Met Gly Ser His Gly Met Arg Pro Pro Val
130                 135                 140

Asn Pro Gly Ser Val Thr Ser Asp Leu Tyr Asp Ser Cys Val Asp Asn
145                 150                 155                 160

Phe Phe Glu Pro Gln Ala Phe Val Ile Phe Asn Asp Asp Gln Ser Tyr
                165                 170                 175

Pro Tyr Phe Val Ile Gln Tyr
            180

<210> SEQ ID NO 13
<211> LENGTH: 125
<212> TYPE: PRT
<213> ORGANISM: Homo sapiens

<400> SEQUENCE: 13

Phe Ala Phe His Gly Ser His Ile Glu Asn Trp His Ser Ile Leu Arg
1               5                   10                  15

Asn Gly Leu Val Val Ala Ser Asn Thr Arg Leu Gln Leu His Gly Ala
            20                  25                  30

Met Tyr Gly Ser Gly Ile Tyr Leu Ser Pro Met Ser Ser Ile Ser Phe
        35                  40                  45

Gly Tyr Ser Gly Met Asn Lys Lys Gln Lys Val Ser Ala Lys Asp Glu
50                  55                  60

Pro Ala Ser Ser Lys Ser Ser Asn Thr Ser Gln Ser Gln Lys Lys
65                  70                  75                  80

Gly Gln Gln Ser Gln Phe Leu Gln Ser Arg Asn Leu Lys Cys Ile Ala
            85                  90                  95

Leu Cys Glu Val Ile Thr Ser Ser Asp Leu His Lys His Gly Glu Gly
            100                 105                 110

Trp Val Val Pro Asn Thr Asp His Val Cys Thr Arg Phe
        115                 120                 125

<210> SEQ ID NO 14
<211> LENGTH: 125

```
<212> TYPE: PRT
<213> ORGANISM: Homo sapiens

<400> SEQUENCE: 14

Phe Ala Phe His Gly Ser His Ile Glu Asn Trp His Ser Ile Leu Arg
1               5                   10                  15

Asn Gly Leu Val Val Ala Ser Asn Thr Arg Leu Gln Leu His Gly Ala
            20                  25                  30

Met Tyr Gly Ser Gly Ile Tyr Leu Ser Pro Met Ser Ser Ile Ser Phe
        35                  40                  45

Gly Tyr Ser Gly Met Asn Lys Lys Gln Lys Val Ser Ala Lys Asp Glu
    50                  55                  60

Pro Ala Ser Ser Lys Ser Ser Asn Thr Ser Gln Ser Gln Lys Lys
65                  70                  75                  80

Gly Gln Gln Ser Gln Phe Leu Gln Ser Arg Asn Leu Lys Cys Ile Ala
                85                  90                  95

Leu Cys Glu Val Ile Thr Ser Ser Asp Leu His Lys His Gly Glu Ala
            100                 105                 110

Trp Val Val Pro Asn Thr Asp His Val Cys Thr Arg Phe
            115                 120                 125

<210> SEQ ID NO 15
<211> LENGTH: 185
<212> TYPE: PRT
<213> ORGANISM: Homo sapiens

<400> SEQUENCE: 15

Leu Glu Arg Leu Ala Glu Asn Thr Gly Glu Phe Gln Glu Val Val Arg
1               5                   10                  15

Ala Phe Tyr Asp Thr Leu Asp Ala Ala Arg Ser Ser Ile Arg Val Val
            20                  25                  30

Arg Val Glu Arg Val Ser His Pro Leu Leu Gln Gln Gln Tyr Glu Leu
        35                  40                  45

Tyr Arg Glu Arg Leu Leu Gln Arg Cys Glu Arg Arg Pro Val Glu Gln
    50                  55                  60

Val Leu Tyr His Gly Thr Thr Ala Pro Ala Val Pro Asp Ile Cys Ala
65                  70                  75                  80

His Gly Phe Asn Arg Ser Phe Cys Gly Arg Asn Ala Thr Val Tyr Gly
                85                  90                  95

Lys Gly Val Tyr Phe Ala Arg Arg Ala Ser Leu Ser Val Gln Asp Arg
            100                 105                 110

Tyr Ser Pro Pro Asn Ala Asp Gly His Lys Ala Val Phe Val Ala Arg
            115                 120                 125

Val Leu Thr Gly Asp Tyr Gly Gln Gly Arg Arg Gly Leu Arg Ala Pro
        130                 135                 140

Pro Leu Arg Gly Pro Gly His Val Leu Leu Arg Tyr Asp Ser Ala Val
145                 150                 155                 160

Asp Cys Ile Cys Gln Pro Ser Gly Phe Val Ile Phe His Asp Thr Gln
                165                 170                 175

Ala Leu Pro Thr His Leu Ile Thr Cys
            180                 185

<210> SEQ ID NO 16
<211> LENGTH: 185
<212> TYPE: PRT
<213> ORGANISM: Homo sapiens
```

<400> SEQUENCE: 16

Leu Glu Arg Leu Ala Glu Asn Thr Gly Glu Phe Gln Glu Val Val Arg
1               5                   10                  15

Ala Phe Tyr Asp Thr Leu Asp Ala Ala Arg Ser Ser Ile Arg Val Val
            20                  25                  30

Arg Val Glu Arg Val Ser His Pro Leu Leu Gln Gln Gln Tyr Glu Leu
        35                  40                  45

Tyr Arg Glu Arg Leu Leu Gln Arg Cys Glu Arg Pro Val Glu Gln
    50                  55                  60

Val Leu Tyr His Gly Thr Thr Ala Pro Ala Val Pro Asp Ile Cys Ala
65                  70                  75                  80

His Gly Phe Asn Arg Ser Phe Cys Gly Arg Asn Ala Thr Val Tyr Gly
                85                  90                  95

Lys Gly Val Tyr Phe Ala Arg Arg Ala Ser Leu Ser Val Gln Asp Arg
            100                 105                 110

Tyr Ser Pro Pro Asn Ala Asp Gly His Lys Ala Val Phe Val Ala Arg
            115                 120                 125

Val Leu Thr Gly Asp Tyr Gly Gln Gly Arg Arg Gly Leu Arg Ala Pro
130                 135                 140

Pro Leu Arg Gly Pro Gly His Val Leu Leu Arg Tyr Asp Ser Ala Val
145                 150                 155                 160

Asp Cys Ile Cys Gln Pro Ser Ala Phe Val Ile Phe His Asp Thr Gln
                165                 170                 175

Ala Leu Pro Thr His Leu Ile Thr Cys
            180                 185

<210> SEQ ID NO 17
<211> LENGTH: 138
<212> TYPE: PRT
<213> ORGANISM: Homo sapiens

<400> SEQUENCE: 17

Met Leu Phe His Gly Thr Ser Ser Glu Phe Val Glu Ala Ile Cys Ile
1               5                   10                  15

His Asn Phe Asp Trp Arg Ile Asn Gly Ile His Gly Ala Val Phe Gly
            20                  25                  30

Lys Gly Thr Tyr Phe Ala Arg Asp Ala Ala Tyr Ser Ser Arg Phe Cys
        35                  40                  45

Lys Asp Asp Ile Lys His Gly Asn Thr Phe Gln Ile His Gly Val Ser
    50                  55                  60

Leu Gln Gln Arg His Leu Phe Arg Thr Tyr Lys Ser Met Phe Leu Ala
65                  70                  75                  80

Arg Val Leu Ile Gly Asp Tyr Ile Asn Gly Asp Ser Lys Tyr Met Arg
                85                  90                  95

Pro Pro Ser Lys Asp Gly Ser Tyr Val Asn Leu Tyr Asp Ser Cys Val
            100                 105                 110

Asp Asp Thr Trp Asn Pro Lys Gly Phe Val Val Phe Asp Ala Asn Gln
            115                 120                 125

Ile Tyr Pro Glu Tyr Leu Ile Asp Phe His
130                 135

<210> SEQ ID NO 18
<211> LENGTH: 138
<212> TYPE: PRT
<213> ORGANISM: Homo sapiens

```
<400> SEQUENCE: 18

Met Leu Phe His Gly Thr Ser Ser Glu Phe Val Glu Ala Ile Cys Ile
1               5                   10                  15

His Asn Phe Asp Trp Arg Ile Asn Gly Ile His Gly Ala Val Phe Gly
            20                  25                  30

Lys Gly Thr Tyr Phe Ala Arg Asp Ala Ala Tyr Ser Ser Arg Phe Cys
        35                  40                  45

Lys Asp Asp Ile Lys His Gly Asn Thr Phe Gln Ile His Gly Val Ser
    50                  55                  60

Leu Gln Gln Arg His Leu Phe Arg Thr Tyr Lys Ser Met Phe Leu Ala
65                  70                  75                  80

Arg Val Leu Ile Gly Asp Tyr Ile Asn Gly Asp Ser Lys Tyr Met Arg
                85                  90                  95

Pro Pro Ser Lys Asp Gly Ser Tyr Val Asn Leu Tyr Asp Ser Cys Val
            100                 105                 110

Asp Asp Thr Trp Asn Pro Lys Ala Phe Val Val Phe Asp Ala Asn Gln
        115                 120                 125

Ile Tyr Pro Glu Tyr Leu Ile Asp Phe His
    130                 135

<210> SEQ ID NO 19
<211> LENGTH: 181
<212> TYPE: PRT
<213> ORGANISM: Homo sapiens

<400> SEQUENCE: 19

Gly Phe Gln Lys Ile Thr Leu Ser Ser Ser Glu Glu Tyr Gln Lys
1               5                   10                  15

Val Trp Asn Leu Phe Asn Arg Thr Leu Pro Phe Tyr Phe Val Gln Lys
            20                  25                  30

Ile Glu Arg Val Gln Asn Leu Ala Leu Trp Glu Val Tyr Gln Trp Gln
        35                  40                  45

Lys Gly Gln Met Gln Lys Gln Asn Gly Gly Lys Ala Val Asp Glu Arg
    50                  55                  60

Gln Leu Phe His Gly Thr Ser Ala Ile Phe Val Asp Ala Ile Cys Gln
65                  70                  75                  80

Gln Asn Phe Asp Trp Arg Val Cys Gly Val His Gly Thr Ser Tyr Gly
                85                  90                  95

Lys Gly Ser Tyr Phe Ala Arg Asp Ala Ala Tyr Ser His His Tyr Ser
            100                 105                 110

Lys Ser Asp Thr Gln Thr His Thr Met Phe Leu Ala Arg Val Leu Val
        115                 120                 125

Gly Glu Phe Val Arg Gly Asn Ala Ser Phe Val Arg Pro Pro Ala Lys
    130                 135                 140

Glu Gly Trp Ser Asn Ala Phe Tyr Asp Ser Cys Val Asn Ser Val Ser
145                 150                 155                 160

Asp Pro Ser Gly Phe Val Ile Phe Glu Lys His Gln Val Tyr Pro Glu
                165                 170                 175

Tyr Val Ile Gln Tyr
            180

<210> SEQ ID NO 20
<211> LENGTH: 181
<212> TYPE: PRT
<213> ORGANISM: Homo sapiens
```

<400> SEQUENCE: 20

Gly Phe Gln Lys Ile Thr Leu Ser Ser Ser Glu Glu Tyr Gln Lys
1               5                   10                  15

Val Trp Asn Leu Phe Asn Arg Thr Leu Pro Phe Tyr Phe Val Gln Lys
            20                  25                  30

Ile Glu Arg Val Gln Asn Leu Ala Leu Trp Glu Val Tyr Gln Trp Gln
            35                  40                  45

Lys Gly Gln Met Gln Lys Gln Asn Gly Gly Lys Ala Val Asp Glu Arg
        50                  55                  60

Gln Leu Phe His Gly Thr Ser Ala Ile Phe Val Asp Ala Ile Cys Gln
65              70                  75                  80

Gln Asn Phe Asp Trp Arg Val Cys Gly Val His Gly Thr Ser Tyr Gly
                85                  90                  95

Lys Gly Ser Tyr Phe Ala Arg Asp Ala Ala Tyr Ser His His Tyr Ser
            100                 105                 110

Lys Ser Asp Thr Gln Thr His Thr Met Phe Leu Ala Arg Val Leu Val
            115                 120                 125

Gly Glu Phe Val Arg Gly Asn Ala Ser Phe Val Arg Pro Pro Ala Lys
        130                 135                 140

Glu Gly Trp Ser Asn Ala Phe Tyr Asp Ser Cys Val Asn Ser Val Ser
145                 150                 155                 160

Asp Pro Ser Ala Phe Val Ile Phe Glu Lys His Gln Val Tyr Pro Glu
                165                 170                 175

Tyr Val Ile Gln Tyr
            180

<210> SEQ ID NO 21
<211> LENGTH: 183
<212> TYPE: PRT
<213> ORGANISM: Homo sapiens

<400> SEQUENCE: 21

Cys Val Val Glu Leu Leu Pro Ser Asp Pro Glu Tyr Asn Thr Val Ala
1               5                   10                  15

Ser Lys Phe Asn Gln Thr Cys Ser His Phe Arg Ile Glu Lys Ile Glu
            20                  25                  30

Arg Ile Gln Asn Pro Asp Leu Trp Asn Ser Tyr Gln Ala Lys Lys Lys
            35                  40                  45

Thr Met Asp Ala Lys Asn Gly Gln Thr Met Asn Glu Lys Gln Leu Phe
        50                  55                  60

His Gly Thr Asp Ala Gly Ser Val Pro His Val Asn Arg Asn Gly Phe
65              70                  75                  80

Asn Arg Ser Tyr Ala Gly Lys Asn Ala Val Ala Tyr Gly Lys Gly Thr
                85                  90                  95

Tyr Phe Ala Val Asn Ala Asn Tyr Ser Ala Asn Asp Thr Tyr Ser Arg
            100                 105                 110

Pro Asp Ala Asn Gly Arg Lys His Val Tyr Val Arg Val Leu Thr
            115                 120                 125

Gly Ile Tyr Thr His Gly Asn His Ser Leu Ile Val Pro Pro Ser Lys
        130                 135                 140

Asn Pro Gln Asn Pro Thr Asp Leu Tyr Asp Thr Val Thr Asp Asn Val
145                 150                 155                 160

His His Pro Ser Gly Phe Val Ala Phe Tyr Asp Tyr Gln Ala Tyr Pro
                165                 170                 175

Glu Tyr Leu Ile Thr Phe Arg
            180

<210> SEQ ID NO 22
<211> LENGTH: 183
<212> TYPE: PRT
<213> ORGANISM: Homo sapiens

<400> SEQUENCE: 22

Cys Val Glu Leu Leu Pro Ser Asp Pro Glu Tyr Asn Thr Val Ala
1               5                   10                  15

Ser Lys Phe Asn Gln Thr Cys Ser His Phe Arg Ile Glu Lys Ile Glu
                20                  25                  30

Arg Ile Gln Asn Pro Asp Leu Trp Asn Ser Tyr Gln Ala Lys Lys Lys
            35                  40                  45

Thr Met Asp Ala Lys Asn Gly Gln Thr Met Asn Glu Lys Gln Leu Phe
        50                  55                  60

His Gly Thr Asp Ala Gly Ser Val Pro His Val Asn Arg Asn Gly Phe
65                  70                  75                  80

Asn Arg Ser Tyr Ala Gly Lys Asn Ala Val Ala Tyr Gly Lys Gly Thr
                85                  90                  95

Tyr Phe Ala Val Asn Ala Asn Tyr Ser Ala Asn Asp Thr Tyr Ser Arg
            100                 105                 110

Pro Asp Ala Asn Gly Arg Lys His Val Tyr Tyr Val Arg Val Leu Thr
        115                 120                 125

Gly Ile Tyr Thr His Gly Asn His Ser Leu Ile Val Pro Pro Ser Lys
    130                 135                 140

Asn Pro Gln Asn Pro Thr Asp Leu Tyr Asp Thr Val Thr Asp Asn Val
145                 150                 155                 160

His His Pro Ser Ala Phe Val Ala Phe Tyr Asp Tyr Gln Ala Tyr Pro
                165                 170                 175

Glu Tyr Leu Ile Thr Phe Arg
            180

<210> SEQ ID NO 23
<211> LENGTH: 178
<212> TYPE: PRT
<213> ORGANISM: Homo sapiens

<400> SEQUENCE: 23

Leu Glu Pro Gly Gln Ser Glu Tyr Asn Thr Ile Lys Asp Lys Phe Thr
1               5                   10                  15

Arg Thr Cys Ser Ser Tyr Ala Ile Glu Lys Ile Glu Arg Ile Gln Asn
                20                  25                  30

Ala Phe Leu Trp Gln Ser Tyr Gln Val Lys Lys Arg Gln Met Asp Ile
            35                  40                  45

Lys Asn Asp His Lys Asn Asn Glu Arg Leu Leu Phe His Gly Thr Asp
        50                  55                  60

Ala Asp Ser Val Pro Tyr Val Asn Gln His Gly Phe Asn Arg Ser Cys
65                  70                  75                  80

Ala Gly Lys Asn Ala Val Ser Tyr Gly Lys Gly Thr Tyr Phe Ala Val
                85                  90                  95

Asp Ala Ser Tyr Ser Ala Lys Asp Thr Tyr Ser Lys Pro Asp Ser Asn
            100                 105                 110

Gly Arg Lys His Met Tyr Val Val Arg Val Leu Thr Gly Val Phe Thr
        115                 120                 125

Lys Gly Arg Ala Gly Leu Val Thr Pro Pro Lys Asn Pro His Asn
                130                 135                 140

Pro Thr Asp Leu Phe Asp Ser Val Thr Asn Asn Thr Arg Ser Pro Lys
145                 150                 155                 160

Gly Phe Val Val Phe Asp Asn Gln Ala Tyr Pro Glu Tyr Leu Ile
                165                 170                 175

Thr Phe

<210> SEQ ID NO 24
<211> LENGTH: 178
<212> TYPE: PRT
<213> ORGANISM: Homo sapiens

<400> SEQUENCE: 24

Leu Glu Pro Gly Gln Ser Glu Tyr Asn Thr Ile Lys Asp Lys Phe Thr
1               5                   10                  15

Arg Thr Cys Ser Ser Tyr Ala Ile Glu Lys Ile Glu Arg Ile Gln Asn
                20                  25                  30

Ala Phe Leu Trp Gln Ser Tyr Gln Val Lys Lys Arg Gln Met Asp Ile
            35                  40                  45

Lys Asn Asp His Lys Asn Asn Glu Arg Leu Leu Phe His Gly Thr Asp
50                  55                  60

Ala Asp Ser Val Pro Tyr Val Asn Gln His Gly Phe Asn Arg Ser Cys
65                  70                  75                  80

Ala Gly Lys Asn Ala Val Ser Tyr Gly Lys Gly Thr Tyr Phe Ala Val
                85                  90                  95

Asp Ala Ser Tyr Ser Ala Lys Asp Thr Tyr Ser Lys Pro Asp Ser Asn
            100                 105                 110

Gly Arg Lys His Met Tyr Val Val Arg Val Leu Thr Gly Val Phe Thr
        115                 120                 125

Lys Gly Arg Ala Gly Leu Val Thr Pro Pro Lys Asn Pro His Asn
                130                 135                 140

Pro Thr Asp Leu Phe Asp Ser Val Thr Asn Asn Thr Arg Ser Pro Lys
145                 150                 155                 160

Ala Phe Val Val Phe Asp Asn Gln Ala Tyr Pro Glu Tyr Leu Ile
                165                 170                 175

Thr Phe

<210> SEQ ID NO 25
<211> LENGTH: 179
<212> TYPE: PRT
<213> ORGANISM: Homo sapiens

<400> SEQUENCE: 25

Leu Thr Ile His Ser Ala Gly Lys Ala Glu Phe Glu Lys Ile Gln Lys
1               5                   10                  15

Leu Thr Gly Ala Pro His Thr Pro Val Pro Ala Pro Asp Phe Leu Phe
                20                  25                  30

Glu Ile Glu Tyr Phe Asp Pro Ala Asn Ala Lys Phe Tyr Glu Thr Lys
            35                  40                  45

Gly Glu Arg Asp Leu Ile Tyr Ala Phe His Gly Ser Arg Leu Glu Asn
50                  55                  60

Phe His Ser Ile Ile His Asn Gly Leu His Cys His Leu Asn Lys Thr
65                  70                  75                  80

Ser Leu Phe Gly Glu Gly Thr Tyr Leu Thr Ser Asp Leu Ser Leu Ala
                85                  90                  95

```
Leu Ile Tyr Ser Pro His Gly His Gly Trp Gln His Ser Leu Leu Gly
                100                 105                 110

Pro Ile Leu Ser Cys Val Ala Val Cys Glu Val Ile Asp His Pro Asp
            115                 120                 125

Val Lys Cys Gln Thr Lys Lys Lys Asp Ser Lys Glu Ile Asp Arg Arg
130                 135                 140

Arg Ala Arg Ile Lys His Ser Glu Gly Gly Asp Ile Pro Pro Lys Gly
145                 150                 155                 160

Phe Val Val Thr Asn Asn Gln Leu Leu Arg Val Lys Tyr Leu Leu Val
                165                 170                 175

Tyr Ser Gln

<210> SEQ ID NO 26
<211> LENGTH: 179
<212> TYPE: PRT
<213> ORGANISM: Homo sapiens

<400> SEQUENCE: 26

Leu Thr Ile His Ser Ala Gly Lys Ala Glu Phe Glu Lys Ile Gln Lys
1               5                   10                  15

Leu Thr Gly Ala Pro His Thr Pro Val Pro Ala Pro Asp Phe Leu Phe
            20                  25                  30

Glu Ile Glu Tyr Phe Asp Pro Ala Asn Ala Lys Phe Tyr Glu Thr Lys
        35                  40                  45

Gly Glu Arg Asp Leu Ile Tyr Ala Phe His Gly Ser Arg Leu Glu Asn
    50                  55                  60

Phe His Ser Ile Ile His Asn Gly Leu His Cys His Leu Asn Lys Thr
65                  70                  75                  80

Ser Leu Phe Gly Glu Gly Thr Tyr Leu Thr Ser Asp Leu Ser Leu Ala
                85                  90                  95

Leu Ile Tyr Ser Pro His Gly His Gly Trp Gln His Ser Leu Leu Gly
                100                 105                 110

Pro Ile Leu Ser Cys Val Ala Val Cys Glu Val Ile Asp His Pro Asp
            115                 120                 125

Val Lys Cys Gln Thr Lys Lys Lys Asp Ser Lys Glu Ile Asp Arg Arg
130                 135                 140

Arg Ala Arg Ile Lys His Ser Glu Gly Gly Asp Ile Pro Pro Lys Ala
145                 150                 155                 160

Phe Val Val Thr Asn Asn Gln Leu Leu Arg Val Lys Tyr Leu Leu Val
                165                 170                 175

Tyr Ser Gln

<210> SEQ ID NO 27
<211> LENGTH: 227
<212> TYPE: PRT
<213> ORGANISM: Homo sapiens

<400> SEQUENCE: 27

Glu Met Thr Gln Gly Ser Tyr Leu Glu Ile Lys Lys Gln Met Asp Lys
1               5                   10                  15

Leu Asp Pro Leu Ala His Pro Leu Gln Trp Ile Ile Ser Ser Asn
            20                  25                  30

Arg Ser His Ile Val Lys Leu Pro Leu Ser Arg Leu Lys Phe Met His
        35                  40                  45

Thr Ser His Gln Phe Leu Leu Leu Ser Ser Pro Pro Ala Lys Glu Ala
```

```
            50                  55                  60
Arg Phe Arg Thr Ala Lys Lys Leu Tyr Gly Ser Thr Phe Ala Phe His
 65                  70                  75                  80

Gly Ser His Ile Glu Asn Trp His Ser Ile Leu Arg Asn Gly Leu Val
                 85                  90                  95

Asn Ala Ser Tyr Thr Lys Leu Gln Leu His Gly Ala Ala Tyr Gly Lys
            100                 105                 110

Gly Ile Tyr Leu Ser Pro Ile Ser Ser Ile Ser Phe Gly Tyr Ser Gly
        115                 120                 125

Met Gly Lys Gly Gln His Arg Met Pro Ser Lys Asp Glu Leu Val Gln
130                 135                 140

Arg Tyr Asn Arg Met Asn Thr Ile Pro Gln Thr Arg Ser Ile Gln Ser
145                 150                 155                 160

Arg Phe Leu Gln Ser Arg Asn Leu Asn Cys Ile Ala Leu Cys Glu Val
                165                 170                 175

Ile Thr Ser Lys Asp Leu Gln Lys His Gly Asn Ile Trp Val Cys Pro
            180                 185                 190

Val Ser Asp His Val Cys Thr Arg Phe Phe Phe Val Tyr Glu Asp Gly
        195                 200                 205

Gln Val Gly Asp Ala Asn Ile Asn Thr Gln Asp Pro Lys Ile Gln Lys
210                 215                 220

Glu Ile Met
225

<210> SEQ ID NO 28
<211> LENGTH: 209
<212> TYPE: PRT
<213> ORGANISM: Homo sapiens

<400> SEQUENCE: 28

Tyr Pro Glu Thr Trp Val Tyr Met His Pro Ser Gln Asp Phe Ile Gln
 1               5                  10                  15

Val Pro Val Ser Ala Glu Asp Lys Ser Tyr Arg Ile Ile Tyr Asn Leu
            20                  25                  30

Phe His Lys Thr Val Pro Glu Phe Lys Tyr Arg Ile Leu Gln Ile Leu
        35                  40                  45

Arg Val Gln Asn Gln Phe Leu Trp Glu Lys Tyr Lys Arg Lys Lys Glu
    50                  55                  60

Tyr Met Asn Arg Lys Met Phe Gly Arg Asp Arg Ile Ile Asn Glu Arg
 65                  70                  75                  80

His Leu Phe His Gly Thr Ser Gln Asp Val Val Asp Gly Ile Cys Lys
                 85                  90                  95

His Asn Phe Asp Pro Arg Val Cys Gly Lys His Ala Thr Met Phe Gly
            100                 105                 110

Gln Gly Ser Tyr Phe Ala Lys Lys Ala Ser Tyr Ser His Asn Phe Ser
        115                 120                 125

Lys Lys Ser Ser Lys Gly Val His Phe Met Phe Leu Ala Lys Val Leu
    130                 135                 140

Thr Gly Arg Tyr Thr Met Gly Ser His Gly Met Arg Arg Pro Pro Pro
145                 150                 155                 160

Val Asn Pro Gly Ser Val Thr Ser Asp Leu Tyr Asp Ser Cys Val Asp
                165                 170                 175

Asn Phe Phe Glu Pro Gln Ile Phe Val Ile Phe Asn Asp Asp Gln Ser
            180                 185                 190
```

```
Tyr Pro Tyr Phe Val Ile Gln Tyr Glu Val Ser Asn Thr Val Ser
        195                 200                 205
Ile

<210> SEQ ID NO 29
<211> LENGTH: 228
<212> TYPE: PRT
<213> ORGANISM: Homo sapiens

<400> SEQUENCE: 29

Glu Met Thr Gln Ala Pro Tyr Leu Glu Ile Lys Lys Gln Met Asp Lys
1               5                   10                  15

Gln Asp Pro Leu Ala His Pro Leu Leu Gln Trp Val Ile Ser Ser Asn
            20                  25                  30

Arg Ser His Ile Val Lys Leu Pro Val Asn Arg Gln Leu Lys Phe Met
        35                  40                  45

His Thr Pro His Gln Phe Leu Leu Ser Pro Pro Ala Lys Glu
    50                  55                  60

Ser Asn Phe Arg Ala Ala Lys Lys Leu Phe Gly Ser Thr Phe Ala Phe
65              70                  75                  80

His Gly Ser His Ile Glu Asn Trp His Ser Ile Leu Arg Asn Gly Leu
                85                  90                  95

Val Val Ala Ser Asn Thr Arg Leu Gln Leu His Gly Ala Met Tyr Gly
            100                 105                 110

Ser Gly Ile Tyr Leu Ser Pro Met Ser Ser Ile Ser Phe Gly Tyr Ser
        115                 120                 125

Gly Met Asn Lys Lys Gln Lys Val Ser Ala Lys Asp Glu Pro Ala Ser
130                 135                 140

Ser Ser Lys Ser Ser Asn Thr Ser Gln Ser Gln Lys Lys Gly Gln Gln
145                 150                 155                 160

Ser Gln Phe Leu Gln Ser Arg Asn Leu Lys Cys Ile Ala Leu Cys Glu
                165                 170                 175

Val Ile Thr Ser Ser Asp Leu His Lys His Gly Glu Ile Trp Val Val
            180                 185                 190

Pro Asn Thr Asp His Val Cys Thr Arg Phe Phe Phe Val Tyr Glu Asp
        195                 200                 205

Gly Gln Val Gly Asp Ala Asn Ile Asn Thr Gln Glu Gly Gly Ile His
    210                 215                 220

Lys Glu Ile Leu
225

<210> SEQ ID NO 30
<211> LENGTH: 220
<212> TYPE: PRT
<213> ORGANISM: Homo sapiens

<400> SEQUENCE: 30

Pro Thr Leu Ala Gly Gln Thr Leu Lys Gly Pro Trp Asn Asn Leu Glu
1               5                   10                  15

Arg Leu Ala Glu Asn Thr Gly Glu Phe Gln Glu Val Val Arg Ala Phe
            20                  25                  30

Tyr Asp Thr Leu Asp Ala Ala Arg Ser Ser Ile Arg Val Arg Val
        35                  40                  45

Glu Arg Val Ser His Pro Leu Leu Gln Gln Tyr Glu Leu Tyr Arg
    50                  55                  60

Glu Arg Leu Leu Gln Arg Cys Glu Arg Arg Pro Val Glu Gln Val Leu
```

```
                65                  70                  75                  80
        Tyr His Gly Thr Thr Ala Pro Ala Val Pro Asp Ile Cys Ala His Gly
                        85                  90                  95

Phe Asn Arg Ser Phe Cys Gly Arg Asn Ala Thr Val Tyr Gly Lys Gly
                        100                 105                 110

Val Tyr Phe Ala Arg Arg Ala Ser Leu Ser Val Gln Asp Arg Tyr Ser
                        115                 120                 125

Pro Pro Asn Ala Asp Gly His Lys Ala Val Phe Val Ala Arg Val Leu
                130                 135                 140

Thr Gly Asp Tyr Gly Gln Gly Arg Arg Gly Leu Arg Ala Pro Pro Leu
        145                 150                 155                 160

Arg Gly Pro Gly His Val Leu Leu Arg Tyr Asp Ser Ala Val Asp Cys
                        165                 170                 175

Ile Cys Gln Pro Ser Ile Phe Val Ile Phe His Asp Thr Gln Ala Leu
                        180                 185                 190

Pro Thr His Leu Ile Thr Cys Glu His Val Pro Arg Ala Ser Pro Asp
                        195                 200                 205

Asp Pro Ser Gly Leu Pro Gly Arg Ser Pro Asp Thr
                210                 215                 220

<210> SEQ ID NO 31
<211> LENGTH: 216
<212> TYPE: PRT
<213> ORGANISM: Homo sapiens

<400> SEQUENCE: 31

Ile Pro Met Pro Thr His Trp Glu Asn Val Asn Thr Gln Val Pro Tyr
        1               5                   10                  15

Gln Leu Ile Pro Leu His Asn Gln Thr His Glu Tyr Asn Glu Val Ala
                        20                  25                  30

Asn Leu Phe Gly Lys Thr Met Asp Arg Asn Arg Ile Lys Arg Ile Gln
                        35                  40                  45

Arg Ile Gln Asn Leu Asp Leu Trp Glu Phe Phe Cys Arg Lys Lys Ala
                50                  55                  60

Gln Leu Lys Lys Lys Arg Gly Val Pro Gln Ile Asn Glu Gln Met Leu
        65                  70                  75                  80

Phe His Gly Thr Ser Ser Glu Phe Val Glu Ala Ile Cys Ile His Asn
                        85                  90                  95

Phe Asp Trp Arg Ile Asn Gly Ile His Gly Ala Val Phe Gly Lys Gly
                        100                 105                 110

Thr Tyr Phe Ala Arg Asp Ala Ala Tyr Ser Ser Arg Phe Cys Lys Asp
                        115                 120                 125

Asp Ile Lys His Gly Asn Thr Phe Gln Ile His Gly Val Ser Leu Gln
                130                 135                 140

Gln Arg His Leu Phe Arg Thr Tyr Lys Ser Met Phe Leu Ala Arg Val
        145                 150                 155                 160

Leu Ile Gly Asp Tyr Ile Asn Gly Asp Ser Lys Tyr Met Arg Pro Pro
                        165                 170                 175

Ser Lys Asp Gly Ser Tyr Val Asn Leu Tyr Asp Ser Cys Val Asp Asp
                        180                 185                 190

Thr Trp Asn Pro Lys Ile Phe Val Phe Asp Ala Asn Gln Ile Tyr
                        195                 200                 205

Pro Glu Tyr Leu Ile Asp Phe His
                210                 215
```

```
<210> SEQ ID NO 32
<211> LENGTH: 215
<212> TYPE: PRT
<213> ORGANISM: Homo sapiens

<400> SEQUENCE: 32

Ile Pro Asp Tyr Trp Asp Ser Ser Ala Leu Pro Asp Pro Gly Phe Gln
1               5                   10                  15

Lys Ile Thr Leu Ser Ser Ser Glu Glu Tyr Gln Lys Val Trp Asn
            20                  25                  30

Leu Phe Asn Arg Thr Leu Pro Phe Tyr Val Gln Lys Ile Glu Arg
        35                  40                  45

Val Gln Asn Leu Ala Leu Trp Glu Val Tyr Gln Trp Gln Lys Gly Gln
50                  55                  60

Met Gln Lys Gln Asn Gly Gly Lys Ala Val Asp Glu Arg Gln Leu Phe
65                  70                  75                  80

His Gly Thr Ser Ala Ile Phe Val Asp Ala Ile Cys Gln Gln Asn Phe
                85                  90                  95

Asp Trp Arg Val Cys Gly Val His Gly Thr Ser Tyr Gly Lys Gly Ser
            100                 105                 110

Tyr Phe Ala Arg Asp Ala Ala Tyr Ser His His Tyr Ser Lys Ser Asp
        115                 120                 125

Thr Gln Thr His Thr Met Phe Leu Ala Arg Val Leu Val Gly Glu Phe
    130                 135                 140

Val Arg Gly Asn Ala Ser Phe Val Arg Pro Ala Lys Glu Gly Trp
145                 150                 155                 160

Ser Asn Ala Phe Tyr Asp Ser Cys Val Asn Ser Val Ser Asp Pro Ser
                165                 170                 175

Ile Phe Val Ile Phe Glu Lys His Gln Val Tyr Pro Glu Tyr Val Ile
            180                 185                 190

Gln Tyr Thr Thr Ser Ser Lys Pro Ser Val Thr Pro Ser Ile Leu Leu
        195                 200                 205

Ala Leu Gly Ser Leu Phe Ser
    210                 215

<210> SEQ ID NO 33
<211> LENGTH: 197
<212> TYPE: PRT
<213> ORGANISM: Homo sapiens

<400> SEQUENCE: 33

Ile Pro Ala His Trp Ser Asp Met Lys Gln Gln Asn Phe Cys Val Val
1               5                   10                  15

Glu Leu Leu Pro Ser Asp Pro Glu Tyr Asn Thr Val Ala Ser Lys Phe
            20                  25                  30

Asn Gln Thr Cys Ser His Phe Arg Ile Glu Lys Ile Glu Arg Ile Gln
        35                  40                  45

Asn Pro Asp Leu Trp Asn Ser Tyr Gln Ala Lys Lys Thr Met Asp
50                  55                  60

Ala Lys Asn Gly Gln Thr Met Asn Glu Lys Gln Leu Phe His Gly Thr
65                  70                  75                  80

Asp Ala Gly Ser Val Pro His Val Asn Arg Asn Gly Phe Asn Arg Ser
                85                  90                  95

Tyr Ala Gly Lys Asn Ala Val Ala Tyr Gly Lys Gly Tyr Phe Ala
            100                 105                 110
```

```
Val Asn Ala Asn Tyr Ser Ala Asn Asp Thr Tyr Ser Arg Pro Asp Ala
            115                 120                 125

Asn Gly Arg Lys His Val Tyr Tyr Val Arg Val Leu Thr Gly Ile Tyr
        130                 135                 140

Thr His Gly Asn His Ser Leu Ile Val Pro Ser Lys Asn Pro Gln
145                 150                 155                 160

Asn Pro Thr Asp Leu Tyr Asp Thr Val Thr Asp Asn Val His His Pro
                165                 170                 175

Ser Leu Phe Val Ala Phe Tyr Asp Tyr Gln Ala Tyr Pro Glu Tyr Leu
            180                 185                 190

Ile Thr Phe Arg Lys
        195
```

<210> SEQ ID NO 34
<211> LENGTH: 197
<212> TYPE: PRT
<213> ORGANISM: Homo sapiens

<400> SEQUENCE: 34

```
Leu Pro Glu His Trp Thr Asp Met Asn His Gln Leu Phe Cys Met Val
1               5                   10                  15

Gln Leu Glu Pro Gly Gln Ser Glu Tyr Asn Thr Ile Lys Asp Lys Phe
            20                  25                  30

Thr Arg Thr Cys Ser Ser Tyr Ala Ile Glu Lys Ile Glu Arg Ile Gln
        35                  40                  45

Asn Ala Phe Leu Trp Gln Ser Tyr Gln Val Lys Lys Arg Gln Met Asp
50                  55                  60

Ile Lys Asn Asp His Lys Asn Asn Glu Arg Leu Leu Phe His Gly Thr
65                  70                  75                  80

Asp Ala Asp Ser Val Pro Tyr Val Asn Gln His Gly Phe Asn Arg Ser
                85                  90                  95

Cys Ala Gly Lys Asn Ala Val Ser Tyr Gly Lys Gly Thr Tyr Phe Ala
            100                 105                 110

Val Asp Ala Ser Tyr Ser Ala Lys Asp Thr Tyr Ser Lys Pro Asp Ser
            115                 120                 125

Asn Gly Arg Lys His Met Tyr Val Val Arg Val Leu Thr Gly Val Phe
        130                 135                 140

Thr Lys Gly Arg Ala Gly Leu Val Thr Pro Pro Lys Asn Pro His
145                 150                 155                 160

Asn Pro Thr Asp Leu Phe Asp Ser Val Thr Asn Asn Thr Arg Ser Pro
                165                 170                 175

Lys Leu Phe Val Val Phe Phe Asp Asn Gln Ala Tyr Pro Glu Tyr Leu
            180                 185                 190

Ile Thr Phe Thr Ala
        195
```

<210> SEQ ID NO 35
<211> LENGTH: 186
<212> TYPE: PRT
<213> ORGANISM: Homo sapiens

<400> SEQUENCE: 35

```
Val Leu Thr Ile His Ser Ala Gly Lys Ala Glu Phe Glu Lys Ile Gln
1               5                   10                  15

Lys Leu Thr Gly Ala Pro His Thr Pro Val Pro Ala Pro Asp Phe Leu
            20                  25                  30
```

```
Phe Glu Ile Glu Tyr Phe Asp Pro Ala Asn Ala Lys Phe Tyr Glu Thr
             35                  40                  45

Lys Gly Glu Arg Asp Leu Ile Tyr Ala Phe His Gly Ser Arg Leu Glu
 50                  55                  60

Asn Phe His Ser Ile Ile His Asn Gly Leu His Cys His Leu Asn Lys
 65                  70                  75                  80

Thr Ser Leu Phe Gly Glu Gly Thr Tyr Leu Thr Ser Asp Leu Ser Leu
                 85                  90                  95

Ala Leu Ile Tyr Ser Pro His Gly His Gly Trp Gln His Ser Leu Leu
             100                 105                 110

Gly Pro Ile Leu Ser Cys Val Ala Val Cys Glu Val Ile Asp His Pro
         115                 120                 125

Asp Val Lys Cys Gln Thr Lys Lys Asp Ser Lys Glu Ile Asp Arg
         130                 135                 140

Arg Arg Ala Arg Ile Lys His Ser Glu Gly Gly Asp Ile Pro Pro Lys
145                 150                 155                 160

Tyr Phe Val Val Thr Asn Asn Gln Leu Leu Arg Val Lys Tyr Leu Leu
                 165                 170                 175

Val Tyr Ser Gln Lys Pro Pro Lys Arg Ala
            180                 185

<210> SEQ ID NO 36
<211> LENGTH: 9
<212> TYPE: PRT
<213> ORGANISM: Homo sapiens

<400> SEQUENCE: 36

Asp Met Val Ser Lys Ser Ala Asn Tyr
1               5

<210> SEQ ID NO 37
<211> LENGTH: 9
<212> TYPE: PRT
<213> ORGANISM: Homo sapiens

<400> SEQUENCE: 37

Leu Leu Tyr Asn Glu Tyr Ile Val Tyr
1               5

<210> SEQ ID NO 38
<211> LENGTH: 9
<212> TYPE: PRT
<213> ORGANISM: Homo sapiens

<400> SEQUENCE: 38

Asp Met Ser Ser Lys Ser Ala Asn Tyr
1               5

<210> SEQ ID NO 39
<211> LENGTH: 9
<212> TYPE: PRT
<213> ORGANISM: Homo sapiens

<400> SEQUENCE: 39

Leu Asn Tyr Asn Glu Phe Ile Val Tyr
1               5

<210> SEQ ID NO 40
<211> LENGTH: 9
<212> TYPE: PRT
<213> ORGANISM: Homo sapiens
```

<400> SEQUENCE: 40

Ser Glu Asn Ser Lys Ser Ala Gly Tyr
1               5

<210> SEQ ID NO 41
<211> LENGTH: 9
<212> TYPE: PRT
<213> ORGANISM: Homo sapiens

<400> SEQUENCE: 41

Phe Ser Gln Ser Glu Tyr Leu Ile Tyr
1               5

<210> SEQ ID NO 42
<211> LENGTH: 9
<212> TYPE: PRT
<213> ORGANISM: Homo sapiens

<400> SEQUENCE: 42

Asp Ser Leu Ser Thr Ser Ile Lys Tyr
1               5

<210> SEQ ID NO 43
<211> LENGTH: 9
<212> TYPE: PRT
<213> ORGANISM: Homo sapiens

<400> SEQUENCE: 43

Phe Glu Asp Asp Glu Phe Val Val Tyr
1               5

<210> SEQ ID NO 44
<211> LENGTH: 9
<212> TYPE: PRT
<213> ORGANISM: Homo sapiens

<400> SEQUENCE: 44

Glu Asn Ser Ser Lys Ser Asn Gln Tyr
1               5

<210> SEQ ID NO 45
<211> LENGTH: 9
<212> TYPE: PRT
<213> ORGANISM: Homo sapiens

<400> SEQUENCE: 45

Leu Ala Tyr Ala Glu Tyr Val Ile Tyr
1               5

<210> SEQ ID NO 46
<211> LENGTH: 9
<212> TYPE: PRT
<213> ORGANISM: Homo sapiens

<400> SEQUENCE: 46

Leu Ala Leu Ala Glu Tyr Val Ile Tyr
1               5

<210> SEQ ID NO 47
<211> LENGTH: 9
<212> TYPE: PRT
<213> ORGANISM: Homo sapiens

<400> SEQUENCE: 47

```
Pro Ile Ser Ser Ile Ser Phe Gly Tyr
1               5
```

<210> SEQ ID NO 48
<211> LENGTH: 9
<212> TYPE: PRT
<213> ORGANISM: Homo sapiens

<400> SEQUENCE: 48

```
Lys His Gly Asn Ile Trp Val Cys Pro
1               5
```

<210> SEQ ID NO 49
<211> LENGTH: 9
<212> TYPE: PRT
<213> ORGANISM: Homo sapiens

<400> SEQUENCE: 49

```
Lys Lys Ala Ser Tyr Ser His Asn Phe
1               5
```

<210> SEQ ID NO 50
<211> LENGTH: 9
<212> TYPE: PRT
<213> ORGANISM: Homo sapiens

<400> SEQUENCE: 50

```
Phe Glu Pro Gln Ile Phe Val Ile Phe
1               5
```

<210> SEQ ID NO 51
<211> LENGTH: 9
<212> TYPE: PRT
<213> ORGANISM: Homo sapiens

<400> SEQUENCE: 51

```
Pro Met Ser Ser Ile Ser Phe Gly Tyr
1               5
```

<210> SEQ ID NO 52
<211> LENGTH: 9
<212> TYPE: PRT
<213> ORGANISM: Homo sapiens

<400> SEQUENCE: 52

```
Lys His Gly Glu Ile Trp Val Val Pro
1               5
```

<210> SEQ ID NO 53
<211> LENGTH: 9
<212> TYPE: PRT
<213> ORGANISM: Homo sapiens

<400> SEQUENCE: 53

```
Arg Arg Ala Ser Leu Ser Val Gln Asp
1               5
```

<210> SEQ ID NO 54
<211> LENGTH: 9
<212> TYPE: PRT
<213> ORGANISM: Homo sapiens

<400> SEQUENCE: 54

```
Cys Gln Pro Ser Ile Phe Val Ile Phe
```

<210> SEQ ID NO 55
<211> LENGTH: 9
<212> TYPE: PRT
<213> ORGANISM: Homo sapiens

<400> SEQUENCE: 55

Arg Asp Ala Ala Tyr Ser Ser Arg Phe
1               5

<210> SEQ ID NO 56
<211> LENGTH: 9
<212> TYPE: PRT
<213> ORGANISM: Homo sapiens

<400> SEQUENCE: 56

Trp Asn Pro Lys Ile Phe Val Val Phe
1               5

<210> SEQ ID NO 57
<211> LENGTH: 9
<212> TYPE: PRT
<213> ORGANISM: Homo sapiens

<400> SEQUENCE: 57

Arg Asp Ala Ala Tyr Ser His His Tyr
1               5

<210> SEQ ID NO 58
<211> LENGTH: 9
<212> TYPE: PRT
<213> ORGANISM: Homo sapiens

<400> SEQUENCE: 58

Ser Asp Pro Ser Ile Phe Val Ile Phe
1               5

<210> SEQ ID NO 59
<211> LENGTH: 9
<212> TYPE: PRT
<213> ORGANISM: Homo sapiens

<400> SEQUENCE: 59

Val Asn Ala Asn Tyr Ser Ala Asn Asp
1               5

<210> SEQ ID NO 60
<211> LENGTH: 9
<212> TYPE: PRT
<213> ORGANISM: Homo sapiens

<400> SEQUENCE: 60

His His Pro Ser Leu Phe Val Ala Phe
1               5

<210> SEQ ID NO 61
<211> LENGTH: 9
<212> TYPE: PRT
<213> ORGANISM: Homo sapiens

<400> SEQUENCE: 61

Val Asp Ala Ser Tyr Ser Ala Lys Asp
1               5

```
<210> SEQ ID NO 62
<211> LENGTH: 9
<212> TYPE: PRT
<213> ORGANISM: Homo sapiens

<400> SEQUENCE: 62

Arg Ser Pro Lys Leu Phe Val Val Phe
1               5

<210> SEQ ID NO 63
<211> LENGTH: 9
<212> TYPE: PRT
<213> ORGANISM: Homo sapiens

<400> SEQUENCE: 63

Ser Asp Leu Ser Leu Ala Leu Ile Tyr
1               5

<210> SEQ ID NO 64
<211> LENGTH: 9
<212> TYPE: PRT
<213> ORGANISM: Homo sapiens

<400> SEQUENCE: 64

Ile Pro Pro Lys Tyr Phe Val Val Thr
1               5
```